(12) United States Patent
DeMulling et al.

(10) Patent No.: US 8,010,203 B2
(45) Date of Patent: Aug. 30, 2011

(54) GUIDED PROGRAMMING WITH FEEDBACK

(75) Inventors: Delight D. DeMulling, Lino Lakes, MN (US); Debbie A. McConnell, Edina, MN (US); Steven M. Goetz, Brooklyn Center, MN (US); Cari C. Herman, Ham Lake, MN (US); Wende L. Dewing, Edina, MN (US)

(73) Assignee: Medtronic, Inc., Minneapolis, MN (US)

( * ) Notice: Subject to any disclaimer, the term of this patent is extended or adjusted under 35 U.S.C. 154(b) by 1103 days.

(21) Appl. No.: 11/690,655

(22) Filed: Mar. 23, 2007

(65) Prior Publication Data
US 2008/0027514 A1 Jan. 31, 2008

Related U.S. Application Data

(60) Provisional application No. 60/785,107, filed on Mar. 23, 2006.

(51) Int. Cl.
*A61N 1/08* (2006.01)
(52) U.S. Cl. .......................................................... 607/59
(58) Field of Classification Search ................... 607/30, 607/31, 59
See application file for complete search history.

(56) References Cited

U.S. PATENT DOCUMENTS

| | | | |
|---|---|---|---|
| 4,432,360 | A | 2/1984 | Mumford et al. |
| 5,716,382 | A | 2/1998 | Snell |
| 6,292,701 | B1 | 9/2001 | Prass et al. |
| 6,308,102 | B1 | 10/2001 | Sieracki et al. |
| 6,609,032 | B1 | 8/2003 | Woods et al. |
| 6,622,048 | B1 | 9/2003 | Mann et al. |
| 6,978,171 | B2 | 12/2005 | Goetz et al. |
| 7,003,349 | B1 | 2/2006 | Andersson et al. |
| 7,020,523 | B1 | 3/2006 | Lu et al. |
| 2003/0236557 | A1 | 12/2003 | Whitehurst et al. |
| 2004/0199218 | A1* | 10/2004 | Lee et al. ................. 607/48 |
| 2004/0215288 | A1 | 10/2004 | Lee et al. |
| 2004/0267330 | A1* | 12/2004 | Lee et al. ................. 607/48 |

(Continued)

FOREIGN PATENT DOCUMENTS
EP 1 184 050 A2 3/2002
(Continued)

OTHER PUBLICATIONS

Notification of Transmittal of the International Search Report and the Written Opinion for corresponding PCT Application No. PCT/US2007/007368 dated Sep. 20, 2007, (13 pages).

(Continued)

*Primary Examiner* — Carl H Layno
*Assistant Examiner* — Jessica Sarcione
(74) *Attorney, Agent, or Firm* — Shumaker & Sieffert, P.A.

(57) ABSTRACT

Techniques that involve generating test stimulation programs based upon specific patient feedback to guide the programming process for stimulation therapy are described. The patient describes positive effects and adverse effects of the test stimulation by listing and/or rating specific types of effects, both positive and adverse, and the location of each effect. In this manner, a programming device, i.e. a programmer, uses the feedback to generate subsequent test stimulation programs. Initially, programs with unipolar electrode configurations are tested, but the programmer may generate bipolar electrode configurations to test if the patient rates the unipolar electrode combinations poorly. After the stimulation programs are tested and rated, the programmer sorts the tested programs based upon the feedback and presents the tested programs to the user. The user selects the best tested program to use for chronic stimulation therapy. Additionally, the patient may utilize the guided programming technique for continued therapy optimization.

49 Claims, 34 Drawing Sheets

U.S. PATENT DOCUMENTS

| | | |
|---|---|---|
| 2005/0060007 A1 | 3/2005 | Goetz |
| 2005/0060008 A1 | 3/2005 | Goetz |
| 2005/0060009 A1 | 3/2005 | Goetz |
| 2005/0060010 A1 | 3/2005 | Goetz |
| 2005/0245987 A1 | 11/2005 | Woods et al. |
| 2006/0015153 A1 | 1/2006 | Gliner et al. |
| 2006/0020292 A1 | 1/2006 | Goetz et al. |

FOREIGN PATENT DOCUMENTS

| | | |
|---|---|---|
| WO | WO 2006/105463 | 10/2006 |

OTHER PUBLICATIONS

Reply to Written Opinion in corresponding PCT Application No. PCT/US2007/007368 dated Jan. 15, 2008, (13 pages).

Notification of Transmittal of the International Preliminary Report on Patentability dated Jul. 2, 2008 for corresponding PCT Application Serial No. PCT/US2007/007368 (12 pgs).

European Office Action dated Apr. 21, 2009 for corresponding European Application Serial No. 07753952.6-1265 (5 pgs).

* cited by examiner

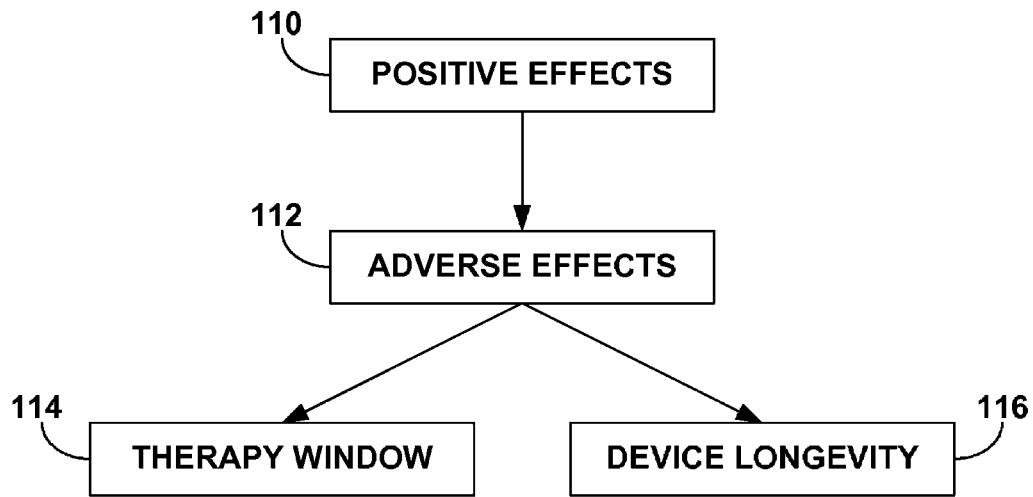
FIG. 8A
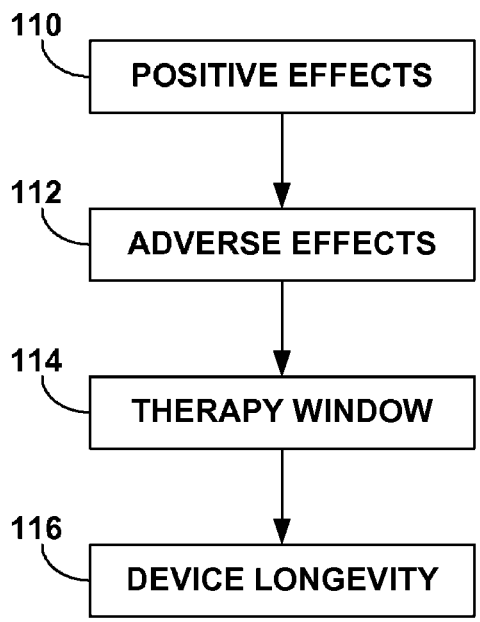 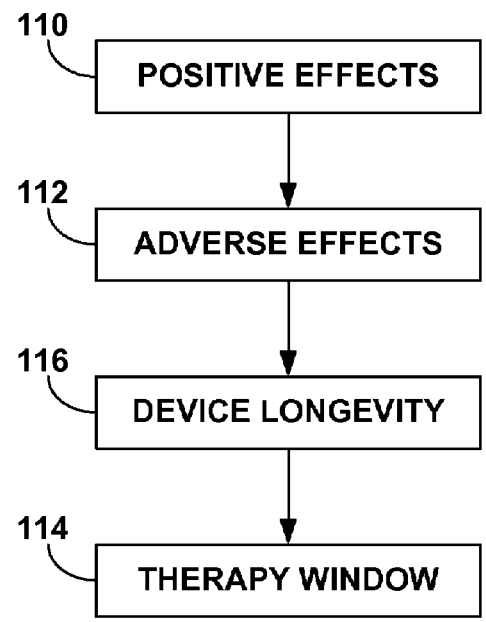
FIG. 8B　　　　FIG. 8C

Program Details

Use the arrows to view details for each program from Step 5: Choose Program. Click OK to select a program. Click Cancel, to close this screen without making a selection.

Current Program

Case +, 1-
Amp 2.5V
PW 60 μS
Rate 120 Hz

Effects
Normal (no tremor, normal muscle tone, etc)

Adverse Effects
No Adverse Effects

Therapy Window
1.5 volts (1.0 - 2.5)
Amplitude range from the first effect to the first adverse effect

338

[ < ] [ > ] [ Cancel ] [ OK ]

Header

Guided Programming for
John Doe STN Left                on/off

Step 6: End Session

Programming Facility
Boston MVD Clinic

Programmer Name
Susan Smith

Programmer Phone
123-444-5567

Physician Name
Susan Smith

Physician Phone
123-444-5567

Programs

| Lead | Active | Amp | |
|---|---|---|---|
| STN Left | Yes | 2.5 | View> |
| STN Right | Yes | 2.0 | View> |

384 — Overall Session Rating:
1 = Excellent ▼

386 — Print Report

388 — < Prev     End Session — 390

Footer

FIG. 36

GUIDED PROGRAMMING WITH FEEDBACK

This application claims the benefit of U.S. provisional application Ser. No. 60/785,107, filed Mar. 23, 2006, the entire content of which is incorporated herein by reference.

TECHNICAL FIELD

The invention relates to medical devices and, more particularly, to devices that deliver stimulation.

BACKGROUND

Implantable medical devices may be used to deliver neurostimulation therapy to patients to treat a variety of symptoms or conditions such as chronic pain, tremor, Parkinson's disease, epilepsy, urinary or fecal incontinence, sexual dysfunction, obesity, or gastroparesis. An implantable medical device may deliver neurostimulation therapy via leads that include electrodes located, for example, proximate to the spinal cord, pelvic nerves, stomach, or peripheral nervous system, or on or within the brain of a patient. In general, the implantable medical device delivers neurostimulation therapy in the form of electrical pulses.

A clinician selects values for a number of programmable parameters in order to define the neurostimulation therapy to be delivered to a patient. For example, the clinician selects an amplitude, which may be a current or voltage amplitude, and pulse width for a stimulation waveform to be delivered to the patient, as well as a rate at which the pulses are to be delivered to the patient. The clinician may also select particular electrodes within an electrode set implanted within the patient to be used to deliver the pulses, and the polarities of the selected electrodes. Selected electrodes and polarities may be referred to as an electrode configuration or combination. A group of parameter values, which may include an electrode configuration, may be referred to as a program in the sense that they drive the neurostimulation therapy to be delivered to the patient.

The process of selecting electrode configurations and parameter values for the stimulation parameters can be time consuming, and may require a great deal of trial and error before one or more preferred stimulation programs are discovered. As a portion of the overall parameter selection process, the process of selecting electrode configurations can be particularly time-consuming and tedious. The clinician typically needs to test a large number of possible electrode configurations within the electrode set implanted in the patient in order to identify preferred electrode configurations. This process is complex, especially for clinicians with limited experience programming stimulation therapy. Commonly, an expert from the manufacturer of the medical device or a specially trained clinician is needed to program the therapy with one or more preferred programs. A "preferred" program or electrode configuration may be a program or electrode configuration that provides a preferable balancing of efficacy, adverse effects, and stimulation device power consumption.

SUMMARY

The disclosure describes techniques that involve generating test stimulation programs based upon specific patient feedback to guide the programming process for electrical stimulation therapy. A programmer is used to generate stimulation programs for the patient to evaluate. The patient describes positive effects and adverse effects of the test stimulation by rating specific types of effects, both positive and adverse, and the location of each effect. The programmer uses the ratings to generate subsequent test stimulation programs.

Initially, unipolar electrode configurations may be used in the programs. However, the programmer may generate bipolar electrode configurations if the patient rates the unipolar electrode combinations poorly, or if it is otherwise determined that the therapy may be better with bipolar electrode configurations. After the stimulation programs are tested and rated, the programmer sorts the tested programs based upon the rating information and presents the tested programs to the user, which may be a physician, clinician, technician, or patient. A clinician will be used as the example of a user herein. The clinician selects the best, or one or more of the best, tested programs to use for chronic stimulation therapy. Additionally, the patient may utilize the guided programming technique for continued therapy optimization.

In one embodiment, the disclosure is directed to a method that includes providing test stimulation to a patient according to a plurality of programs, wherein each of the plurality of programs comprise a unipolar electrode combination, for at least one of the plurality of programs, receiving a positive input that indicates a positive effect resulting from provision of stimulation according to the program, and for at least one of the plurality of programs, receiving a negative input that indicates an adverse effect resulting from provision of stimulation according to the program. The method also includes automatically sorting the plurality of tested programs based upon the positive input and negative input.

In another embodiment, the disclosure is directed to a system that includes a stimulation signal generator that provides test stimulation to a patient according to a plurality of programs, wherein each of the plurality of programs comprise a unipolar electrode combination, a lead coupled to the stimulation signal generator, and a processor. The processor receives a positive input that indicates a positive effect resulting from provision of stimulation according to the program for at least one of the plurality of programs, receives a negative input that indicates an adverse effect resulting from provision of stimulation according to the program for at least one of the plurality of programs, and automatically sorts the plurality of tested programs based upon the positive input and negative input for each of the plurality of tested programs.

In an additional embodiment, the disclosure is directed to a computer-readable medium that includes instructions that cause a processor to provide test stimulation to a patient according to a plurality of programs, wherein each of the plurality of programs comprise a unipolar electrode combination, for at least one of the plurality of programs, receive a positive input that indicates a positive effect resulting from provision of stimulation according to the program, and for at least one of the plurality of programs, receive a negative input that indicates an adverse effect resulting from provision of stimulation according to the program. The computer-readable medium also includes instructions that cause the processor to automatically sort the plurality of tested programs based upon the positive input and negative input.

In various embodiments, the disclosure may provide one or more advantages. For example, less experienced clinicians and inexperienced users may be able to effectively identify stimulation programs without testing every conceivable combination of values for a plurality of stimulation parameters. In addition, the rating information from the patient for both positive and adverse effects, combined with the location of each effect, allows the programmer to eliminate certain stimulation programs from consideration, and direct the user to stimulation programs that may be more effective based upon the rating information. In other words, the guided programming techniques of various embodiments of the invention may reduce the time required for stimulation programming. Accordingly, this guided programming process may allow a clinician to treat a greater number of patients with a higher degree of effectiveness, than conventional trial and error programming techniques.

The details of one or more embodiments of the invention are set forth in the accompanying drawings and the description below. Other features, objects, and advantages of the invention will be apparent from the description and drawings, and from the claims.

BRIEF DESCRIPTION OF THE DRAWINGS

FIGS. 8A-8C are flow diagrams illustrating possible sorting techniques for evaluated electrodes during programming.

FIGS. 9-13 are example screen shots illustrating initial steps for system setup, the steps including collection of lead configuration and therapy information.

FIG. 28 is an example screen shot illustrating a pop-up window showing a summary of the selected program.

FIG. 36 is an example screen shot illustrating a step of viewing end session information summarizing the programming session in an example guided programming process.

DETAILED DESCRIPTION

The disclosure describes techniques to guide a user, e.g., a clinician, physician, technician or patient, during the programming of electrical stimulation therapy. The clinician will be used as the example user throughout. Programming involves the selection of a variety of stimulation parameters to create a set of parameters, i.e., a program, that defines the electrical stimulation delivered to the patient via a pulse generator. Selecting the preferred program that provides the greatest alleviation of the patient's condition and the minimal amount of adverse side effects is challenging to an experienced clinician, let alone a clinician unfamiliar with stimulation therapy or the patient. In many cases, implementing best practice information into the programming device regarding the types of programs that treat certain conditions and avoid particular adverse side effects may be beneficial to therapy efficacy.

The programmer described herein guides the clinician through the programming process. The clinician inputs rating information or feedback from the patient to rate each tested, or screened, stimulation program and automatically generate the next stimulation program to test. The input indicates and/or rates positive and adverse, or negative, effects, as well as the location of each effect. From this information, the programmer may use a look up table, effect map, or other stored guiding rules to generate the next stimulation program for the patient to evaluate. In this manner, the programming process may reduce the overall number of programs to test and quickly direct the clinician to programs that may be effective for the patient.

After the patient evaluates a plurality of programs generated by the programmer, the programming may display the tested programs to the clinician. The programmer sorts the programs based upon the magnitude of the positive and negative rating to quickly identify the best possible programs for effective stimulation therapy. As the patient continues with chronic stimulation therapy, the guided programming may be used again to optimize the therapy throughout the course of treatment.

Figure 1:
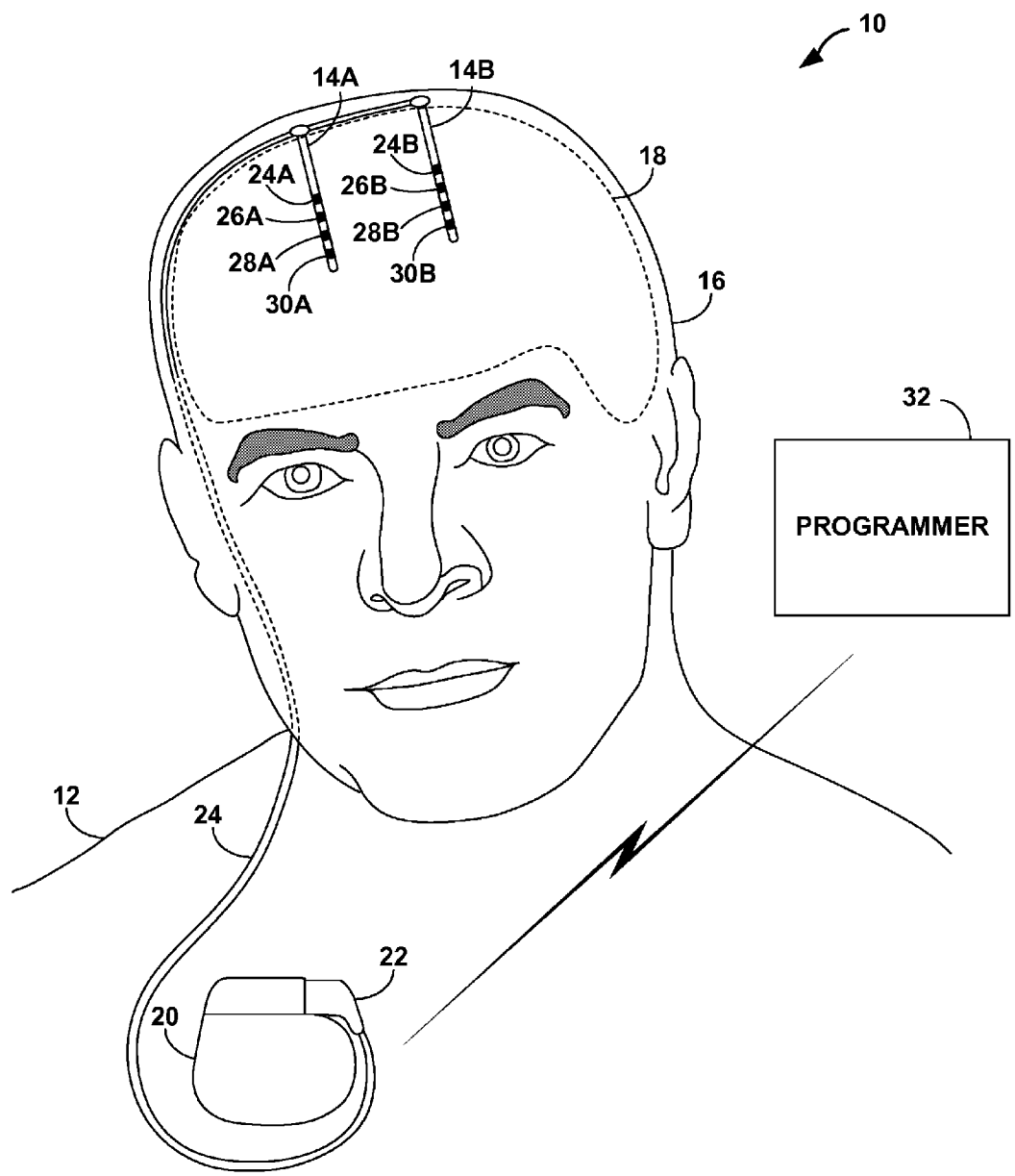
FIG. 1 is a conceptual diagram illustrating an example stimulation system in conjunction with a patient.

FIG. 1 is a conceptual diagram illustrating an example stimulation system in conjunction with a patient. As shown in FIG. 1, stimulation system 10 includes implantable medical device (IMD) 20, lead plug 22, lead wire 24 and leads 14A and 14B (collectively "leads 14") implanted within patient 12. Specifically, leads 14 enter through cranium 16 and implanted within brain 18 to deliver deep brain stimulation (DBS). Electrodes 24A and 24B, 26A and 26B, 28A and 28B and 30A and 30B (referred to herein as "electrodes 24, 26, 28 and 30") of leads 14A and 14B provide electrical pulses to surrounding anatomical regions of brain 18 in a therapy that may alleviate a condition of patient 12. Although the illustrated embodiments includes two leads 14, other embodiments may include a single lead 14, or greater than two leads 14 implanted within brain 18 of patient 12. Programmer 32 may be a handheld device, portable computer, or workstation that provides a user interface to a user, e.g., clinician. The clinician is guided though the programming process by interaction with the user interface of programmer 32.

DBS may be used to treat dysfunctional neuronal activity in the brain which manifests as diseases or disorders such as psychological disorders, including depression or obsessive-compulsive disorder, epilepsy, Hutchinson's Disease, Parkinson's Disease, or movement disorders. The exact mechanisms explaining why electrical stimulation therapy is capable of treating such conditions of the brain are unknown, but symptoms of these diseases can be lessened or eliminated with stimulation therapy. Certain anatomical regions of brain 18 are responsible for producing the symptoms of brain disorders. For example, stimulating an anatomical region called the Subthalamic Nucleus (STN) in brain 18 may reduce the number and magnitude of tremors experienced by patient 12. Anatomical regions such as these are targeted by the clinician during implantation of lead 14. In other words, the clinician attempts to position the lead as close to these regions as possible and utilizes effective stimulation programming to identify effective stimulation parameters to treat patient 12.

While DBS may successfully reduce symptoms of some neurological diseases, the stimulation commonly causes unwanted side effects as well. Adverse side effects may include incontinence, tingling, loss of balance, paralysis, slurred speech, loss of memory, and many other neurological problems. Adverse effects may be mild to severe; however, most side effects are reversible when stimulation is stopped. DBS may cause one or more adverse effects by inadvertently providing electrical stimulation pulses to anatomical regions near the targeted anatomical region. For this reason, the clinician typically programs the stimulation parameters in order to achieve a preferred balance of strong positive effects and minimal adverse side effects to create and effective therapy. Achieving such a balance would generally increase the complexity of programming, but the complexity may be minimized by guiding the clinician to effective stimulation programs that balance the positive and adverse effects according to the techniques of the invention.

During an evaluation session, the clinician begins by selecting an electrode configuration, such as by selecting a single electrode as a cathode in a unipolar configuration, and testing the stimulation therapy through multiple current or voltage amplitudes. For each program or parameter set, patient 12 rates one or more positive effects and the location of each effect and one or more adverse effects and the location of each effect. Programmer 32 stores the effect and/or rating information to sort the programs, e.g., during the evaluation session or after the evaluation session is completed. In some examples, the effect and/or rating information is stored in IMD 20 so that the information is always kept securely with patient 12. Programmer 32, or a different programmer or computing device, may then upload the information from IMD 20 when needed, e.g., at a subsequent visit, for programming of therapy. Programmer 32 may also automatically generate subsequent stimulation programs based upon the rating information. In this manner, programmer 32 may immediately eliminate certain programs without needing to test them, and direct the clinician to other possible programs that may be effective. In some embodiments, programmer 32 may generate bipolar electrode combinations for stimulation programs based upon the rating information if unipolar electrode combinations are deemed ineffective by patient 12. This guided programming technique will be further described in detail below.

Each electrodes 24, 26, 28 and 30 of leads 14 is a ring electrode that encircles the entire circumference or periphery of lead 14. The resulting stimulation field emanates radially from each electrode of lead 14, where lead 14 resides in the center of the stimulation field. In unipolar electrode combinations, one of electrodes 24, 26, 28 and 30 is set as the active electrode, or cathode, while the housing of IMD 20, or an electrode contact formed thereon, is the anode. In bipolar electrode combinations, two or more electrodes 24, 26, 28 and 30 are either a cathode or an anode. In some cases, the housing of IMD 20 may act as or include another anode in a bipolar combination. Unipolar and bipolar electrode combinations provide different stimulation fields to brain 18, and programmer 32 may generate electrode combinations for either type of stimulation. In alternative examples, simultaneous pulses or different amplitude may be applied to electrodes 24, 26, 28 and 30 of leads 14 in order to create partial electrode combinations as further possibilities for stimulation. These partial electrode combinations may be offered to the clinician in guided programming, for example, when unipolar and bipolar electrode combinations are not effective at treating patient 12, or when the clinician selects partial electrode combinations as a preference for a guided programming process.

In some embodiments, each of leads 14 may include more or less than four electrodes. For example, each of leads 14 may include eight electrodes, which may facilitate smaller sized stimulation fields or stimulating a larger volume tissue in brain 18. In some embodiments, one or more of leads 14 may include segmented electrodes.

A segmented electrode is actually two or more individual electrodes located around the circumference or periphery of a lead 14, such that a cross-sectional view of the lead 14 includes what looks like a ring electrode divided into segments. A segmented electrode array, in which electrodes are arranged at different axial positions along the lead and at different angular positions around the circumference or periphery of the lead, is an example of a complex electrode topology, in contrast to simple electrode array geometry, such as conventional ring electrodes on an axial lead, or electrodes arranged in rows on a paddle lead. Segmented leads may allow IMD 20 to provide many different stimulation field shapes or more directional stimulation to target certain anatomical regions while avoiding other anatomical regions.

Guided programming may also be used with leads 14 including segmented electrodes. In general, guided programming first activates all segments in the level for each of a plurality of levels of a lead 14, and then test different segment combinations at a selected one of the plurality of electrode levels. Programmer 32 may, for example, generate electrode combinations that target positively rated electrode levels and/or circumferential positions of lead 14 and eliminate the need to test levels and circumferential positions that produce negative effects for patient 12.

In alternative embodiments, leads 14 may not be straight with electrodes 24, 26, 28 and 30 axially aligned. Leads 14 may be curved or bent to produce different shapes. A different shape may be desirable for implantation at alternate anatomical sites within patient 12. For example, leads 14 may be curved in a semi-circle in order to place electrodes 24, 26, 28 and 30 adjacent to target anatomical regions of brain 18. Other examples of leads 14 include two or three dimensional arrays positioned across a paddle-like housing at the distal end of the leads 14. In any case, the shape, length, or other dimensions of leads 14 may be changed to target certain anatomical regions of patient 12.

In some embodiments, system 10 may include two leads 14 for bilateral stimulation of the brain. Certain DBS applications may necessitate treating both hemispheres of brain 18 to provide effective therapy. Each lead may be programmed with the same stimulation program or different stimulation programs, each tailored to the respective hemisphere of brain 18.

The guided programming technique provided by programmer 32 may be developed to duplicate the best practices and work flows that would be used by an experienced clinician or technical support expert. With practice, these types of people have developed programming routines that may efficiently produce effective stimulation therapy solutions for patients. Programmer 32 stores information that the guided programming process utilizes to imitate the knowledge and techniques commonly used by programming experts to find effective stimulation programs and solve programming difficulties. Guided programming may allow more clinicians to treat a greater number of patients while using less resources of the clinic and the manufacturer of IMD 20. In addition, the guided programming technique may be useful in generating programs that treat multiple locations within each hemisphere of brain 18, such as using two lead arrays within each hemisphere.

Programmer 32 may employ a predefined process or sequence of determining stimulation parameters used during the guided programming technique. For example, the electrode combination may change for each program according to certain rules. One sequence of electrode combinations may first screen unipolar electrode combinations, followed by bipolar electrode combinations, and followed further by tripolar combinations. Other sequences provided by programmer 32 may move back and forth between programs that include unipolar and bipolar electrode combinations as active electrodes move axially along the selected lead. In addition, other sequences of electrode combinations may be specified by the clinician according to common beneficial combinations.

In some cases, programmer 32 may incorporate logged beneficial effects and adverse effects in determining what electrode combination should be screened next. For example, one electrode combination may provide good beneficial effects with unwanted adverse effects. Programmer 32 may attempt to modify that specific electrode combination to keep the beneficial effects while reducing or eliminating the adverse effects noted by patient 12. Programmer 32 may automatically determine subsequent electrode combinations in this manner, or the programmer may suggest possible electrode combinations to the clinician which may keep the beneficial effects while reducing the adverse effects. In any case, guided programming techniques as described herein may be used with varying methods of determining subsequent stimulation parameters to try during the screening process.

After the evaluation session, programmer 32 presents a sorted listing or collection of the tested programs to the clinician. The tested programs may be sorted according to the positive effects rating, adverse effects rating, therapy window, and device longevity, as examples. While the positive effects rating and adverse effects rating are important in selecting the best program for therapy, the therapy window and device longevity may be factors important to long-term therapy success. The therapy window indicates the range of current or voltage amplitude that patient 12 tolerates, and may be characterized by a minimum therapeutic threshold and a maximum therapeutic threshold. More particularly, the therapy window may define an amplitude range from a minimum amplitude, at which positive effects are first noted, to a maximum amplitude, at which adverse effects of a threshold severity are first noted. A therapy window may additionally or alternatively indicate a range of pulse widths or pulse rates tolerated by the patient 12. Stimulation with amplitude, pulse width or pulse rate parameters outside of the therapy window may provide little or no efficacy or cause intolerable side effects.

Generally, the quality of stimulation is greater when a program has a larger therapy window. In addition, a larger therapy window provides greater flexibility for adjustment of the intensity of the therapy over time to account for changing symptoms or accommodation of patient 12 to the electrical stimulation. Programs with higher device longevity may consume less battery power in therapy, which may increase the amount of time patient 12 may use IMD 20 before a new IMD needs to be explanted. These factors may be increasingly important, especially when deciding between two or more substantially-equally effective stimulation programs.

The invention is not limited to systems used for delivery of DBS therapy or, for that matter, to any particular type of electrical stimulation. Other embodiments may deliver other types of neurostimulation therapy, such as cortical stimulation, spinal cord stimulation, peripheral nerve stimulation, facial or cranial nerve stimulation, or vagal nerve stimulation. Further, other embodiments may deliver other kinds of electrical stimulation, such as cardiac, gastric, pelvic, muscular, or functional stimulation. Although an IMD 20 is described for purposes of illustration, various embodiments of this disclosure also may be applicable to external stimulators that deliver stimulation to internal or external locations via implanted or external electrodes.

Figure 2:
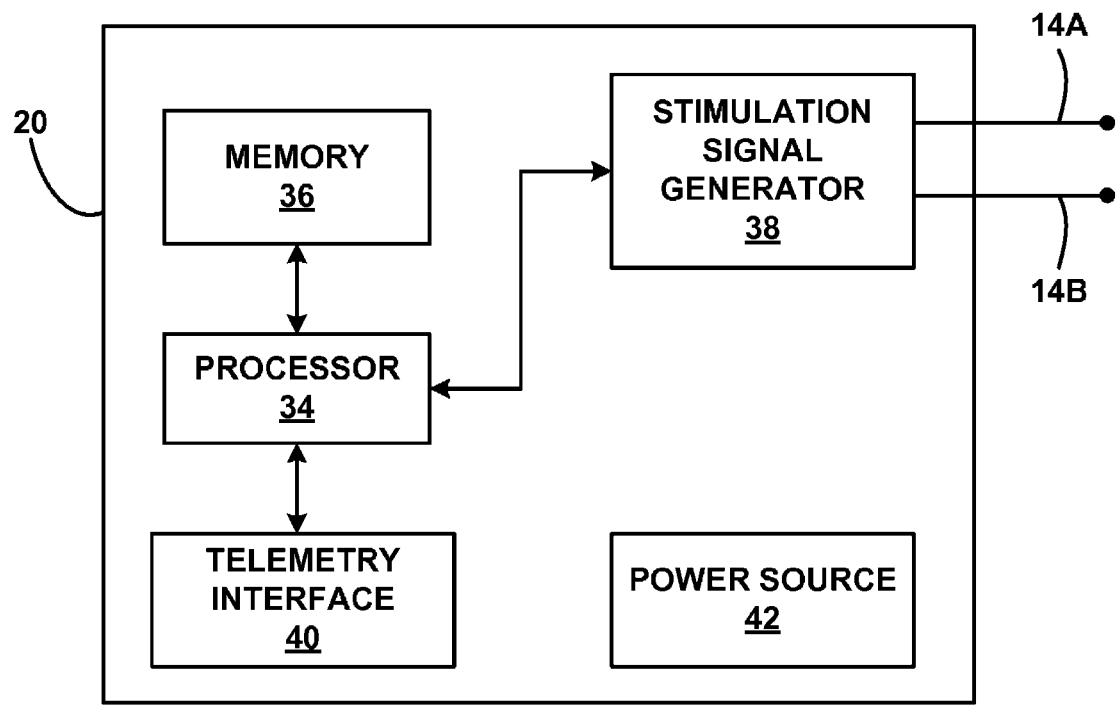
FIG. 2 is block diagram illustrating components of an example implantable medical device.

FIG. 2 is block diagram illustrating components of an example implantable medical device. In the example of FIG. 2, IMD 20 includes a processor 34, memory 36, stimulation signal generator 38, telemetry interface 40, and power source 42. As shown in FIG. 2, stimulation signal generator 38 is coupled to leads 14 (which include electrodes 24, 26, 28 and 30, as discussed above). Alternatively, stimulation signal generator 38 may be coupled to a different number of leads as needed or desired to provide stimulation therapy to patient 12.

Processor 34 controls stimulation signal generator 38 to deliver electrical stimulation therapy according to programs stored in memory 36 and/or received from programmer 32 via telemetry interface 40. As an example, a new program received from programmer 32, which may be a test or chronic program, may modify the electrode configuration and amplitude of stimulation, and in some cases other parameters such as pulse width and pulse rate. Processor 34 may communicate with stimulation signal generator 38 to change the electrode configuration used during the therapy and modify the amplitude of stimulation. Processor 34 may then store these values in memory 36 to continue providing stimulation according to the new program until instructed otherwise. Processor 34 may stop the previous program before starting the new stimulation program as received from programmer 32. In some embodiments, amplitude (current or voltage) of the stimulation pulses may be ramped down or ramped up as a program is being turned off or turned on. In this manner, no abrupt stimulation changes may be perceived by patient 12. A ramp up of the new program may provide patient 12 time to stop stimulation if the new program is uncomfortable or even painful.

Processor 34 may comprise any one or more of a microprocessor, digital signal processor (DSP), application specific integrated circuit (ASIC), field-programmable gate array (FPGA), or other digital logic circuitry. Memory 36 stores instructions for execution by processor 34, e.g., instructions that when executed by processor 34 cause the processor and IMD to provide the functionality ascribed to them herein, as well as stimulation programs. In some examples, the effect and/or rating information, stored in memory 36 of IMD 20 so that the information is always kept securely with patient 12. Memory 36 may include any one or more of a random access memory (RAM), read-only memory (ROM), electronically-erasable programmable ROM (EEPROM), flash memory, or the like.

Stimulation signal generator 38 may provide stimulation in the form of pulses to patient 12. IMD 20 may further include a switch device (not shown) to couple pulses, generated by signal generator 38 to selected electrodes via various conductors within the implantable leads 14. Stimulation parameters for each stimulation program may include electrode configuration or combination (including selected electrodes and polarities), current or voltage amplitude, pulse width, pulse rate, and/or duty cycle. Other parameters may be used depending on the therapy to be provided to patient 12. Stimulation signal generator 38 may independently utilize any electrodes on leads 14. In this manner, stimulation signal generator 38 may be utilized to deliver stimulation via numerous different electrode configurations to provide therapy for a wide variety of patient conditions.

Telemetry interface 40 may include circuitry known in the art for facilitating wireless telemetry, e.g., via radio frequency (RF) communication or proximal inductive interaction with similar circuitry within external programmer 32. Power source 42 delivers operating power to the components of IMD 20. Power source 42 may include a battery and a power generation circuit to produce the operating power. In some embodiments, the battery may be rechargeable to allow extended operation. Recharging may be accomplished through proximal inductive interaction between an external charger and an inductive charging coil within IMD 20. In other embodiments, non-rechargeable batteries may be used.

As a further alternative, an external power supply could transcutaneously power IMD 20 whenever stimulation is needed or desired.

Figure 3:
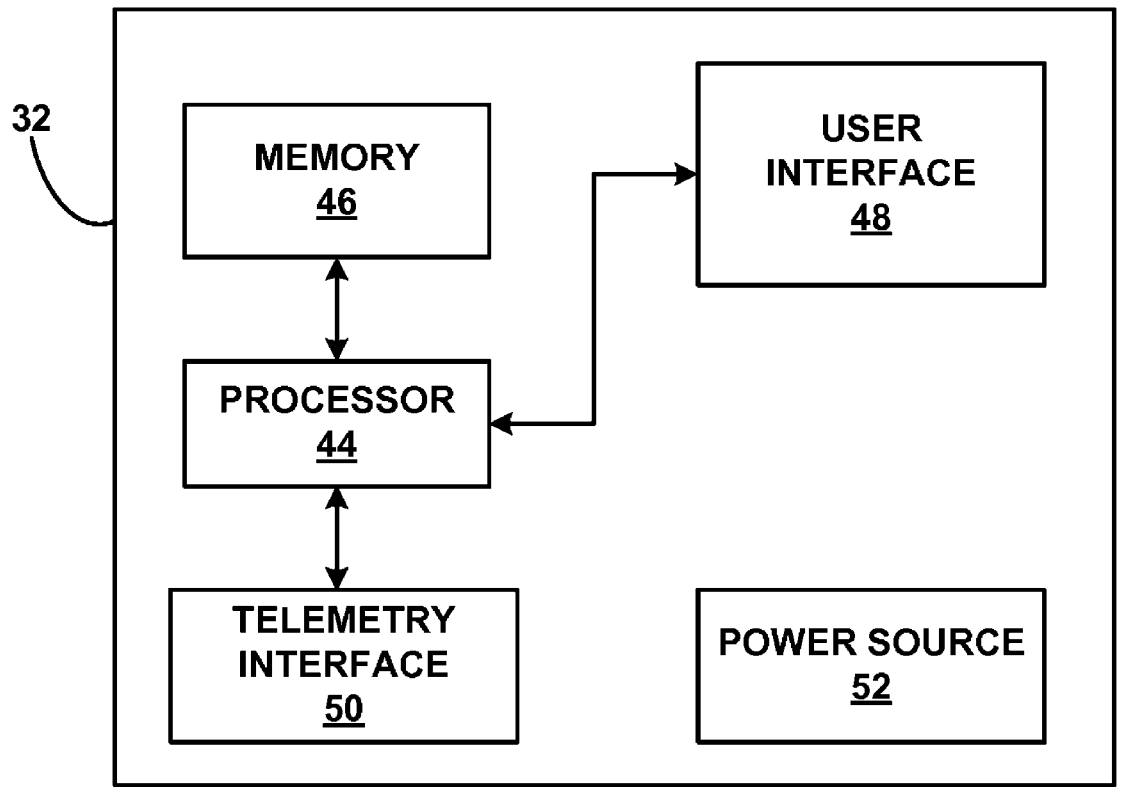
FIG. 3 is block diagram illustrating components of an example external programmer.

FIG. 3 is block diagram illustrating components of an example external programmer. As shown in FIG. 3, external programmer 32 includes processor 44, memory 46, user interface 48, telemetry interface 50, and power source 52. Programmer 32 may be used to select stimulation programs, generate new stimulation programs, sort tested programs, receive positive and negative input, and transmit the selected programs to IMD 20. As described herein, programmer 32 may guide a clinician through programming to identify efficacious stimulation programs. For example, as described herein, processor 44 may apply guiding rules stored in memory 46 to evaluated programs in order to generate subsequent programs for evaluation. Processor 44 controls user interface 48 to receive positive and negative input from the clinician and present sorted tested programs to the clinician. Processor 44 may also send selected programs to IMD 20 via telemetry interface 50 to control stimulation automatically and/or as directed by the clinician.

Programmer 32 may be a patient programmer or a clinician programmer. A clinician programmer may include more functionality than the patient programmer. For example, a clinician programmer may include a more fully featured user interface, allow a clinician to download IMD usage and status information from IMD 20, and allow a clinician to control aspects of IMD 20 not accessible by a patient programmer. In some embodiments, a patient programmer may also be limited as to what programs, if any, can be generated without the aid of a clinician.

A user, either a clinician or patient 12, may interact with processor 44 through user interface 48. User interface 48 may include a display, such as a liquid crystal display (LCD), light-emitting diode (LED) display, or other screen, to show information related to stimulation therapy, and buttons or a pad to provide input to programmer 32. Buttons may include an on/off switch, plus and minus buttons to increase and decrease parameter values or navigate through options, a select button to pick or store an input, or other buttons as needed to modify stimulation. Other input devices may be a wheel to scroll through options or a touch pad to move a pointing device on the display. In the preferred embodiment, the display is a touch screen that enables the clinician to select options directly from the display screen.

The display may be a monochrome or full color display. The display may also be backlit to enable operation in a low-light environment. Items displayed on the display during therapy may include the program currently being used, current or voltage amplitude, battery status, and rating information. The display also provides one or more screens that guide the clinician through programming of IMD 20. A screen may allow the clinician to select a particular electrode, adjust the current or voltage amplitude to be tested, give a positive or negative input, and select one or more preferred programs for stimulation therapy. The clinician may also view a presented summary of a selected program and an end session summary of the guided programming period.

The display may include separate screens for each of the positive effects and the adverse effects. The clinician may input specific positive or adverse effects that occur at a specific location of patient 12. The input may be in the form of a numerical system, drop-down menus, anatomical icons, effect icons, written descriptions, or any other input mechanisms. In some embodiments, the clinician may even speak to programmer 32 to provide the positive and negative input rating positive and adverse effects, respectively. In other embodiments, programmer 32 may provide audio information in addition to, or in place of, a visual display.

Memory 46 may include instructions for operating user interface 48, telemetry interface 44 and managing power source 52. Memory 46 also includes instructions, or guiding rules, for generating stimulation programs based upon the effect/and or rating information. These instructions may include a look up table, rating map, or other equations that may be applied to the previously tested program, or first program, to generate a second program for evaluation. In addition, processor 44 may store all tested programs and avoided programs during one or more programming sessions, in memory 46. In this manner, processor 44 may be prevented from generating duplicate programs not needed for evaluation.

Memory 46 may store program instructions that, when executed by processor 44, cause programmer 32 to provide the functionality ascribed to them herein. Memory 46 may include any one or more of a random access memory (RAM), read-only memory (ROM), electronically-erasable programmable ROM (EEPROM), flash memory, or the like. Processor 44 may comprise any one or more of a microprocessor, digital signal processor (DSP), application specific integrated circuit (ASIC), field-programmable gate array (FPGA), or other digital logic circuitry.

Wireless telemetry in programmer 32 may be accomplished by radio frequency (RF) communication or proximal inductive interaction of external programmer 32 with IMD 20. This wireless communication is possible through the use of telemetry interface 50. Accordingly, telemetry interface 50 may include circuitry known in the art for such communication.

Power source 52 delivers operating power to the components of implantable programmer 32. Power source 52 may include a battery and a power generation circuit to produce the operating power. In some embodiments, the battery may be rechargeable to allow extended operation. Recharging may be accomplished through proximal inductive interaction, or electrical contact with circuitry of a base or recharging station. In other embodiments, primary batteries may be used. In addition, programmer 32 may be directly coupled to an alternating current source.

Figure 4:
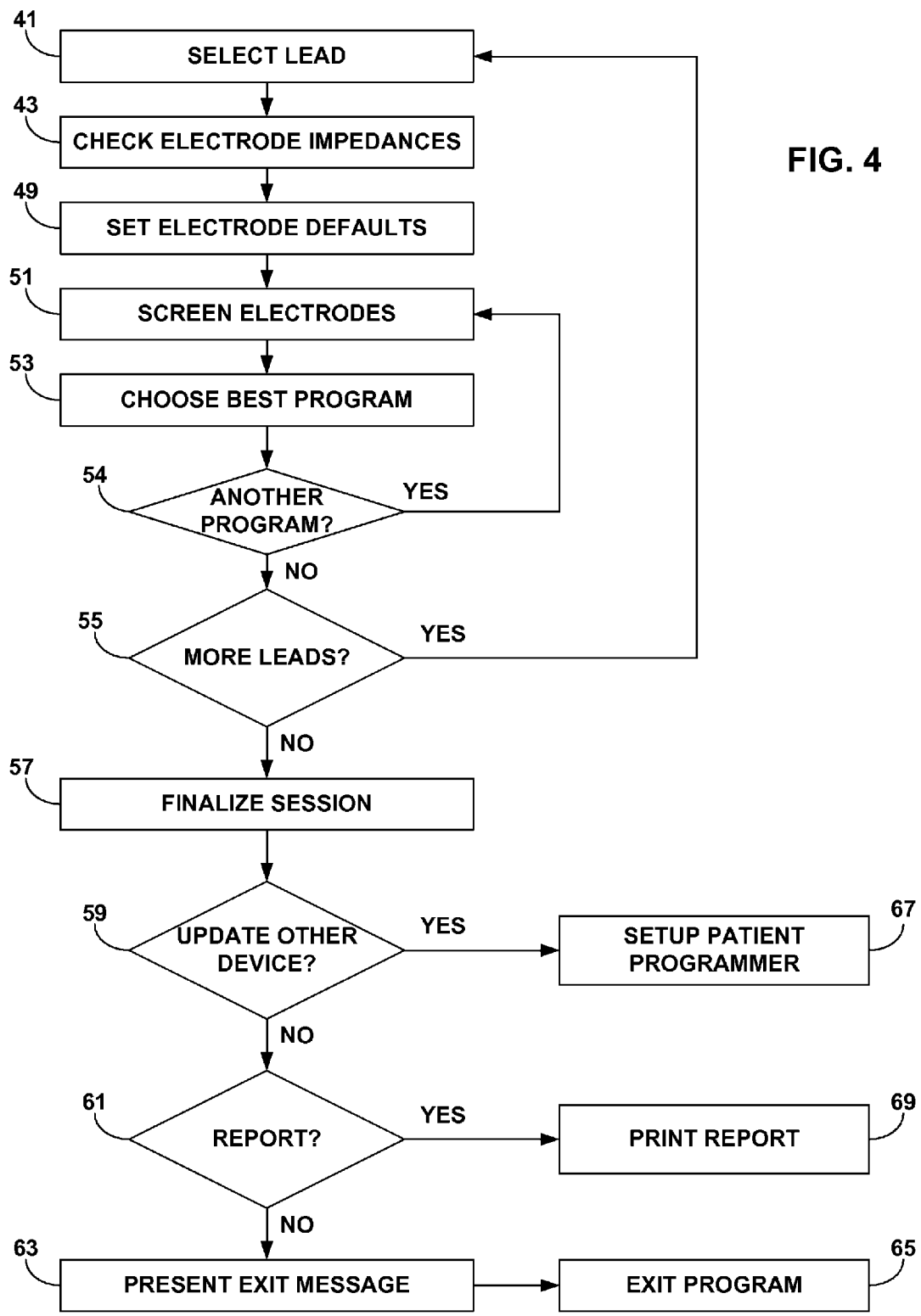
FIG. 4 is a flow diagram illustrating a general example technique for guiding a clinician through programming stimulation therapy.

FIG. 4 is a flow diagram illustrating a general example technique for guiding a clinician through programming stimulation therapy. As shown in FIG. 4, guided programming may support clinicians who are novice or infrequent programmers as they work through a recently implanted IMD 20 or leads 14 in patient 12. In addition, guided programming may support clinicians when leads 14 have complicated electrode combination possibilities, such as a complex electrode array geometry. Specifically, the guided programming may be useful during the initial programming session. The clinician may not lose any testing history, i.e. screening history, if guided programming is closed before a selection of a program is made. Guided programming may, or may not, support the generation of multiple programs. The technique of FIG. 4 is an overview of an example guided programming method, which is further described in detail in FIGS. 5-7.

As shown in FIG. 4, the clinician selects a lead (41) and checks the impedance of the lead (43). In some embodiments, IMD 20 may be coupled to only a single lead. In other embodiments, IMD 20 may be coupled to two or more leads, such as leads 14A and 14B.

The clinician then sets the stimulation parameter, e.g., electrode, defaults for guided programming on the selected lead (49). The clinician may stop, or mute, stimulation on another lead not being tested to isolate the selected lead being tested. Stimulation on the other lead or leads may be resumed once testing on the selected lead is completed.

Figure 6:
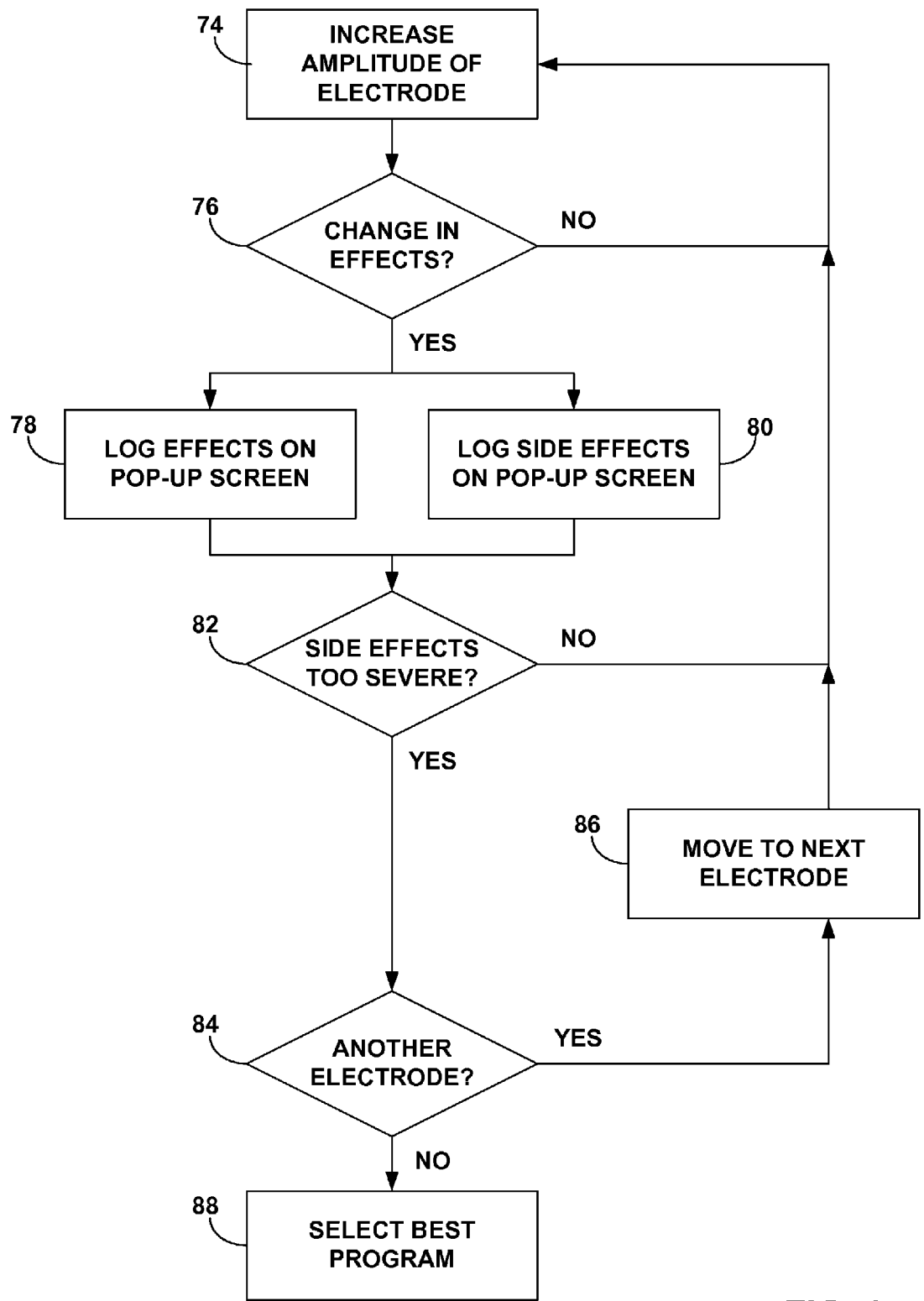
FIG. 6 is a flow diagram illustrating an example technique for recording effects and side effects during guided programming.
Figure 7:
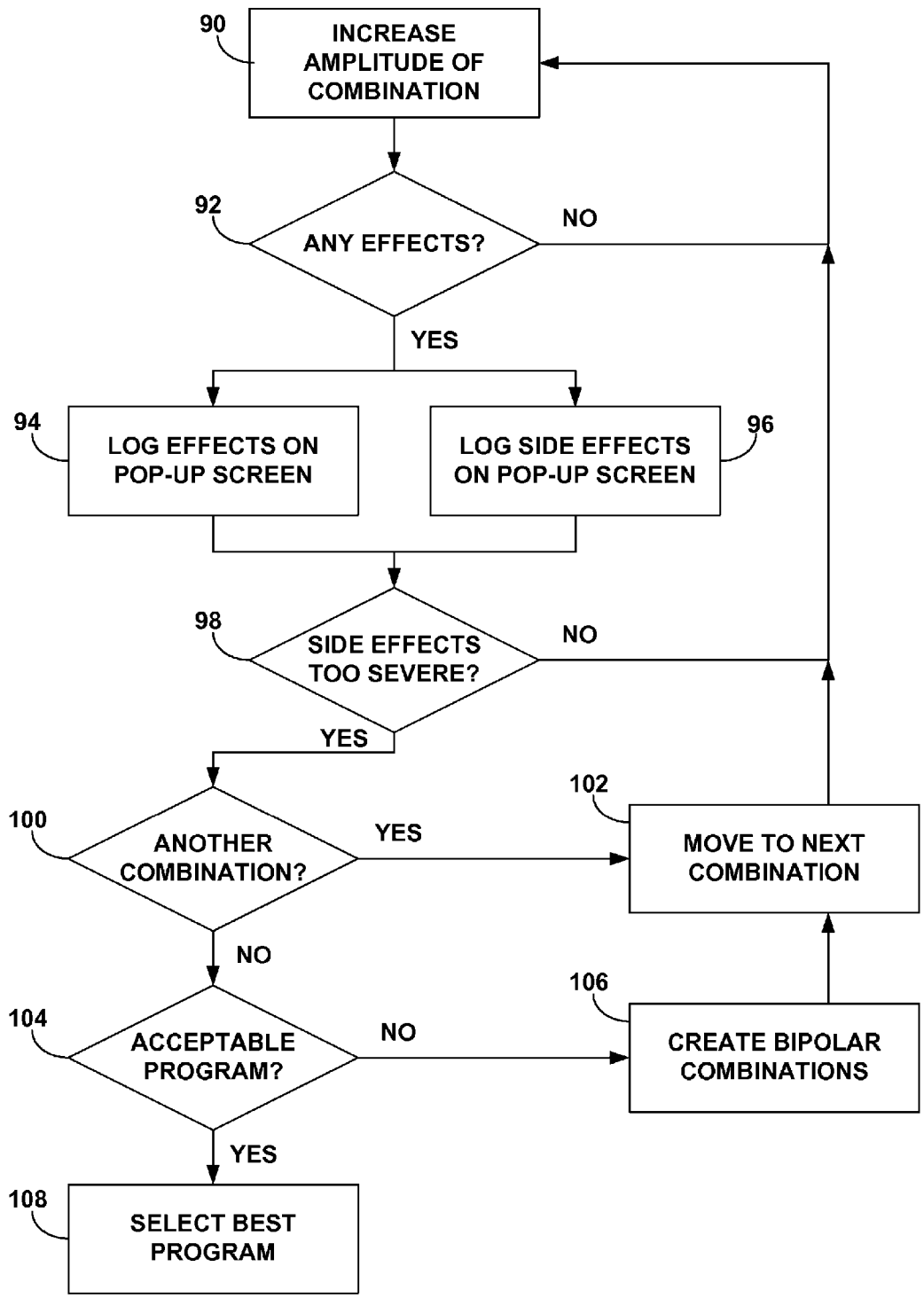
FIG. 7 is a flow diagram illustrating an example technique for recording effects and side effects during guided programming and providing new electrode configurations if needed.

The clinician then begins the process of screening selected electrodes and logging the effects of the test stimulation from each electrode on the selected lead (51), described in more detail in FIGS. 6-7. For example, the clinician selects an electrode, and increases the amplitude of the stimulation iteratively while logging positive effects and adverse effects on the patient. The amplitude increases iteratively until effects are noticed by patient 12 or the clinician. The effects, both good effects and side effects, are then logged. If the adverse effects are not too severe to continue, the amplitude increases are continued. If the adverse effects are too severe, however, and more electrodes are available for evaluation, another electrode is selected and the process is repeated. In the evaluation process, each electrode may be evaluated as a unipole in combination with an electrode associated with the housing of the IMD 20. In some cases, bipolar electrode combinations may also be screened during the processes if unipolar electrodes do not effectively treat patient 12.

Once the clinician does not have more electrode combinations to test for the selected lead, the clinician selects either the best program or one or more of the best programs from a sorted list provided by programmer 32 (53). If the clinician desires to select another program for the lead (54), the clinician may return to screen the electrodes once again (51). If the clinician has more leads to test (55), the clinician begins again by selecting a lead (41). If the clinician does not have more leads to test, the clinician is guided to finalize the end of the session (57). If the clinician desires to update another device (59), the clinician may then setup a patient programmer (67). Setting up a patient programmer may include populating the patient programmer with the one or more programs selected after the guided programming process and may include storing screening history in the patient programmer for future reference of patient 12 or the clinician. In addition, if the clinician desires to print a report of the guided programming session (61), the clinician may print the report for further review or clinic records (69). The report may include identified electrodes not functioning properly, screening history, the chosen program for therapy, and other information created during the guided programming session. Programmer 32 may then present an exit message (63) and exit the guided programming session (65). Aspects of this guided programming process are described in greater detail with respect to the following Figures.

Figure 5:
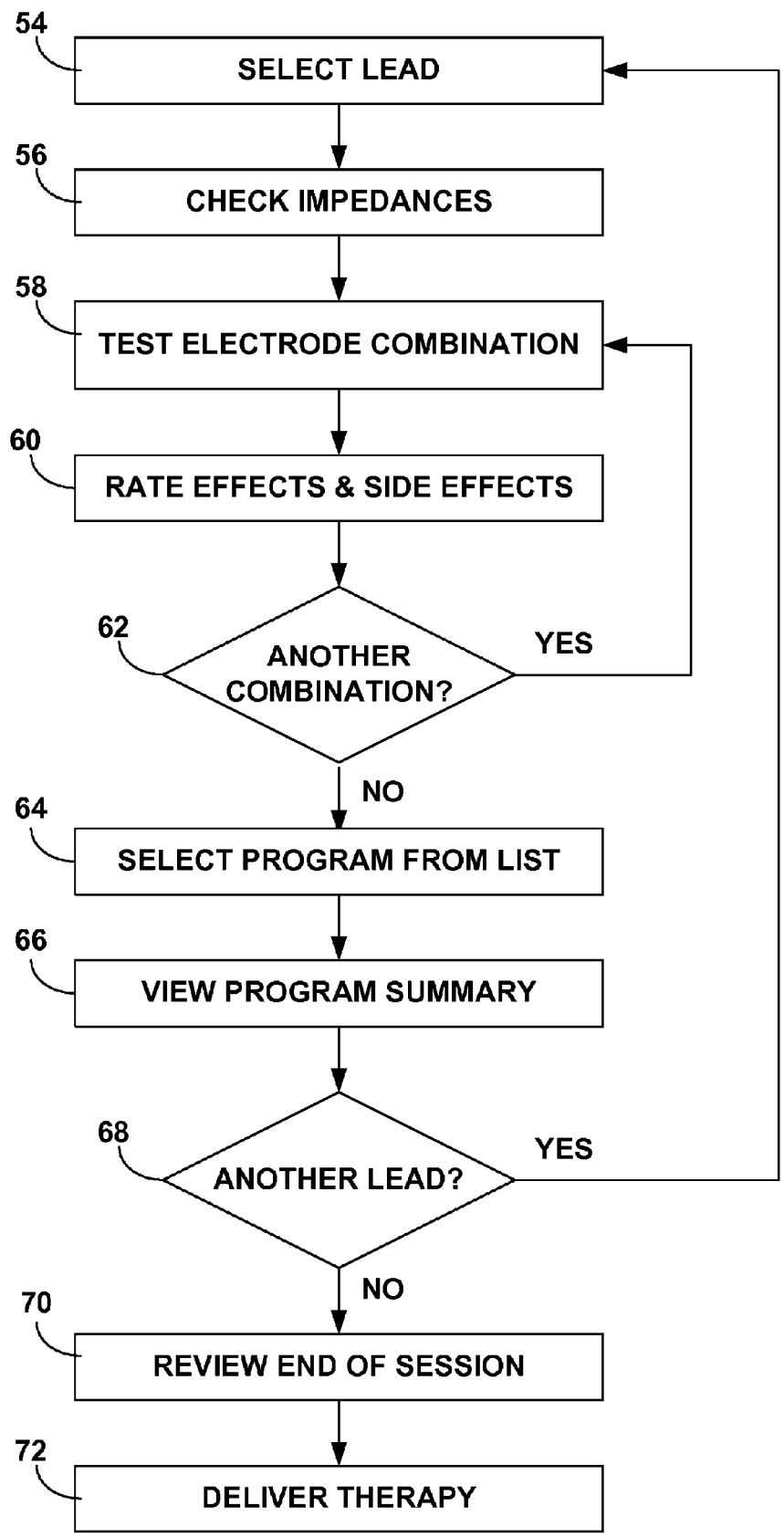
FIG. 5 is a flow diagram illustrating a detailed example technique for guided programming.

FIG. 5 is a flow diagram illustrating a detailed example technique for guided programming. FIG. 5 illustrates the aspects of the guided programming process of FIG. 4 in greater detail. As shown in FIG. 5, the clinician begins programming IMD 20 by selecting the desired lead 14 (54). The clinician next checks the impedances of lead 14 to identify any malfunction before testing stimulation programs (56). Checking leads may be iterative, and programmer 32 may provide feedback to the clinician as to how to fix or otherwise address any identified problems, such as electrical continuity issues. Iterative checking of lead impedances may be completed according to the disclosure of commonly-assigned U.S. patent application Ser. No. 11/590,741, to Goetz et al., which was filed on Oct. 31, 2006, and is incorporated herein in its entirety by reference.

The clinician continues the process by initially testing an electrode combination, which is part of a first program (58). In some cases, as mentioned above, the first electrode combination is a unipolar combination including an electrode on the lead and an electrode on the IMD housing. After stimulation is provided using the first program, the clinician rates the positive effects and the adverse effects according to feedback from patient 12 (60). After the tested program is evaluated, programmer 32 prompts the clinician if another electrode combination is desired to be tested (62). In some embodiments, programmer 32 may automatically decide to test another program based upon the rating information of the first program. If another program is to be tested, programmer 32 generates a new program, which may include a new electrode combination, and the second program is tested (58). If no other program is to be tested, programmer 32 sorts and displays a list of tested programs to the clinician.

Either programmer 32 or the clinician determines the electrode combination and other stimulation parameters of the next program that is to be tested. In some embodiments, programmer 32 may systematically determine more programs for testing. Programmer 32 may first provide a static list of common programs used for therapy with corresponding stimulation parameters. Once the list of common programs is exhausted and the clinician desires additional programs to test, programmer 32 may extend the list by providing additional unipolar electrode combinations. If further programs are desired, programmer 32 may create bipolar electrode combinations for programs that the clinician may test.

Alternatively, programmer 32 may utilize branch dynamics to create additional programs to test. Programmer 32 may incorporate electrode combinations with some benefits or switch some common unipolar electrode combinations to similar bipolar electrode combinations before trying additional unipolar electrode combinations. In any case, programmer 32 may follow predefined rules when populating potential program lists with additional programs for the clinician to test.

The clinician selects one of the tested programs from the sorted list (64). This selected program may be considered the preferred program and located near the top of the sorted list. The clinician may then view the program summary for lead 14 (66). If the clinician desires to find a program for another lead (68), programmer 32 again prompts the clinician to select which lead to test (54). If no other lead should be tested, programmer 32 presents a review of the end of session to the clinician (70). At this time, the clinician may store the selected program and/or transmit the selected program to IMD 20 and begin delivering therapy according to the program (72).

In some embodiments, programmer 32 may automatically perform steps of the above-described process without waiting for clinician input. For example, programmer 32 may require the clinician to select at least one program for each lead programmable by the programmer. In alternative embodiments, programmer 32 may automatically select the preferred program based upon the rating information to decrease the programming time. However, some clinicians may desire to review the evaluated programs before determining which program to use for therapy.

FIG. 6 is a flow diagram illustrating an example technique for recording effects and side effects during the screening portion of guided programming. FIG. 6 provides details for steps 58-64 of FIG. 5 according to some embodiments. After selecting an electrode combination, or program, to evaluate, programmer 32 directs IMD 20 to increase the amplitude of the stimulation delivered via the selected electrode combination (74). If patient 12 does not notice any change in effects from stimulation, positive or negative, programmer 32 increases the amplitude again (76). If patient 12 does perceive an effect from the stimulation, the logs any positive therapeutic effects on the effects pop-up screen (78). The clinician may also log any adverse (negative) side effects on the adverse effects pop-up screen (80). The clinician may be prompted to log effects after each amplitude increase.

For a DBS application, examples of positive effects include relief of symptoms of a disorder or disease, such as Hutchinson's Disease, Parkinson's Disease, or movement disorders. Examples of adverse side effects include incontinence, tingling, loss of balance, paralysis, slurred speech, loss of memory, and other neurological problems. Other types of positive and adverse effects may be applicable for different types of stimulation, such as SCS, gastric stimulation or pelvic floor stimulation. While both pop-up screens may be presented simultaneously, they may be presented to the clinician one at a time.

After the clinician has provided positive and/or negative input, clinician decides if the adverse effects are too severe to continue based upon the rating information (82). In some examples, programmer 32 may decide if the adverse effects are too great to continue. If the adverse effects are not too severe, programmer 32 again increases the amplitude (74). If the adverse effects are too severe to continue, programmer 32 determines if another electrode combination should be tested (84). In some cases, the clinician may decide if another electrode combination should be tested. If another electrode combination is to be tested, programmer 32 generates the next electrode combination based upon the rating information of the previous electrode combination and moves to the new electrode combination (86). Programmer 32 increases the amplitude of the new program, e.g., electrode combination (74) and the evaluation of programs continue.

The generation of new programs, including new electrode combinations, utilizes the guiding rules stored in memory 46 of programmer 32. One or more rules may be associated with each positive and negative effect, as well as each location of patient 12. For example, if electrode 30A of lead 14A is tested and patient 12 indicates extreme slurring of speech and blurred vision in the negative input, programmer 32 may immediately stop using electrode 30A in any programs and move to another electrode, such as electrode 28A of lead 14A. A greater positive input may generally cause programmer 32 to keep using the same electrode while a greater negative input may generally cause programmer 32 to use electrodes further from the electrode producing adverse effects.

If there are no more electrode combinations to test, programmer 32 sorts the tested programs according to the rating information and allows the clinician to select the best program for therapy (88). In other embodiments, programmer 32 may automatically determine the best program based upon the effects and/or rating information. When determining the best program overall, programmer 32 may use a weighted sum for a plurality of types of effect. For example, tremor may be weighted greater than gait impairment so that limiting tremor is more important than limiting gait impairment. Further, in some embodiments positive and negative effects may be positive and negative numbers in the weighted sum. The weighting system may be predetermined in programmer 32 for each type of IMD 20, therapy, clinician, or combined medication taken by patient 12. Alternatively, the weighting system may be customized by the clinician or user based upon desired therapy outcomes or programming experience. In addition to positive and negative effects, the therapy window and device longevity may be used as factors in selecting the best program for therapy. For example, a larger therapy window may be desirable. In additional embodiments, two or more programs may be selected such that patient 12 may have multiple choices in stimulation programs throughout the therapy.

FIG. 7 is a flow diagram illustrating an example technique for recording positive effects and negative side effects during the screening portion of guided programming, and providing new electrode configurations if needed. As shown in FIG. 7, details to steps 58-64 of FIG. 5 are provided with the ability to generate bipolar electrode combinations. After selecting a unipolar electrode combination, e.g., a program including a unipolar electrode combination, to evaluate, programmer 32 directs IMD 20 to increase the amplitude of the stimulation (90) delivered via the selected combination. If patient 12 does not notice any effects, positive or negative, programmer 32 increases the amplitude again (92). If patient 12 does perceive an effect from the stimulation, the clinician logs any positive effects on the effects pop-up screen (94). The clinician also logs any adverse side effects on the adverse effects pop-up screen (96). Again, the clinician may be prompted to log effects after the amplitude increases, or may select an effect logging option when the patient notes positive or negative effects. Furthermore, while both pop-up screens may be presented simultaneously, they may be presented to the clinician one at a time.

After the clinician has provided positive and negative input, programmer 32 decides if the adverse effects are too severe to continue based upon the rating information (98). If the adverse effects are not too severe, programmer 32 again increases the amplitude (90). If the adverse effects are too severe to continue, programmer 32 determines if another electrode combination should be tested (100). In some cases, the clinician may decide if another electrode combination should be tested. If another electrode combination is to be tested, programmer 32 generates the next electrode combination based upon the rating information of the previous electrode combination, and directs the IMD to move to the new electrodes (102). Programmer 32 increases the amplitude of the new program (90) and the evaluation of programs continues.

If there is no additional unipolar electrode combination to test (100), programmer 32 or the clinician determines if the current best program is acceptable based upon the rating information (104). If the current best program is acceptable, the clinician is prompted to select the best program for stimulation therapy (108). If none of the unipolar programs are acceptable (104), programmer 106 uses rating information from the tested unipolar electrode combinations to generate possible bipolar electrode combinations (106). Programmer 32 moves to the next bipolar electrode combination (102) and increases the amplitude of the program (90).

The generation of new programs, including electrode combinations, utilizes the guiding rules stored in memory 46 of programmer 32. The rules for unipolar electrode configuring may be different from the rules for bipolar electrode configuring. One or more rules may be associated with each positive and negative effect, as well as each location of patient 12. For example, if electrode 26A and 28A of lead 14A are tested and patient 12 indicates extreme blurred vision in the negative input, programmer 32 may immediately stop using electrode 26A and move to use electrodes 28A and 30A of lead 14A in a bipolar configuration. A greater positive input may generally cause programmer 32 to keep using the same electrodes while a greater negative input may generally cause programmer 32 to use electrodes further from the electrode producing adverse effects. The guiding rules may also determine which electrodes are cathodes and anodes, including the housing of IMD 20.

Once programmer 32 has at least one acceptable program for therapy (104), programmer 32 prompts the clinician to select the best program. In other embodiments, programmer 32 may automatically determine the best program based upon the rating information. Additionally, the therapy window and device longevity may be used as factors in selecting the best program for therapy. In additional embodiments, two or more programs may be selected such that patient 12 may have multiple choices in stimulation programs throughout the therapy.

FIGS. 8A-8C are flow diagrams illustrating possible sorting techniques for evaluated electrode combinations, e.g., programs, during programming. As shown in FIG. 8A, programmer 32 follows a hierarchy of importance when sorting tested programs. Positive effects 110 are generally the most important rating because it indicates which tested program alleviates the condition of patient 12. Therefore, programmer 32 first sorts the tested programs according to positive effects 110. Next, adverse effects 112 are important because they can decrease the quality of life of patient 12, even if the original condition is being treated. Within the tested programs sorted for positive effects 110, the tested programs of substantially the same positive effects are sorted according to each program's adverse effects as rated by patient 12.

Sorting the tested programs by the therapy window and device longevity is a further refinement to separate programs rated substantially equally with respect to positive effects 110 and negative effects 112. In this case, therapy window 114 and device longevity 116 are deemed equally important. Therefore, the programs are simply sorted by one or the other, as requested by the clinician or preset in programmer 32.

FIGS. 8B and 8C are examples of the sorting hierarchy when all four ratings are used to sort the tested programs. In the example of FIG. 8B, tested programs are sorted first by positive effects 110, second by adverse effects 112, third by therapy window 114, and last by device longevity 116. The top sorted tested program would have the best positive effects 110, the least adverse effects 112 of the top positive effect programs, the largest therapy window 114 of the least adverse effects 112 group, and the longest device longevity 116 of the remaining tested programs. In this manner, a tested program may have the least adverse effects 112, but it will not be sorted at the top if another tested program has better rated positive effects 110.

FIG. 8C is very similar to the example of sorting described in FIG. 8B; however, device longevity 116 is given more weight during the sorting process than the size of therapy window 114. In other embodiments, more or less criteria may be used when sorting tested programs. For example, each different positive effect may be weighted differently according to the guiding rules stored in memory 46.

FIGS. 9-40 are conceptual diagrams of example graphical user interfaces (GUIs) that may be provided by programmer 32 using a guided programming technique according to the invention. All graphical user interfaces may be provided by processor 44 via user interface 48 of external programmer 32, e.g., a display of the user interface. In these examples, the GUIs utilize touch screen interfaces, and other buttons and/or input mechanisms of programmer 32 may be used.

In some examples, programmer 32 may provide additional GUIs to the clinician before guided programming begins. These additional GUIs may allow the clinician to select a type of IMD 20 that will be programmed and the type of therapy desired (e.g., deep brain stimulation). Forcing the clinician to follow a certain work flow may decrease programming time and increase guided programming efficacy in generating the best program for therapy. In this manner, programmer 32 may use this information to provide guided programming directed to the specific therapy for patient 12.

Figures 9, 10:
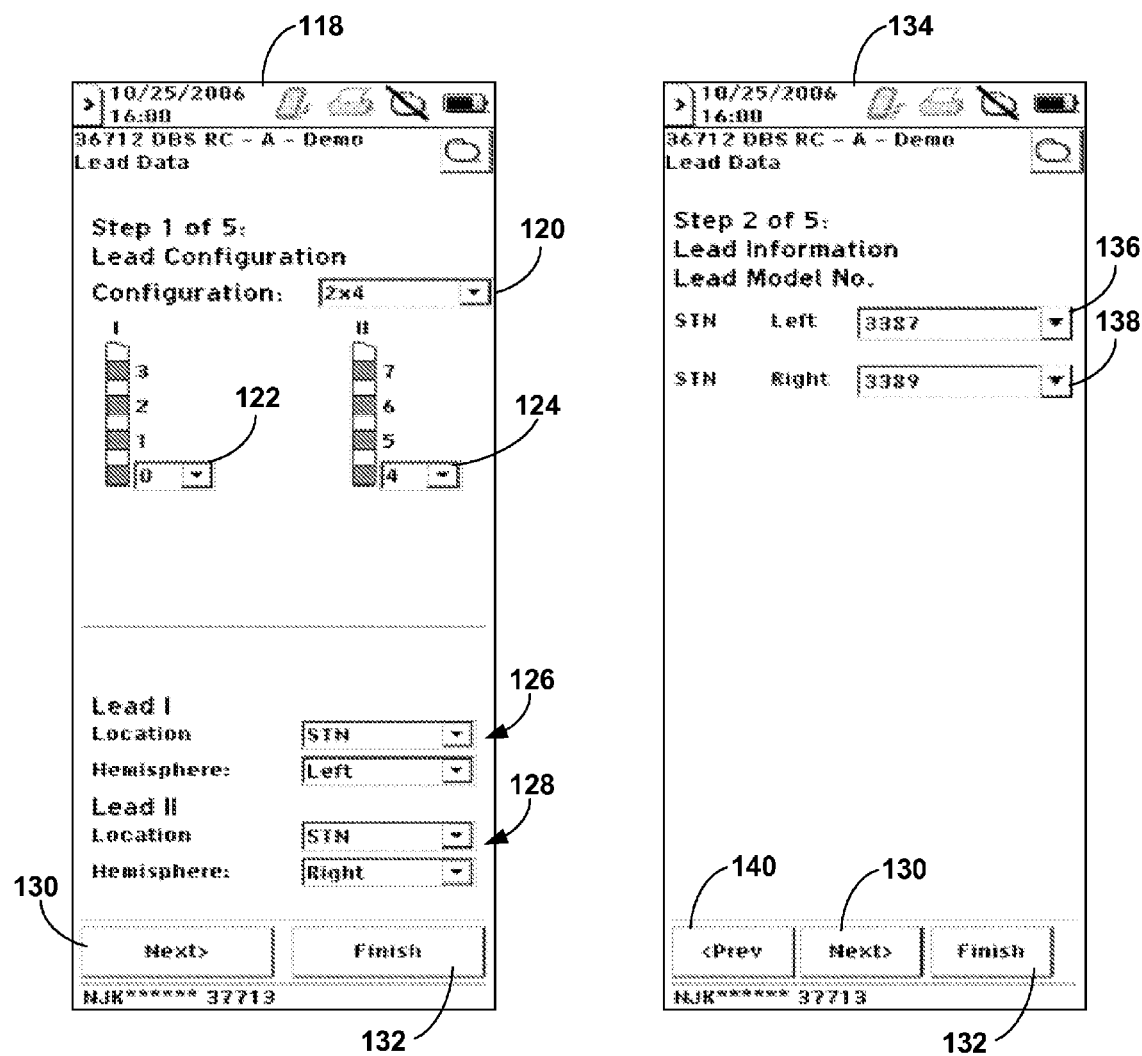

FIGS. 9-13 are example screen shots illustrating initial steps for an example guided programming process, the steps including collection of lead configuration and therapy information. Information provided by the clinician in the GUIs of FIGS. 9-13 may be stored in IMD 20 so that patient 12 specific data always remains with the patient for retrieval by any programmer 32. As shown in FIG. 9, GUI 118 presents the first of five steps in setting up system 10 for patient 12. GUI 118 includes lead configuration 120, first lead assignment 122, second lead assignment 124, first lead location 126 and second lead location 128. GUI 118 also includes next button 130 and finish button 132. The clinician selects the type of lead configuration 120 implanted in patient 12, such as two leads 14 with four electrodes 24, 26, 28 and 30 on each electrode (2×4). However, other lead configuration options may include a single lead, more than two leads, or leads with varying number of electrodes. The clinician may also assign a number to each electrode with the pull down menus of first lead assignment 122 and second lead assignment 124. In addition, the clinician provides the implanted location of each lead 14 with the specific location drop down menu and hemisphere indication drop down menu of first lead location 126 and second lead location 128. As indicated in FIG. 9, leads 14 are implanted in the subthalamic nucleus (STN) in each of the right and left hemisphere of brain 18. The clinician may move to step two of the guided programming process by selecting next button 130. Upon selecting finish button 132, any information entered by the clinician may be transmitted to IMD 20 for long term storage.

FIG. 10 illustrates example GUI 134 that presents a second step of the setup of system 10. GUI 134 includes lead model menu 136 and lead model menu 138. Lead model menu 136 includes all supported types of leads, one of which is selected by the clinician as the type of lead that has been implanted in the left hemisphere of brain 18. Similarly, lead model menu 138 includes all supported types of leads, one of which is selected as the lead type implanted in the right hemisphere. As indicated, leads 14 implanted in brain 18 may be of different types or models. The clinician can move back to step one (GUI 118) with previous button 140 or move forward to step three by selecting next button 130. Upon selecting finish button 132, any information entered by the clinician may be transmitted to IMD 20 for long term storage.

Figures 11, 12:
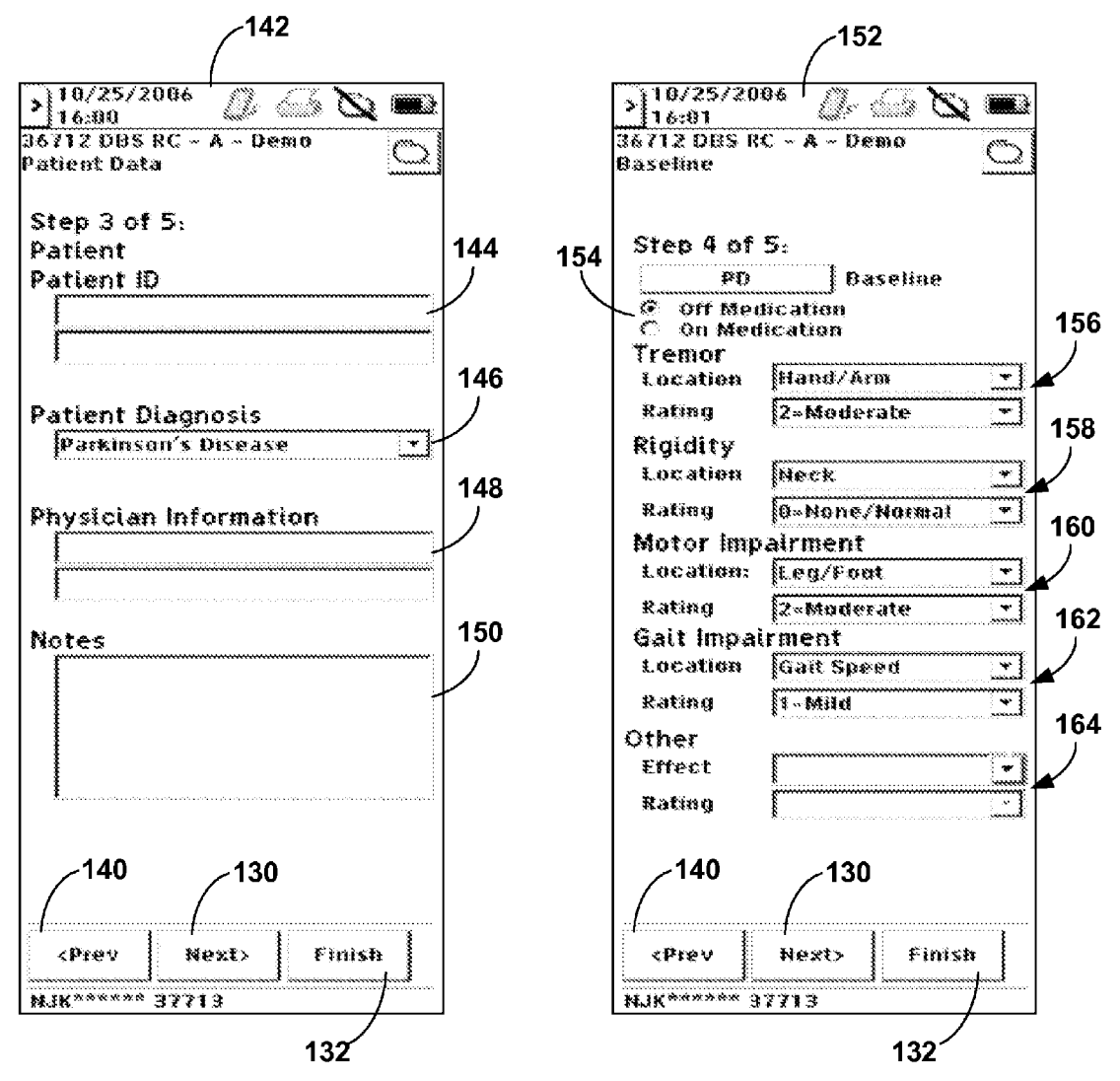

As shown in FIG. 11, GUI 142 presents patient ID field 144, diagnosis menu 146, physician field 148, and notes field 150 in the third step of system 10 setup. The clinician may enter patient information such as the patient's name and clinic patient number into patient ID field 144. The clinician may also enter the current diagnosis targeted for therapy by selecting the condition of the patient from the drop down menu diagnosis menu 146. In addition, the clinician may enter the information identifying the physician, or clinician, treating patient 12 with physician field 148. In some cases, the clinician may desire to add other specific information relating to the treatment or condition of patient 12 in notes field 150. The clinician may navigate to other screens of GUIs by selecting previous button 140, next button 130, or finish button 132.

FIG. 12 illustrates an example of the fourth step of system 10 setup. GUI 152 allows a clinician to enter further details of the condition of patient 12 prior to testing or programming stimulation therapy. These details include medication selection 154, tremor menus 156, rigidity menus 158, motor impairment 160, gait impairment 162, and other symptom or condition input 164. Each of fields 156-164 includes elements for entry of the location and severity of the symptom. In some embodiments, the clinician may write in each symptom or point to an image of a human figure to locate the symptom and rate the severity of that symptom. This baseline information indicates the starting point of the therapy which the clinician may refer back to for reference when determining the efficacy of the therapy. All details entered into GUI 152 may be stored in IMD 20 or in programmer 32. The clinician may continue to navigate to other screens of GUIs by selecting previous button 140, next button 130, or finish button 132.

Figure 13:
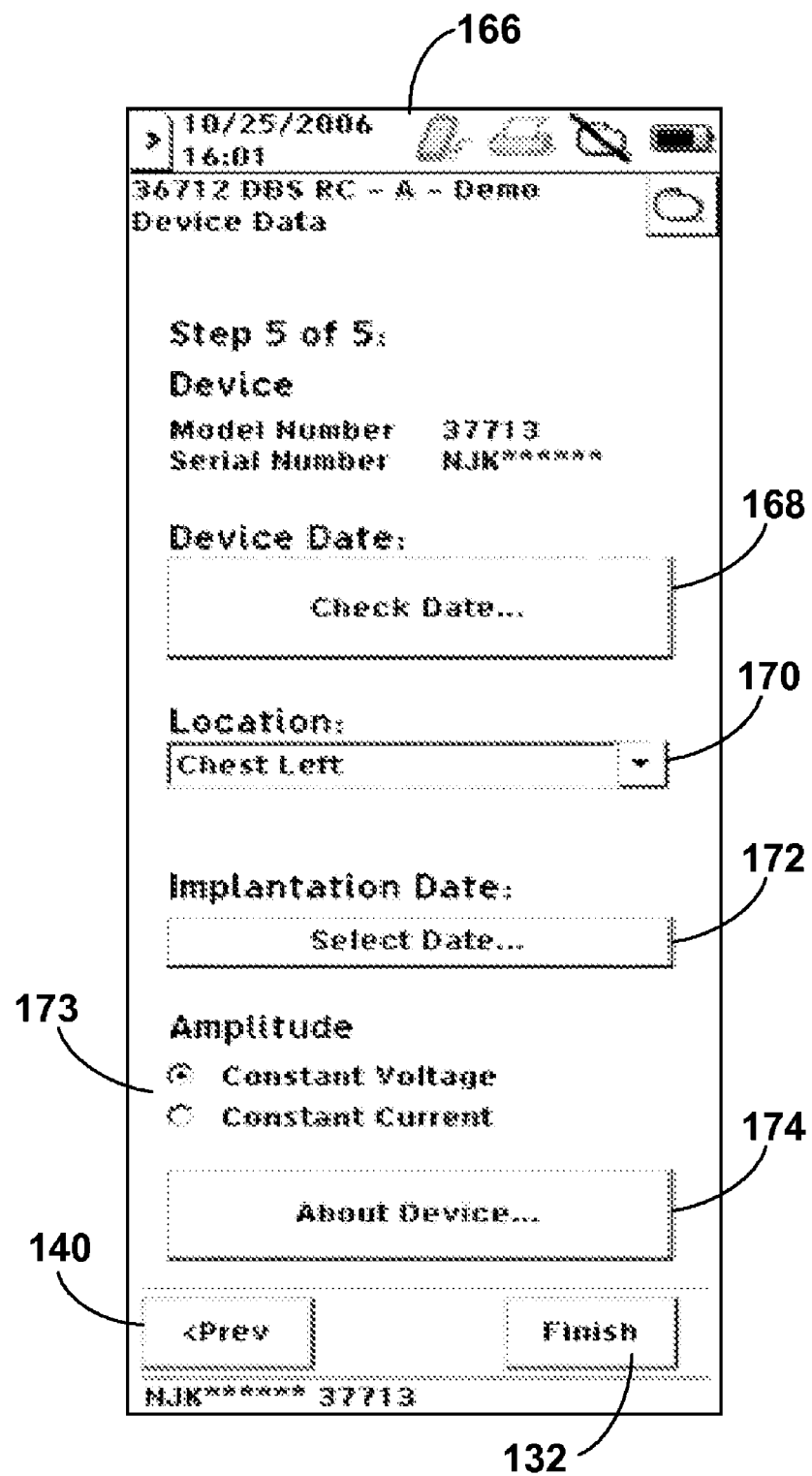

As shown in FIG. 13, GUI 166 presents an example fifth step of system 10 setup. GUI 166 includes input media 168 by which the clinician may check the date of the IMD, IMD location input 170, implant date selection input 172, amplitude mode option 173, and media which a clinician may select to input more IMD information 174. The clinician may review the date when IMD 20 was manufactured with IMD date check 168 and select the location of IMD 20 from the pull down menu of IMD location 170. The clinician may also enter the implantation date of IMD 20 and leads 14 with implant date 172. Amplitude option 173 allows the clinician to select how IMD 20 provides therapy. The clinician may enter the preference to keep constant voltage or constant amplitude during therapy. IMD information 174 may allow the clinician to review any details about IMD 20. Once the clinician has finished using GUI 166, the clinician may go back to other steps with previous button 140 or finish the setup and save all entered data by selecting finish button 132.

GUIs 118, 134, 142, 152, and 166 allow the clinician to enter required data for the successful operation of system 10 and resulting efficacious therapy. Since all of the information provided by the clinician is stored in memory 36 of IMD 20 and does not change with therapy duration, the clinician may skip the setup of system 10 throughout the remainder of therapy. However, the clinician may be able to review or modify the setup information via interaction with programmer 32 at any time. Once setup is complete, the clinician may continue with programming the stimulation parameters needed to begin stimulation therapy.

Figure 14:
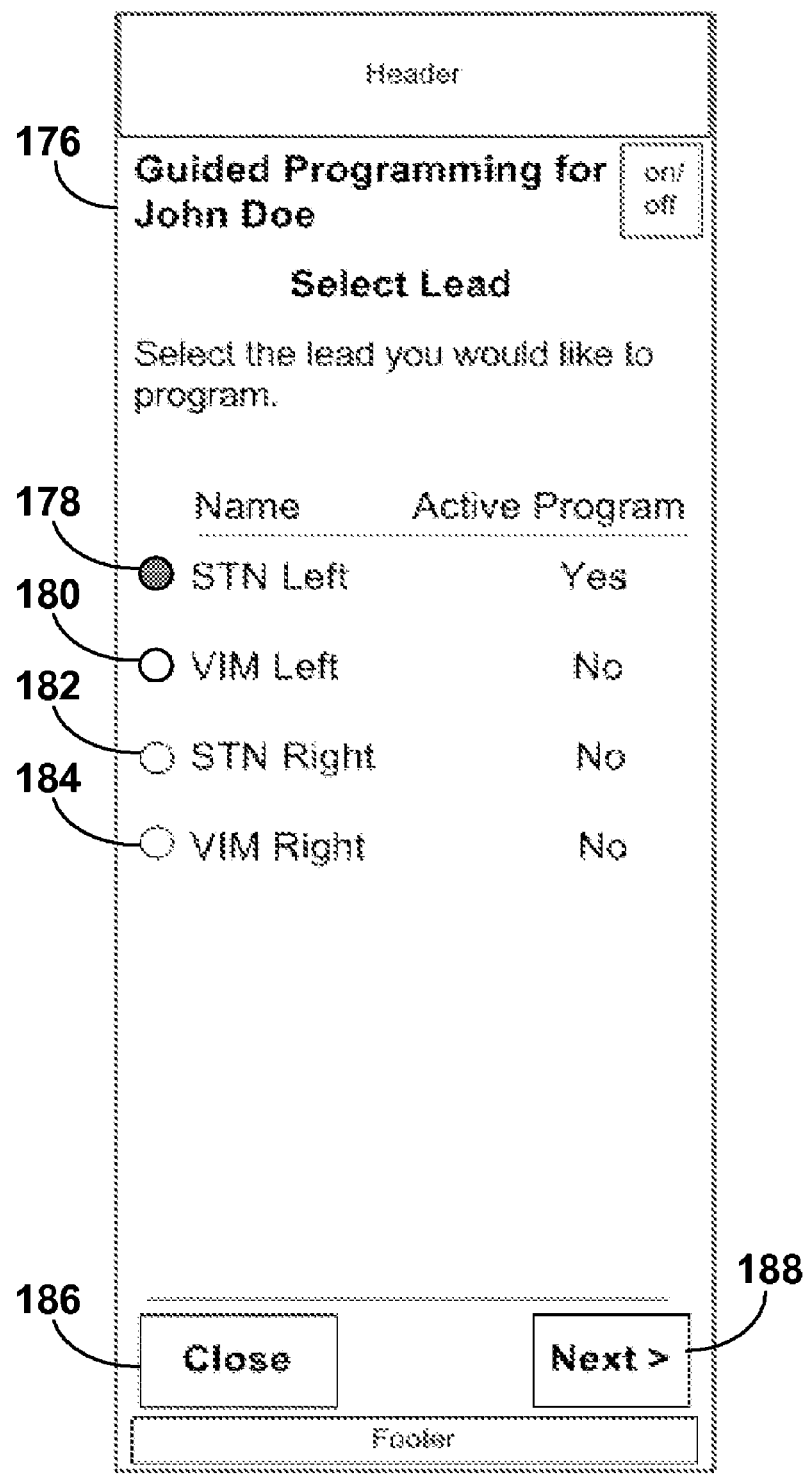
FIG. 14 is an example screen shot illustrating selection of a lead for guided programming.

FIG. 14 is an example screen shot illustrating a step of an example guided programming process that includes selecting a lead. As shown in FIG. 14, GUI 176 begins the guided programming of the stimulation therapy, which may occur after the initial system setup steps discussed above. The clinician may select one lead to program, such as lead 14A. In the example of GUI 176, four leads are available for programming, but only the STN Left lead has a currently active program assigned to it. The name "STN Left" may correspond to an anatomical position of the lead, such as the subthalamic nucleus in the left hemisphere of brain 18. The "VIM Left" name may correspond to another anatomical position of the lead, such as the ventral intermediate nucleus in the left hemisphere of brain 18. The clinician may select any one of circles 178, 180, 182 or 184, and select next button 188 to proceed with the guided programming for the selected lead. If the clinician desired to leave the guided programming, the clinician may select close button 186.

In other embodiments, the leads may not be described with words. Instead, each lead may be given a numerical value. Alternatively, GUI 176 may provide a representation of an anatomical region of patient 12 and display each of the separate leads as a lead icon in their representative location according to the anatomical region. In this manner, the clinician may click on a lead icon to select it for guided programming.

Once a lead is selected for the guided programming process, the clinician may stop stimulation on any other active lead delivering stimulation therapy. Stopping therapy on a lead in this manner may be referred to as "muting" or "pausing" therapy. Programmer 32 or IMD 20 may simply reduce the amplitude to zero to mute therapy. Muting therapy on leads not being screened may isolate the lead being tested so that patient 12 can focus on the screening process and eliminate effects from therapy delivered via other leads. Stimulation may be resumed once testing on the selected lead is completed.

In alternative examples of the guided programming, the clinician may not select which lead to program first. Instead, programmer 32 may require that the clinician enter guided programming for all leads that will be used for a single therapy. In this case, impedance checking would be performed for all leads before programming begins. Then the clinician may program one lead at a time until all leads have at least one program for therapy. A summary screen may then provide the selected programs for each lead of the therapy.

Figure 15:
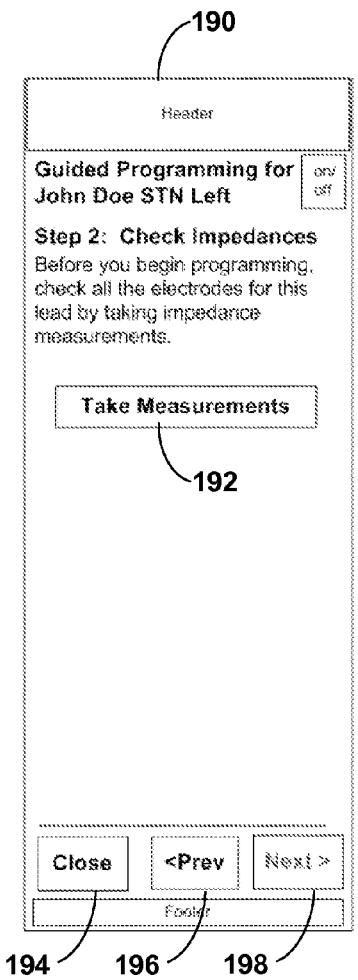
FIG. 15 is an example screen shot illustrating checking lead impedance as part of an example guided programming process.

FIG. 15 is an example screen shot illustrating another step of the guided programming process, which includes checking lead impedance. While checking lead impedance is shown as occurring after the clinician has selected a lead, the clinician may instead check lead impedances of all leads prior to selecting the lead to program. As shown in the example of FIG. 15, GUI 190 displays the first part of Step 2 of the guided programming. Programmer 32 directs the clinician to check the impedances of the selected lead, such as lead 14, by selecting take measurements button 192. Programmer 32 may check all unipolar and bipolar combinations including electrodes of the selected lead. In other embodiments, programmer 32 may automatically begin checking impedances after the clinician selects the lead in FIG. 14.

The clinician may select previous button 196 to return to GUI 176 or select close button 194 to exit the guided programming. Next button 198 is shaded or faded to indicate that the clinician cannot select the next button to proceed to the next GUI, i.e., screen. In order to proceed with guided programming, the clinician must select take measurements button 192. Example methods for determining the impedance associated with a combination of electrodes may similar to commonly known techniques, such as those described in commonly-assigned U.S. Pat. No. 6,978,171, which issued to Goetz et al. on Dec. 20, 2005, and is incorporated herein in its entirety by reference.

Figure 16:
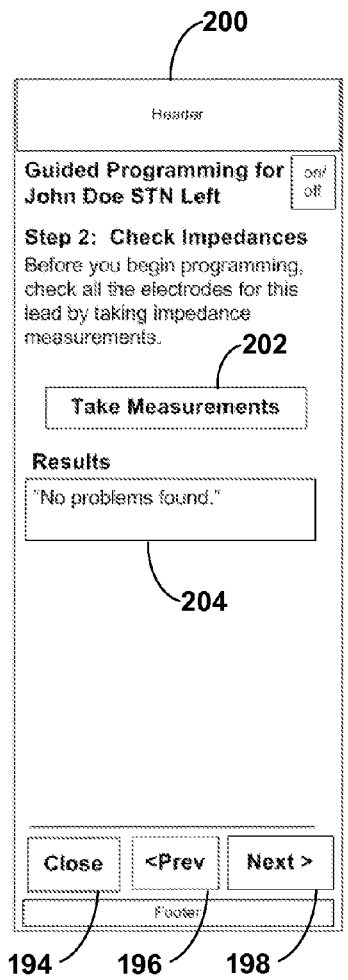
FIG. 16 is an example screen shot illustrating no problems found when checking lead impedance.

FIG. 16 is an example screen shot illustrating programming 32 indicating to the clinician that no problems were found when checking lead impedance. As shown in the example of FIG. 16, GUI 200 presents a possible results screen for checking impedance of the lead. Results box 204 indicates "No problems found" and tells the clinician the lead is functioning properly and ready for testing programs. The clinician may re-check the measurements by selecting take measurements button 202. When re-checking measurements, the clinician may increase the voltage or current amplitude of the measurement signal used in the check in order to receive more sensitive measurements. Alternatively, programmer 32 may automatically increase the voltage or current amplitude for each consecutive impedance check. To move forward with the guided programming, the clinician may select next button 198. The clinician may also return to GUI 190 by selecting previous button 196 or close the guided programming session by selecting close button 194.

In some embodiments, programmer 32 may continue directly to the next step of guided programming if no problems were found in the lead. Programmer 32 may quickly present a pop-up window telling the clinician that no problems were found and directly move to the next GUI after a discrete amount of time, or the programmer may simply move on without presenting any indication to the clinician.

Figure 17:
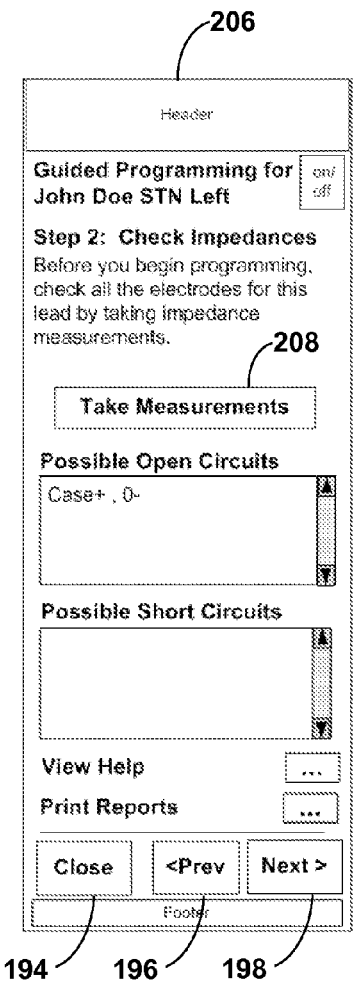
FIG. 17 is an example screen shot illustrating possible problems when checking lead impedance.

FIG. 17 is an example screen shot illustrating possible problems when checking lead impedance. As shown in FIG. 17, GUI 206 may be presented instead of GUI 200 after the clinician selects take measurement button 192 in GUI 190. If one or more problems with the lead are detected, programmer 32 provides the clinician with detailed information to help the clinician fix system 10 or otherwise address the problem. GUI 206 includes a possible open circuits box which identifies one or more potential open circuits and a possible short circuit box that identifies one or more possible short circuits. The clinician may choose to view a help menu to fix the problem or to print the check impedances report. A printed report may provide more information that does not fit within GUI 206. Impedance checking of the electrodes may be performed according to the disclosure of commonly-assigned U.S. patent application Ser. No. 11/590,741, to Goetz et al., which was filed on Oct. 31, 2006, and is incorporated herein in its entirety by reference.

Once the clinician attempts to fix or otherwise address the problem, the clinician may select take measurement button 208. System 10 will once again check the impedances of the lead. If the problem has been fixed, programmer 32 may present GUI 200. If the clinician has not remedied the problem, GUI 206 may again be presented to further aid the clinician in fixing the problem. Once the problem is fixed, the clinician may select next button 198 to move on with the guided programming. The clinician may also select previous button 196 to return to GUI 190 or close button 194 to exit the session.

In the case that the clinician or system 10 cannot fix the impedance problem with the lead, programmer 32 may identify which electrode or electrodes are impacted by the lead integrity problem. Programmer 32 and/or IMD 20 may remove any identified electrodes from inclusion or use in electrode combinations. In addition, programmer 32 and/or IMD 20 may remove any programs that deliver stimulation via the identified electrodes. In this manner, patient 12 and the clinician will not waste time testing electrode combinations that will not be functional or will cause adverse effects to the patient.

Figure 18:
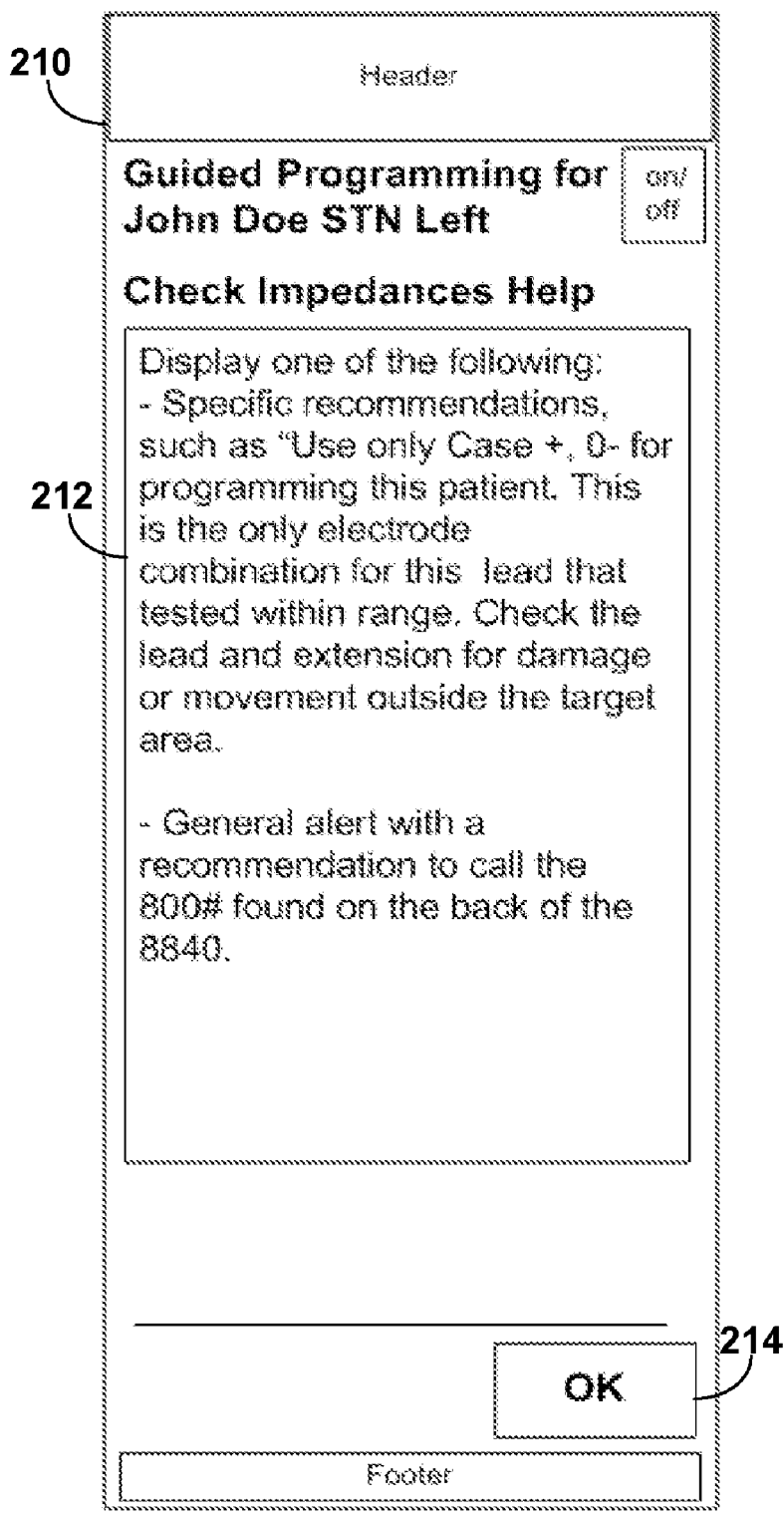
FIG. 18 is an example screen shot illustrating a help screen for checking impedances.

FIG. 18 is an example screen shot illustrating a help screen for checking impedances. As shown in FIG. 18, GUI 210 displays help to the clinician in text box 212. If the text within text box 212 is too long, programmer 32 may provide scroll bars that enable the clinician to scroll through the text. Once the clinician is finished viewing GUI 210, the clinician selects ok button 214. The help messages may instruct the clinician to call a particular phone number or to use only a particular electrode combination or set of combinations.

Figure 19:
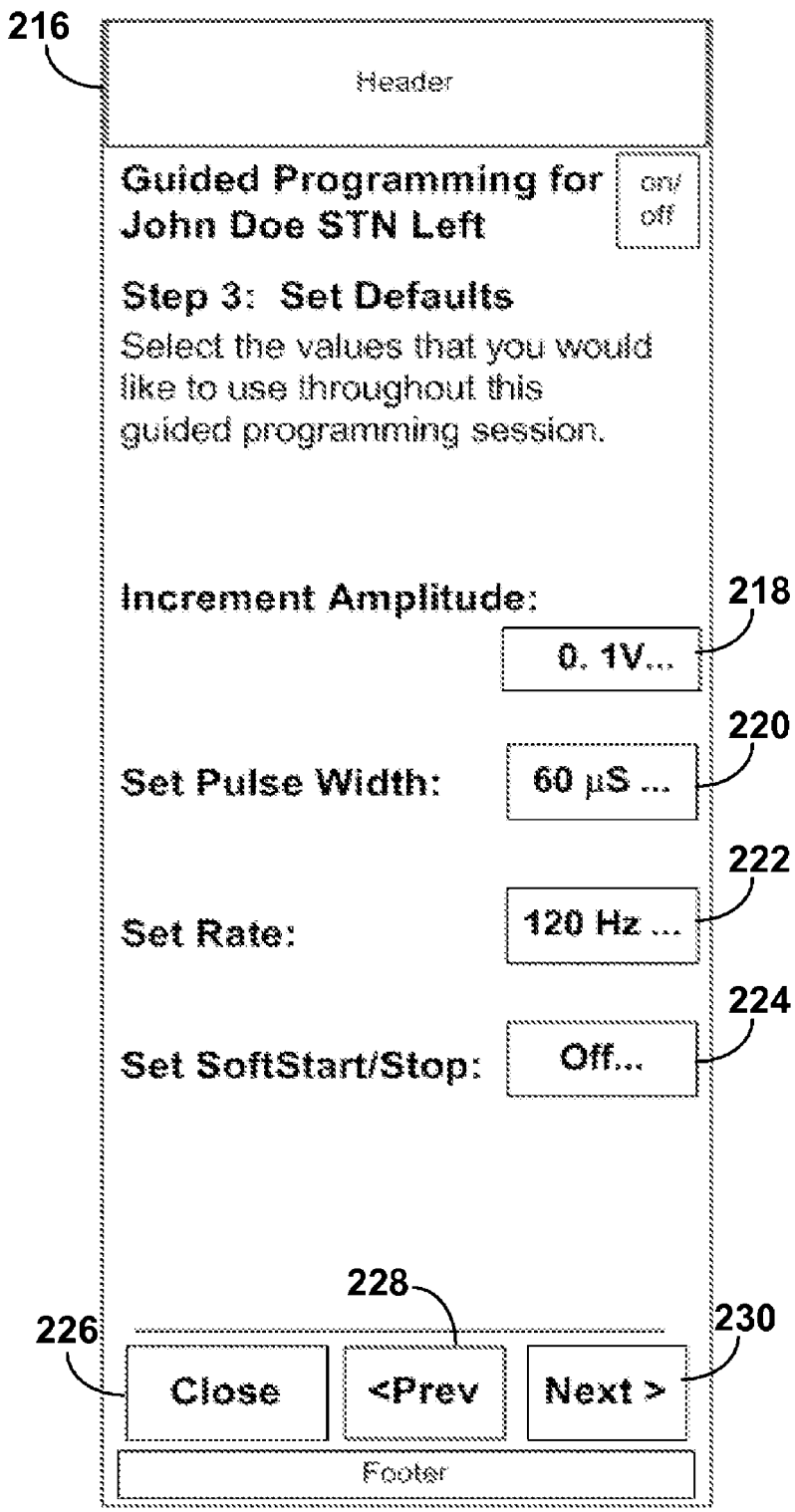
FIG. 19 is an example screen shot illustrating setting default stimulation parameters as part of an example guided programming process.

FIG. 19 is an example screen shot illustrating a third step of the example guided programming process, which includes setting default stimulation parameters. As shown in FIG. 19, GUI 216 presents a default setting mechanism to the clinician. The clinician may set the amplitude increment in amplitude box 218, set the pulse width in pulse width box 220, set the pulse rate in rate box 222, and set the soft start/stop preference using soft start/stop box 224. Each box 218, 220, 222 and 224 may allow numerical input, increase or decrease input, or selection from a menu when one of the boxes is selected by the clinician.

Example amplitude increments include 0.05 Volts (V), 0.1 V, 0.2V, and 0.5 V. Ramping speed may be set between zero and ten seconds. Additionally, soft start box 224 may control the delay of beginning the test program, which may be between zero and ten seconds. Once the clinician has set the default parameters, the clinician may select next button 230 to move on with the guided programming. The clinician may also select previous button 228 to return to the previous GUI or close button 226 to exit the session.

Figure 20:
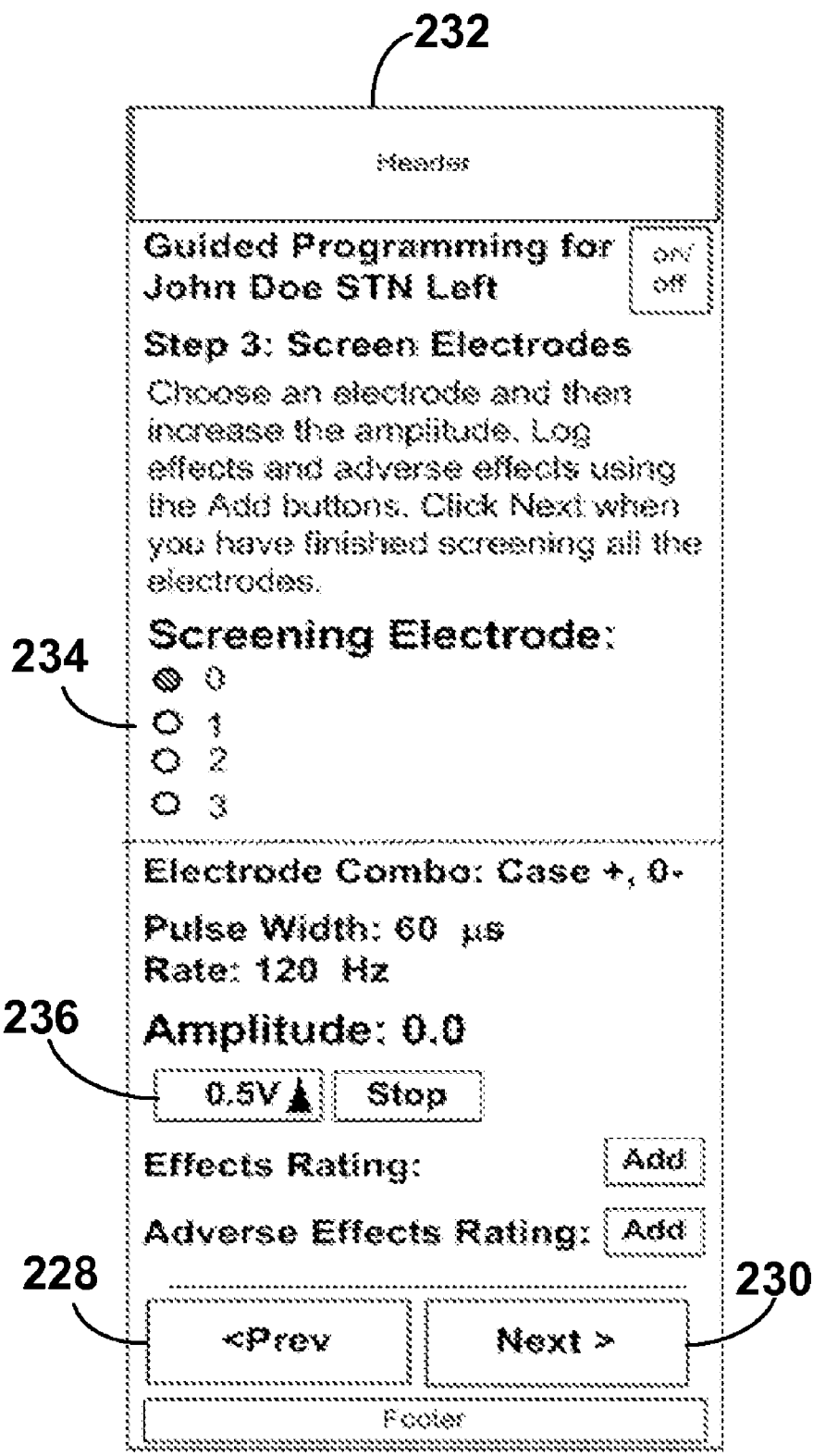
FIG. 20 is an example screen shot illustrating selecting an electrode to test as part of an example guided programming process.

FIG. 20 is an example screen shot illustrating the third step of the example guided programming process, which includes selecting an electrode to test. As shown in FIG. 20, programmer 32 presents GUI 232 to the clinician for Step 3 which includes choosing electrodes and defining programs. GUI 232 may be effective in screening unipolar electrode combinations. GUI 232 includes electrode buttons 234 that allow the clinician to select an electrode to test as part of the stimulation test program. GUI 232 includes a summary of the electrode combination, the pulse width, the pulse rate, and the amplitude in volts. The clinician may select the initial or subsequent voltage amplitude with amplitude button 236. During the test stimulation, the clinician may manually request to add a positive input rating the positive effects or a negative input rating the adverse effects. Alternatively, programmer 32 may force the clinician to add a positive or negative input when the clinician selects next button 230, e.g., before proceeding to a next step of the process. The clinician may also return to GUI 190 by pressing previous button 228.

Pulse width and pulse rate are parameters that programmer 32 may automatically set and adjust according to the rating information. In some embodiments, the clinician may select a button that allows the clinician to adjust all parameters manually. Some clinicians may prefer the ability to override programmer 32 guidance according to their medical experience. In other embodiments, GUI 232 may provide a screen that includes more icons and visual displays regarding the parameters.

Figure 21A:
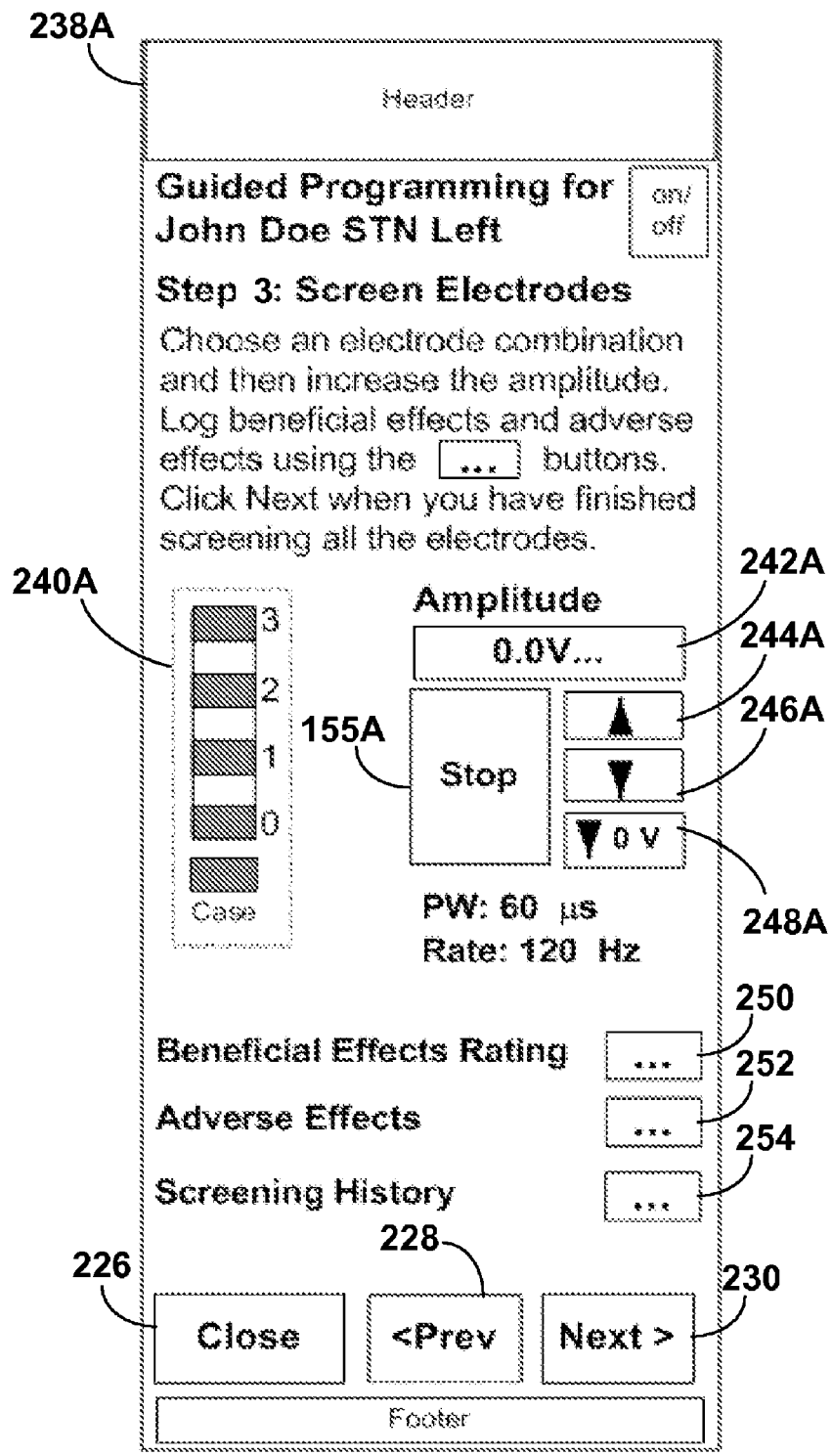
FIGS. 21A and 21B are example screen shots illustrating a step of selecting an electrode to test and providing effects as part of an example guided programming process.
Figure 21B:
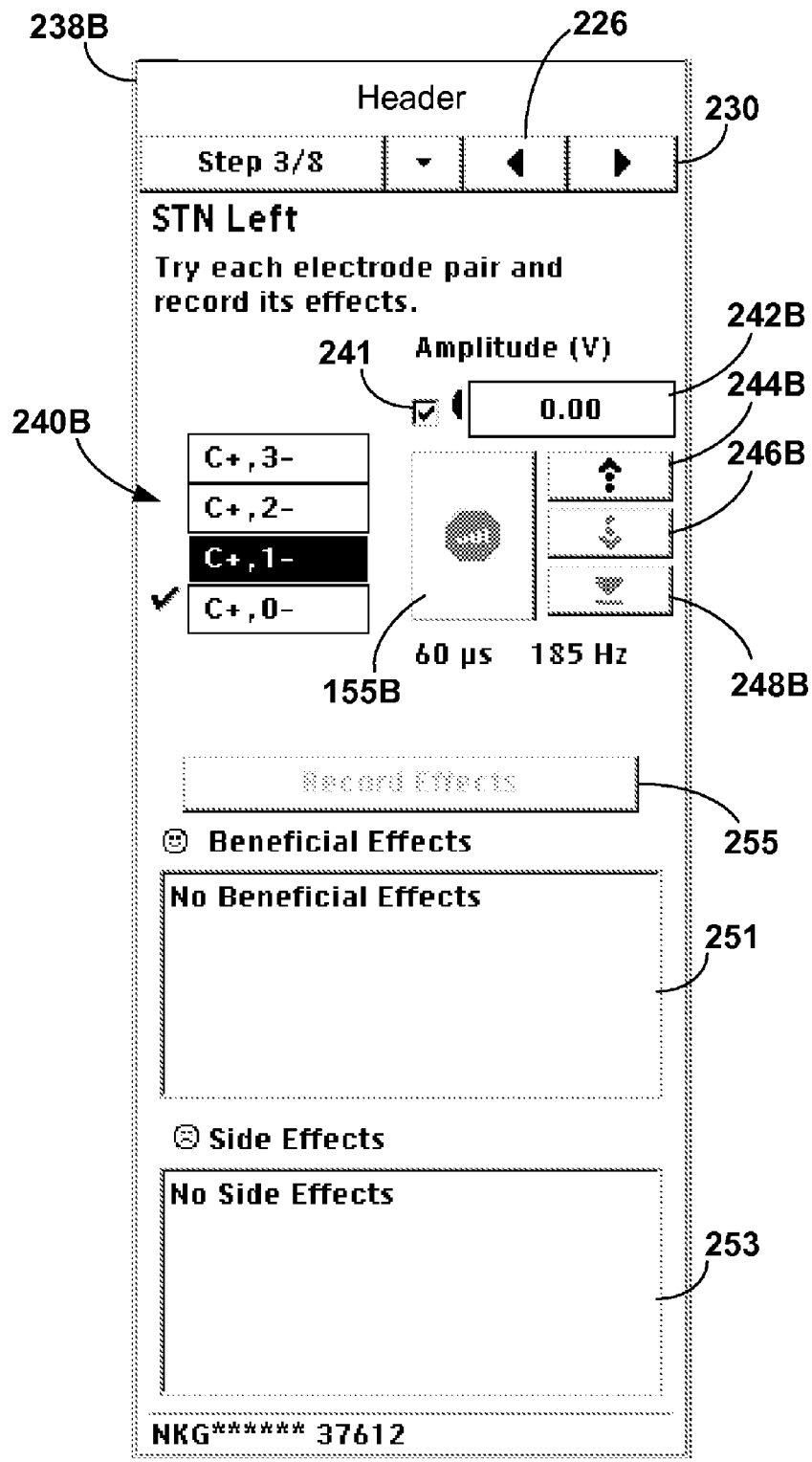

FIGS. 21A and 12B are example screen shots illustrating a step of selecting an electrode to test and providing effects as part of an example guided programming process. FIGS. 21A and 21B are alternatives to GUI 232 of FIG. 20. FIG. 21A includes GUI 238A, electrode selection 240A, amplitude display 242A, stop button 155A, increase arrow 244A, decrease arrow 246A, and reset amplitude 248A. Selection of increase arrow 244A and increase arrow 246A increase and decrease, respectively, the amplitude of the stimulation. Selection of reset amplitude 248A brings the amplitude back to zero in order to test another electrode combination or start testing over. GUI 238A also includes positive effect button 250, adverse effect button 252, and screening history button 254. Screening history button 254 provides access to a screen showing the lead screening history for the patient, e.g., which may indicate which leads or electrode combinations have been evaluated earlier during the current programming session, or during one or more prior programming sessions. Electrode selection 240 may allow selection of unipolar or bipolar electrode combinations.

For each screening of a particular electrode combination, the voltage amplitude or current amplitude may be ramped up until the first adverse side effect is perceived by patient 12 or the clinician. Once this first adverse side effect is noticed, stimulation with that particular electrode combination may stop by the selection of stop button 155A. Alternatively, the voltage amplitude or current amplitude may increase until the adverse effects are no longer tolerable or the beneficial effects are outweighed by the adverse effects. GUI 238A allows the clinician to manage the guided programming process and input positive (or beneficial) and adverse effects caused by the tested program. The clinician may select positive effect button 250 to input perceived beneficial effects and/or select adverse effect button 252 to input perceived adverse effects. Any input is then stored and related to the current electrode combination and other stimulation parameters. Once the clinician has tested one or more programs, the clinician may select next button 230 to move on with the guided programming. The clinician may also select previous button 228 to return to the previous GUI or close button 226 to exit the session.

FIG. 21B includes GUI 238B, which is substantially similar to GUI 238A in that GUI 238B allows the clinician to screen electrodes in a guided format. GUI 238B includes electrode selection 240B, amplitude display 242B, stop button 155B, increase arrow 244B, decrease arrow 246B, and reset amplitude 248B. Electrode selection 240B provides unipolar electrode combinations that the clinician may select for testing. Once a combination has been tested and at least one beneficial effect or adverse effect has been logged, a check mark may be added next to that tested electrode combination to indicate to the clinician that testing for that combination has been performed. Bipolar electrode combinations and/or partial electrode combinations may also be provided to the clinician in electrode selection 240B automatically once unipolar combinations have been tested or at the request of the clinician. Selection of increase arrow 244B and increase arrow 246B increase and decrease, respectively, the amplitude of the stimulation. Selection of reset amplitude 248B brings the amplitude back to zero in order to test another electrode combination or start testing over.

For each screening of a particular electrode combination, the voltage amplitude or current amplitude may be ramped up until the first adverse side effect is perceived by patient 12 or the clinician. Once this first adverse side effect is noticed, stimulation with that particular electrode combination may stop by the selection of stop button 155B. Alternatively, the voltage amplitude or current amplitude may increase until the adverse effects are no longer tolerable or the beneficial effects are outweighed by the adverse effects. GUI 238B also includes record effects button 255, beneficial effect field 251, and adverse side effect field 253. During the testing of each electrode combination, the clinician may stop test stimulation with stop button 155B to log any perceived effects of the stimulation. Selecting record effects button 255 presents GUIs 256 and 282 of FIGS. 22 and 23 which allow the clinician to enter effects. Once the effects are entered, the entered effects are displayed to the clinician in the respective beneficial effect field 251 and adverse side effect field 253.

Any input is then stored and related to the current electrode combination and other stimulation parameters, e.g., within the memory of a programmer of the IMD, as described above. Once the clinician has tested one or more programs, the clinician may select next button 230 to move on with the guided programming. The clinician may also select previous button 228 to return to the previous GUI or choose any step of the guided programming session by selecting menu button 231 which presents a drop down menu of possible destinations within the guided programming session. In some examples, elements of GUIs 238A and 238B may be combined to create a GUI with any type of functionality described herein.

Figures 22, 23:
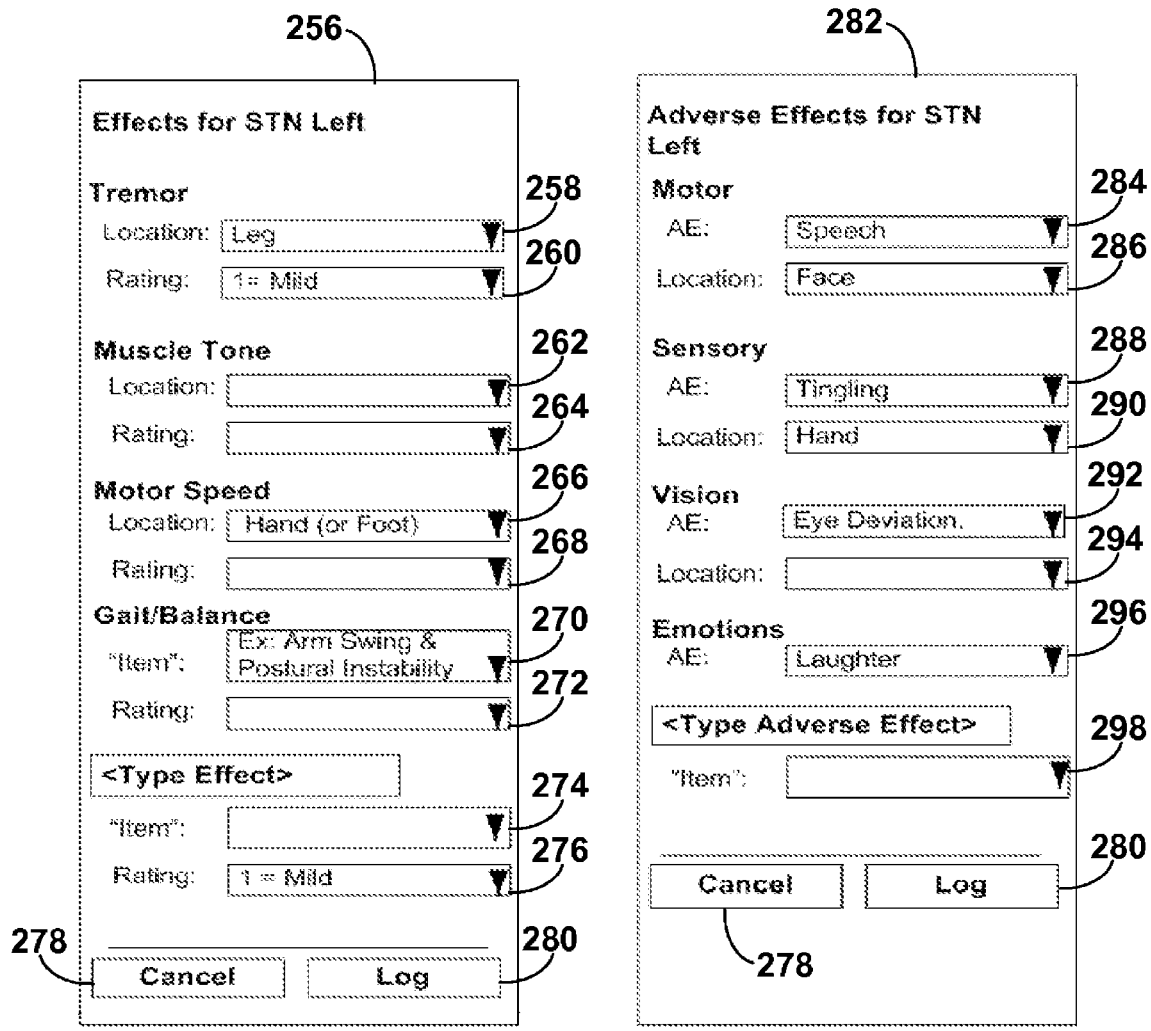
FIG. 22 is an example pop-up screen illustrating drop-down menus for rating the effects of stimulation.
FIG. 23 is an example pop-up screen illustrating drop-down menus for rating the adverse effects of stimulation.

FIG. 22 is an example pop-up screen illustrating drop-down menus for rating the effects of stimulation. As shown in FIG. 22, GUI 256 pops up to allow the clinician to provide positive input rating positive effects associated with the test program. Effects listed in GUI 256 are diagnosis dependent and are presented by programmer 32 according to the diagnosis of patient 12. GUI 256 may include example effects for patient 12 diagnosed with Parkinson's disease. Other effects may be present in GUI 256 for a patient diagnosed with other diseases or conditions.

GUI 256 includes multiple categories for specific feedback. Location menu 258 and rating menu 260 describe any tremors in terms of rating, e.g., mild, moderate, sever, and location in the patient's body, e.g., leg. Location menu 262 and rating menu 264 describe muscle tone of patient 12 in terms of rating and location in the patient's body, e.g., leg. Location menu 266 and rating menu 268 describe motor speed of patient 12 in terms of rating and location in the patient's body, e.g., hand or foot. Patient gait and balance is also described by item menu 270 and rating menu 272, e.g., arm swing and postural instability. In addition, the clinician may type in another effect not listed in GUI 256. This custom effect is described with item menu 274 and rating menu 276.

The clinician selects log button 280 to save and exit GUI 256. All effect and/or rating information is saved in memory 46 of programmer 32 and/or in memory 36 of IMD 20. Alternatively, the clinician may select cancel button 278 to avoid saving any rating information and exit GUI 278. Programmer 32 uses the rating information provided in positive inputs in GUI 256 to generate the next electrode combination and the next program. In addition, programmer 32 sorts the tested programs based upon the rating information collected from the clinician with GUI 256. In some embodiments, rating information may not be used when logging the effects. Simply noting that tremors in the leg of patient 12 have been reduced may be enough information to effectively continue the guided programming process.

FIG. 23 is an example pop-up screen illustrating drop-down menus for rating the adverse effects of stimulation. As shown in FIG. 23, GUI 282 pops-up to allow the clinician to provide negative input for rating adverse effects associated with the test program. Adverse effects listed in GUI 282 are therapy dependent and are presented by programmer 32 according to the type of stimulation therapy provided to patient 12. GUI 282 may include example adverse effects for patient 12 being given stimulation directed to treating Parkinson's disease. Other adverse effects may be present in GUI 282 for a patient given other stimulation therapies. GUI 282 includes multiple categories, similar to GUI 256, for specific feedback. Adverse effect (AE) menu 284 and location menu 286 describe adverse motor effects, e.g., adverse effect: speech and location: face. AE menu 288 and location menu 290 describes adverse sensory affects noticed by patient 12, e.g., adverse effect: tingling and location: hand. AE menu 292 and location menu 294 describe any adverse effects to vision, e.g., adverse effect: eye deviation, and AE menu 296 describes adverse emotional changes due to the test program, e.g., adverse effect: laughter. In addition, the clinician may type in another adverse effect not listed by GUI 282. The other adverse effect is further described with item menu 298. In alternative examples, GUIs 256 and 282 may be included in the same GUI with tabs that allow the clinician to toggle between the beneficial effects of GUI 256 and the adverse effects of GUI 282.

Similar to GUI 256, the clinician selects log button 280 to save and exit GUI 282. All effect and/or rating information is saved in memory 46 of programmer 32 and/or in memory 36 of IMD 20. Alternatively, the clinician may select cancel button 278 to avoid saving any effect or rating information and exit GUI 282. Programmer 32 uses the effect and rating information provided in GUI 282 to generate the next electrode combination, or avoid certain electrode combinations, and the next program. In addition, programmer 32 sorts the tested programs based upon the effect and/or rating information collected from the clinician with GUI 282.

Figure 24:
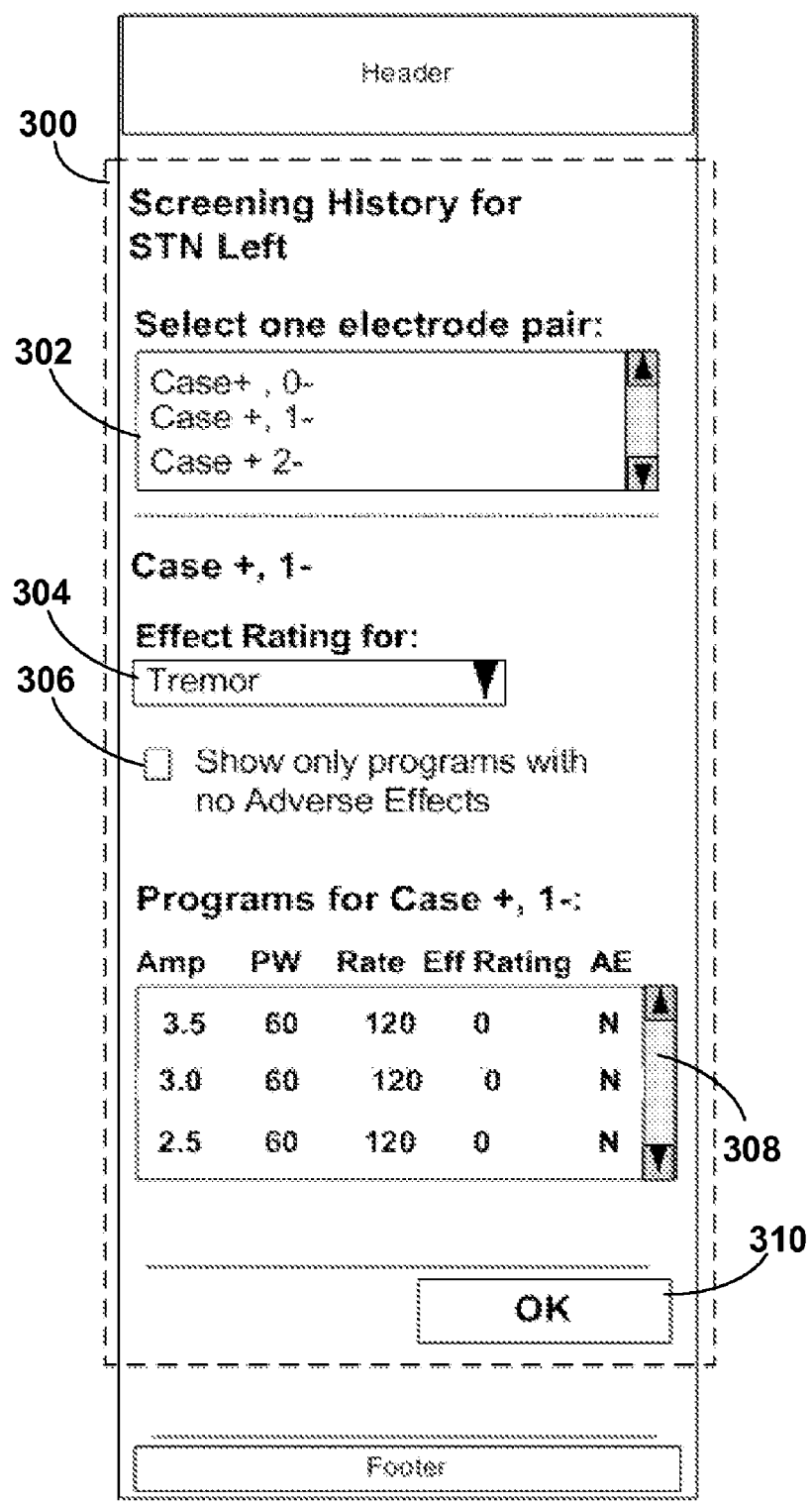
FIG. 24 is an example screen shot illustrating a pop-up window indicating the screening history for the selected lead.

FIG. 24 is an example screen shot illustrating a pop-up window indicating the screening history for the selected lead. As shown in FIG. 24, GUI 300 presents screening history from the guided programming process. The screening history is provided so that a clinician can determine how deep into the guided programming process the clinician got during the previous session that was not completed. GUI 300 includes electrode pair box 302, rating box 304, check box 306, sorted program box 308 and ok button 310.

The clinician selects an electrode combination from electrode pair box 302 and the effect rating desired from rating box 304. The combination of selections made in boxes 302 and 304 determine the programs listed in program box 308. In some examples, electrode pair box 302 may include an "all electrodes" selection and rating box 304 may include a "best overall" program selection. The "best overall" rankings for programs may be determined using weighted averages or sums in the manner described above. If a different electrode combination is selected in electrode pair box 302, the corresponding programs will appear in sorted program box 308. Some embodiments may be accessible from programmer 32 without running guided programming to allow the clinician to select a program to be added to an active program group or used to replace a program in the active program group. As described herein, the electrode combination is part of the stimulation parameters defined in a program. In other words, a program may consist of an electrode combination, a current amplitude, a voltage amplitude, a pulse width, and a pulse rate. Therefore, changing the amplitude of current stimulation parameters effectively changes the program that defines the stimulation therapy. Other stimulation parameters may be used in systems that produce continuous signals instead of pulses. In alternative examples, each electrode combination may include multiple current or voltage amplitudes for respective electrodes. These multiple amplitudes may be applied in cases when simultaneous pulses or stimulation steering is used to adjust the perceived location of the therapy.

In some examples, an electrode combination and other stimulation parameters may be screened or tested multiple times throughout the therapy of patient 12. Programmer 32 or IMD 20 may store all of the results from each test in the screening history. In addition, a trend or change in the effects logged with same stimulation parameters over a period of time may be provided to the clinician over time. This trend may allow the clinician to monitor changes in the disease state or therapy accommodation of patient 12 over the duration of therapy. Further, the clinician may use this information when determining appropriate medication therapies for patient 12 along with the stimulation therapy.

Figure 25:
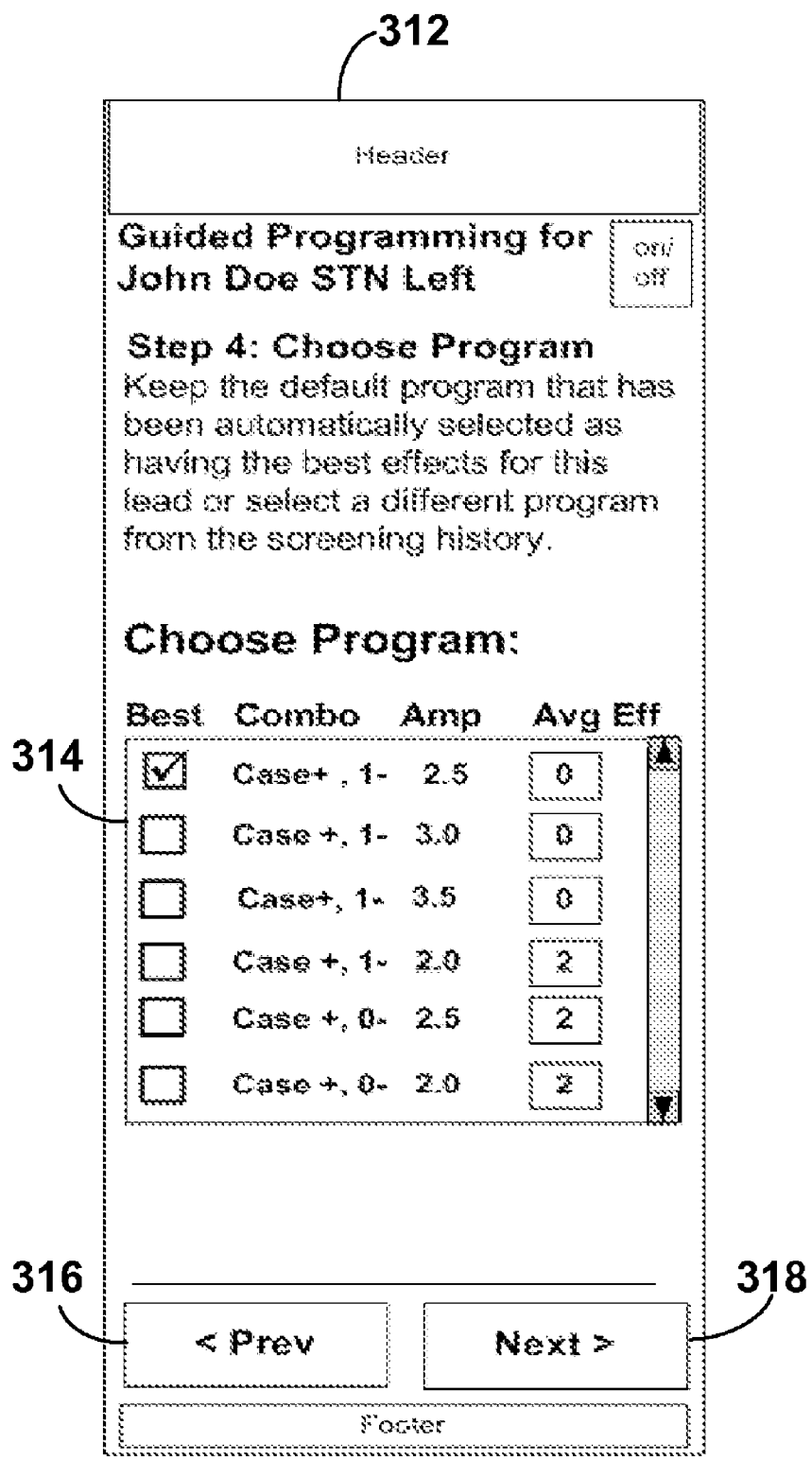
FIG. 25 is an example screen shot illustrating selecting the best program for stimulation therapy based on the ratings as part of an example guided programming process.

FIG. 25 is an example screen shot illustrating a fourth step of the example guided programming process, which includes selecting the best program for stimulation therapy based on the ratings. As shown in FIG. 25, GUI 312 displays Step 4 of the guided programming process to the clinician. The clinician selects the preferred or best one or more programs from a sorted list of tested programs for the currently selected lead. GUI 312 may list all programs tested or a selected subset of the most efficacious tested programs. GUI 312 includes program list 314 to present the tested programs in an organized manner. Program list 314 includes a few stimulation program parameters, such as the electrode combination and the voltage or current amplitude, the average effects, and a selectable box for the clinician to check the preferred program.

Programmer 32 has already pre-selected a default program based upon the rating information (shown as checked in program list 314). The clinician may simply select next button 318 to accept the pre-selected program, or the clinician may select a different program from program list 314. More than one program may be selected in some embodiments when programmer 32 and IMD 20 support multiple program storing. The clinician may select next button 318 to move to the next step of the guided programming. Alternatively, the clinician may select previous button 316 to return to GUI 232.

In some embodiments, program list 314 may display all rating information to the clinician instead of selected positive effects, negative effects, or rating information. The average effect displayed in program list 314 may correspond to a computed number based upon both the positive and adverse effects. Displaying all rating information separately may allow the clinician to quickly view all parameters of the sorting process used by programmer 32 to sort the list of tested programs. This information may allow the clinician to more easily decide what program to select. Alternatively, the clinician may select a show all button (not shown) to review all effect and rating information associated with the tested programs.

Figure 26:
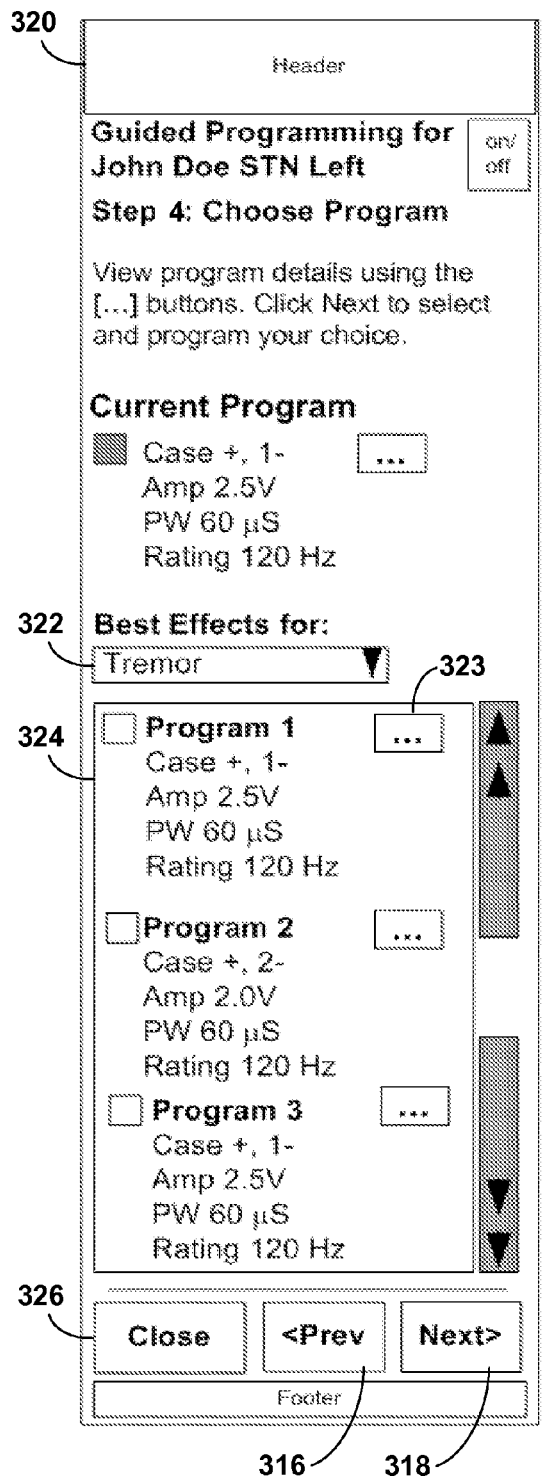
FIG. 26 is an example screen shot illustrating a step of an example guided programming process that includes sorting and selecting the best stimulation therapy.
Figure 27:
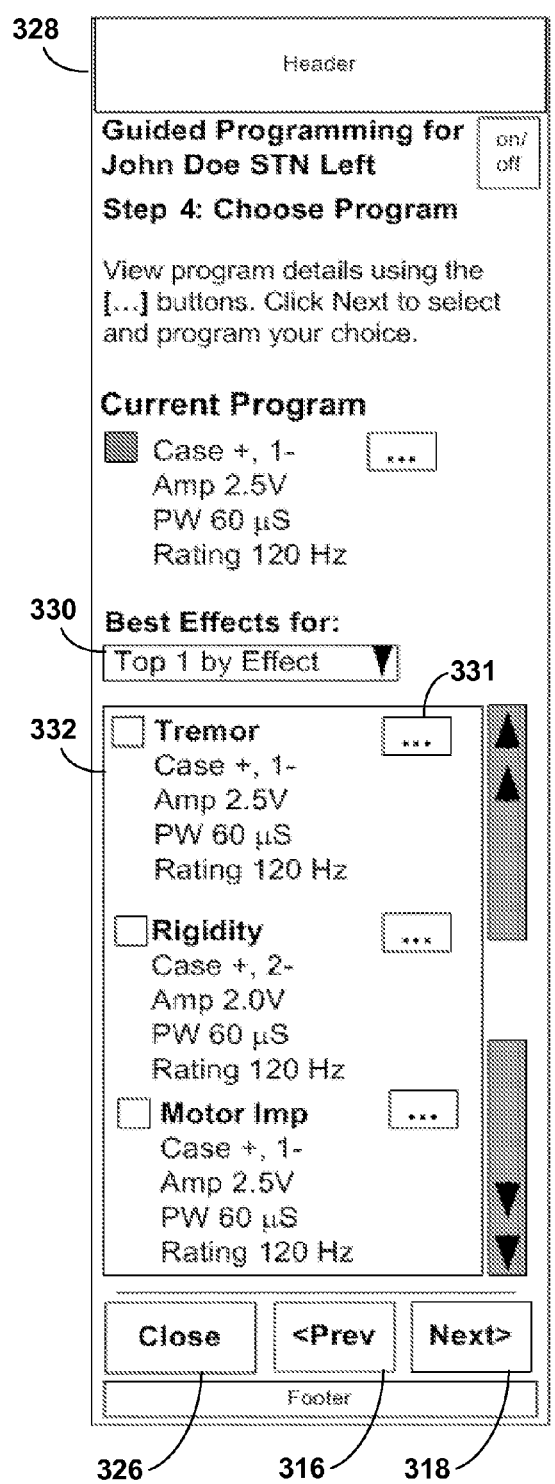
FIG. 27 is another example screen shot illustrating a step of an example guided programming process that includes sorting and selecting the best stimulation therapy.

FIGS. 26 and 27 are example screen shots illustrating a step that includes sorting and selecting the best stimulation therapy. Both FIGS. 26 and 27 are alternative embodiments of GUI 312 in FIG. 25. FIG. 26 shows GUI 320 that allows the clinician to select one of the tested programs. GUI 320 includes sort parameter 322 and sorted program box 324. GUI 320 displays the currently used program and, in the illustrated example, displays the tested programs sorted by their effect on tremors. Once the clinician has selected a program, the clinician may select next button 318 to move on with the guided programming. The clinician may also select previous button 316 to return to the previous GUI or close button 326 to exit the session.

GUI 328 of FIG. 27 is similar to GUI 320 of FIG. 26. GUI 328 includes sort parameter selection media 330 and sorted program box 324. GUI 328 presents the best tested program for each of a plurality of positive and/or negative effects. Other sorting parameters may be selected by the clinician as well. Once the clinician has selected a program from GUI 328, the clinician may select next button 318 to move on with the guided programming. The clinician may also select previous button 316 to return to the previous GUI or close button 326 to exit the session.

Programs may be sorted according to many aspects of each tested program. Aspects of each program may include beneficial effects, adverse effects, amplitude usage range, and absolute amplitude. The amplitude usage range is the total range of voltage or current amplitude that the program could deliver to patient 12. A larger amplitude usage range may allow the clinician to adjust stimulation amplitude during therapy to account for diminishing therapeutic effects of the program over time. The absolute amplitude is the amplitude needed to provide stimulation therapy. Lower absolute amplitudes reduce power consumption and maximize the life of IMD 20 battery. Each of these aspects of a program may have a greater weight than another when determining the best program. For example, the preferred weighting of program aspects from most important to least important may follow as: adverse effects, beneficial effects, amplitude usage range, and absolute amplitude. Therefore, in this example, the best program may have minimal adverse effects, maximum beneficial effects, maximum amplitude usage range, and lowest absolute amplitude. However, the clinician or patient 12 may determine which aspects are the most important to efficacious treatment of the patient's condition.

In GUIs 320 and 328, sort parameter inputs 322 and 330 include selectable parameters for sorting tested programs, such as sorting by effectiveness in alleviating tremor, rigidity, motor impairment, or gait. Inputs 322 and 330 may also include a clinician customizable parameter, and allow a clinician to select display of the top program for each of a plurality of positive and/or negative effects. Up to three programs may be displayed in either sorted program box 324 or 332. Additionally, the scroll bar located on the side of each sorted program box 324 and 332 may be activated if the list includes more than three programs. In other embodiments, less or more than three programs may be visible. If the clinician desires to view more details about a program before choosing the program, the clinician may select the expand detail button 323 and 331 adjacent to the program. A similar expand detail button is located next to each program shown in GUIs 320 and 328.

FIG. 28 is an example screen shot illustrating a pop-up window showing a summary of the selected program. As shown in FIG. 28, GUI 334 presents the clinician with a summary of the selected program, including electrode combination, parameter values, positive effects, adverse effects and therapy window, indicating the amplitude range from the first effect to the first adverse effect. The clinician may select ok button 338 to accept the program or cancel button 336 to reject the selected program. Only one program per lead may be stored in IMD 20 in the example of FIG. 28. However, other examples may allow IMD 20 to store multiple programs for each of leads 14.

Figure 29:
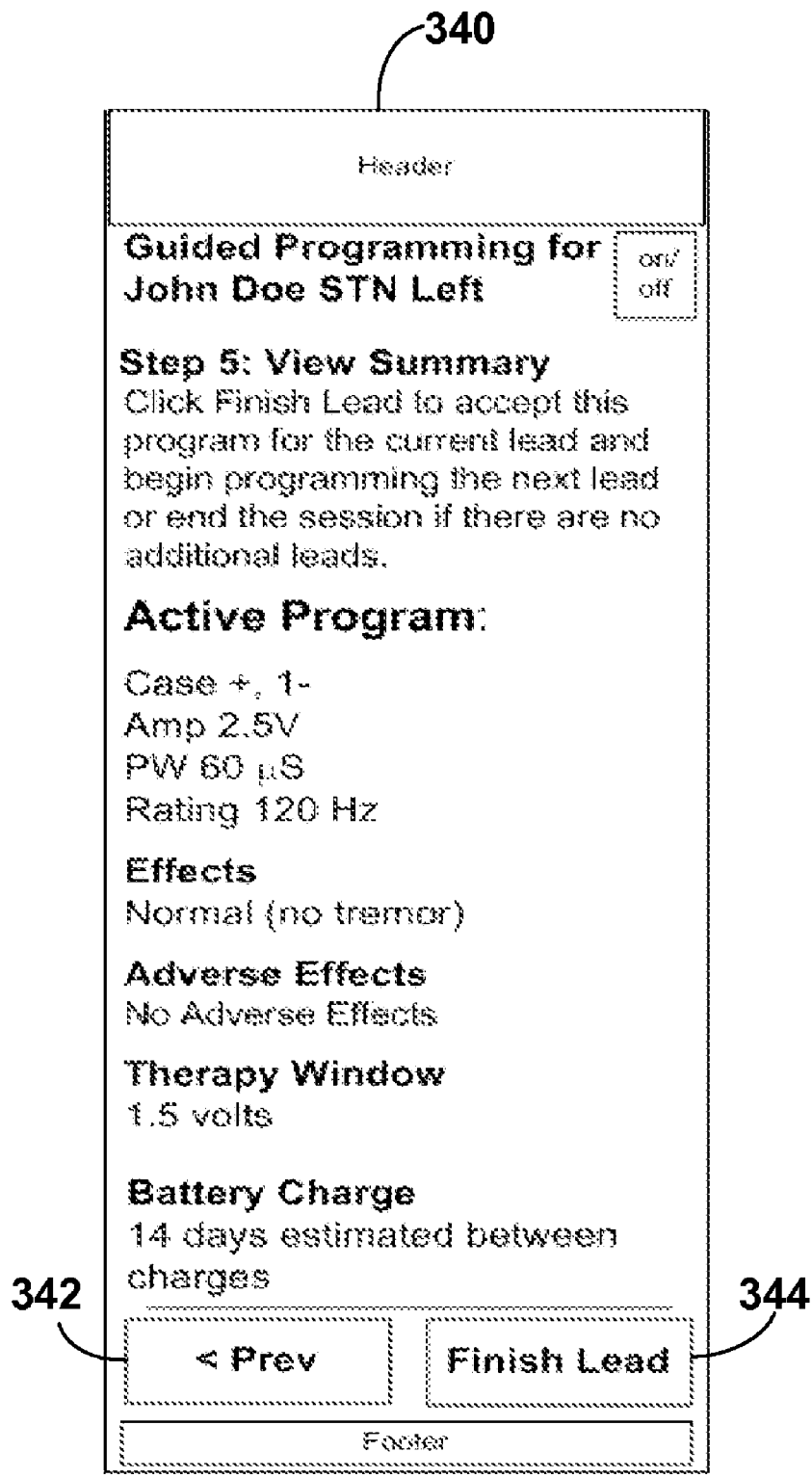
FIG. 29 is an example screen shot illustrating viewing the summary for the selected program as part of an example guided programming process.

FIG. 29 is an example screen shot illustrating the fifth step of the example guided programming process, which includes viewing the summary for the selected program. As shown in FIG. 29, GUI 340 presents a summary for the selected program to the clinician. GUI 340 may display the stimulation parameters that make up the selected program, the effects, the adverse effects, the therapy window, and the device longevity using the selected program. This information is useful to the clinician and patient 12 in deciding whether or not to keep the selected program and begin therapy. GUI 340 may also include a mute box or other selection mechanism that allows the clinician to resume therapy on any other leads that were muted before the screening process had commenced. Resuming therapy may simply increase amplitude of the therapy from zero back to previous levels. In some examples, an additional GUI may be provided to prompt the resuming of previous therapy, or programmer 32 may automatically resume the therapy on other leads.

In addition, the clinician may be able to view the screening history for the lead to look at old tested programs. The clinician may also return to the screening history at a later time when reviewing stimulation therapy. The clinician may select previous button 342 to return to GUI 312 and select a different program. If the clinician is satisfied with the selected program, the clinician selects finish lead button 344 to save the information needed for therapy. In some examples, GUI 312 may allow the clinician to select the desired staring amplitude for the selected program. In addition, the clinician may set up an allowable amplitude range for the selected program which patient 12 may use during therapy.

Figure 30:
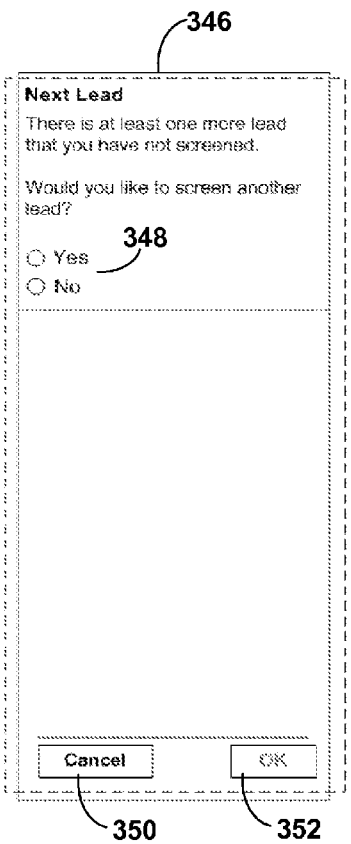
FIG. 30 is an example pop-up window after a program has been selected.
Figure 31:
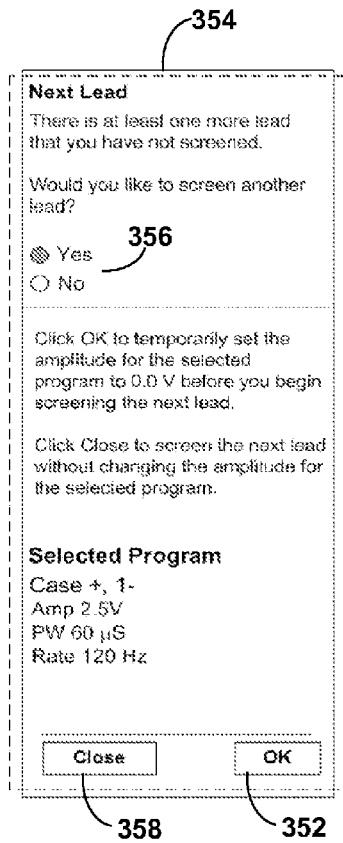
FIG. 31 is the example pop-up window of FIG. 30 after the clinician has selected to test another lead.
Figure 32:
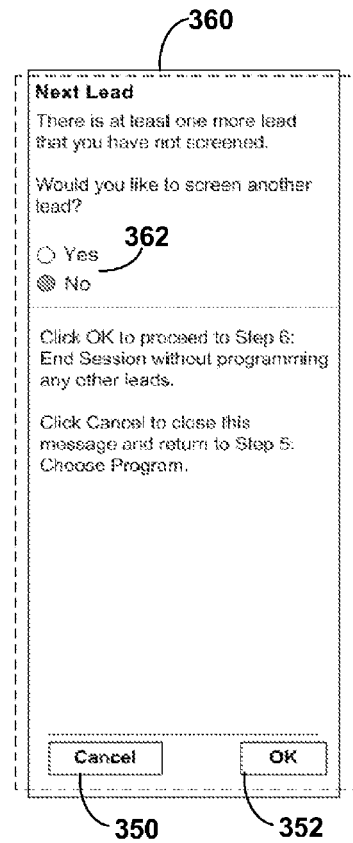
FIG. 32 is the example pop-up window of FIG. 30 after the clinician has chosen not to test another lead.

FIG. 30 is an example pop-up window after a program has been selected. FIG. 31 is the example pop-up window of FIG. 30 after the clinician has selected to test another lead. FIG. 32 is the example pop-up window of FIG. 30 after the clinician has chosen not to test another lead. FIGS. 30-32 allow the clinician to continue guided programming with another lead. GUI 346 presents the option of testing another lead to the clinician. The clinician may select the "Yes" or "No" in selection 348 to proceed. The clinician may select cancel button 350 to exit GUI 346. Ok button 352 is shaded to prevent the clinician from skipping GUI 346 prior to indicating whether another lead should be selected.

If the clinician selects "Yes," GUI 354 of FIG. 31 adds more information for the clinician to give the clinician the option to temporarily drop the amplitude for the current program to 0.0 V. Close button 358 does not change the amplitude to 0.0 V. Selecting ok button 352 causes the selected program to become the active program for lead and the clinician may continue guided programming with another lead.

If the clinician selects "No," GUI 360 of FIG. 32 adds more information for the clinician to give the clinician the option to proceed to the end of the session by selecting ok button 352 and activating the selected program. If the clinician selects cancel button 350, the clinician may exit GUI 360 and return to GUI 328 of FIG. 27, for example.

Figure 33:
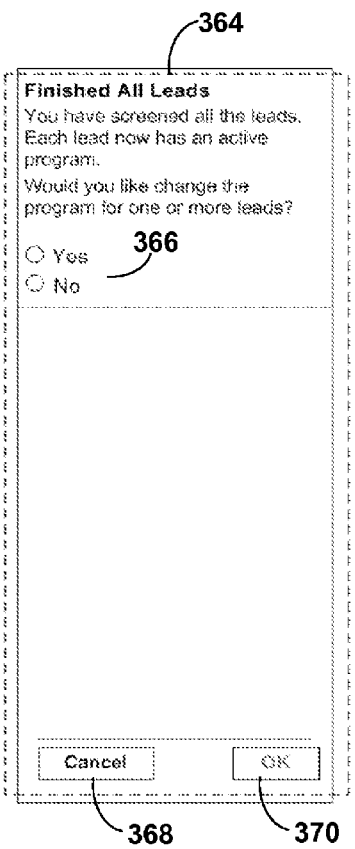
FIG. 33 is an example pop-up screen indicating that all leads have an active program.
Figure 34:
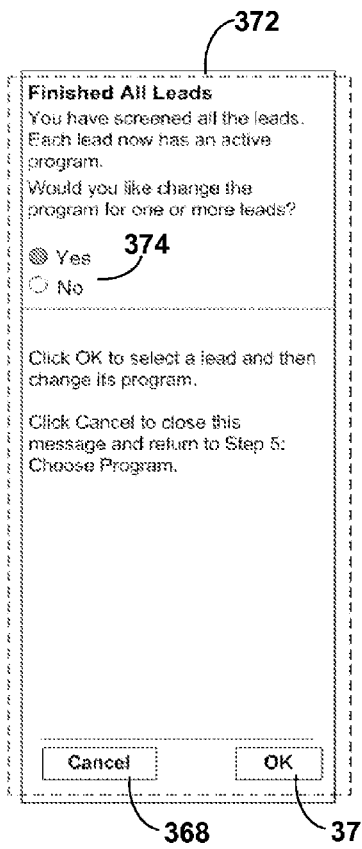
FIG. 34 is an example pop-up screen indicating that a clinician requests to change the program for a lead.
Figure 35:
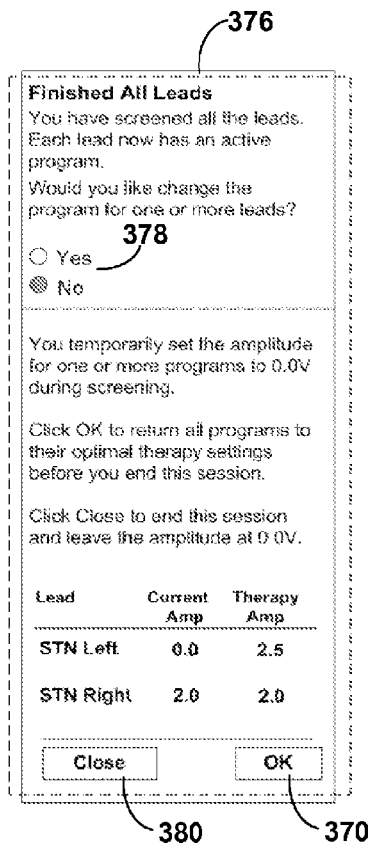
FIG. 35 is an example pop-up screen indicating that a clinician requests not to change a program for a lead.

FIG. 33 is an example pop-up screen indicating that all leads have an active program. FIG. 34 is an example pop-up screen prompting a clinician to indicate whether he or she wishes to change the program for a lead. FIG. 35 is an example pop-up screen indicating that a clinician requests not to change a program for a lead. FIGS. 33-35 illustrate how each GUI of a single pop-up window may change depending upon the selection made by the user. FIGS. 33-35 allow the clinician to finish programming all leads of system 10. GUI 364 presents the clinician with the option to change a selected program for one of the leads. The clinician may select "Yes" or "No" of selection 366. The clinician may select cancel button 368 to exit GUI 364. Ok button 370 is shaded to prevent the clinician from skipping GUI 364 without indicating whether they wish to change any of the programs for any of the leads.

If the clinician selects "Yes," GUI 372 of FIG. 34 adds more information for the clinician to give the clinician the option to select another lead and change the selected program for that lead. The clinician then may choose ok button 370 to select the lead and change programs. The clinician may select cancel button 368 to exit GUI 372 and return to GUI 328 of FIG. 27, for example.

If the clinician selects "No," GUI 376 of FIG. 35 adds more information for the clinician to give the clinician the option to return to any programs and temporarily drop the therapy amplitude to 0.0 V. If the clinician selects close button 380, the clinician exits GUI 376 and leaves the amplitude at 0.0 V. If the clinician selects ok button 370, the selected program becomes the active program for the current lead, and all programs for other leads temporarily set to 0.0 V are returned to their therapy setting. The programmer then sends the clinician to the end of session screen.

FIG. 36 is an example screen shot illustrating a final step of the example guided programming technique, which includes viewing end session information summarizing the programming session. As shown in FIG. 36, GUI 382 presents Step 6, or an end session summary, to the clinician. GUI includes information identifying the user of programmer 32 and the clinician (physician) to patient 12, which, in this example, are the same person. GUI 382 also identifies what programs have been selected for active use by IMD 20.

The clinician may provide feedback to programmer 32 regarding the overall session experience in rating menu 384. This feedback may allow programmer 32 to make slight adjustments to the guided programming process or send the information back to the manufacturer to improve programmer 32 or the guided programming process. The clinician may also select print report button 386 to print a copy of the programming information. The clinician may select previous button 388 to return to GUI 340 or select end session button 390 to exit GUI 382 and stop the guided programming process.

Figure 37:
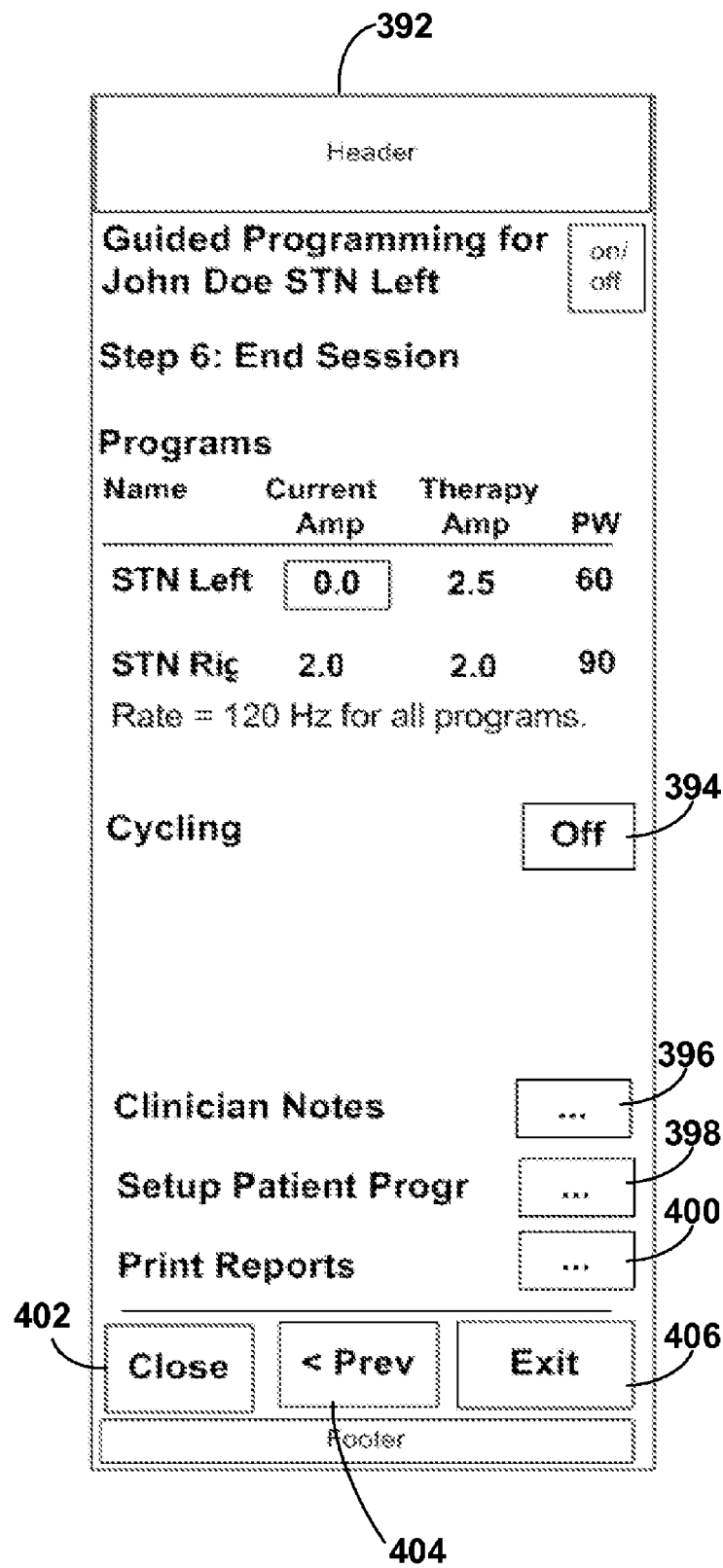
FIG. 37 is an example screen shot illustrating an end session informational screen.

FIG. 37 is an example screen shot illustrating an end session informational screen. FIG. 37 is an alternative embodiment to the embodiment illustrated in FIG. 36. As shown in FIG. 37, GUI 392 displays the active programs for therapy.

The clinician may return any program temporarily set to 0.0 V back to the defined therapy setting. The clinician may also select cycling button 394 to the off or on position in order to cycle between the programs. Cycling between the programs may allow IMD 20 to alternate stimulation between the pulses of each program or allow one program to run for a predetermined time and then switch to the other program. The clinician can view clinician notes by selecting notes box 396, setup a patient programmer by selecting setup box 398, and print reports by selecting print button 400. The clinician selects close button 402 to exit GUI 392, exit button to exit GUI 392, and previous button to return to the previous screen.

GUI 392 allows the clinician to enter other user interfaces that may enable further customization and control of the stimulation therapy. The clinician may use notes box 396 to enter observations, problems, successes, or any other items that the clinician wishes to store in relation to the therapy of patient 12. These clinician notes may be stored within IMD 20 or programmer 32. The clinician may also enter the setup of the patient programmer via GUI 392 and setup box 398. Setting up the patient programmer may include transmitting the chosen one or more programs for therapy, additional program options, and screening history in addition to setting authorization settings and other options available in the patient programmer. In addition, the clinician may prefer to print out a report of the guided programming by selecting print button 400. The report may include the selected programs and associated effects, screening history, program ratings, clinician notes, and any other information related to the guided programming or stimulation therapy.

Figure 38:
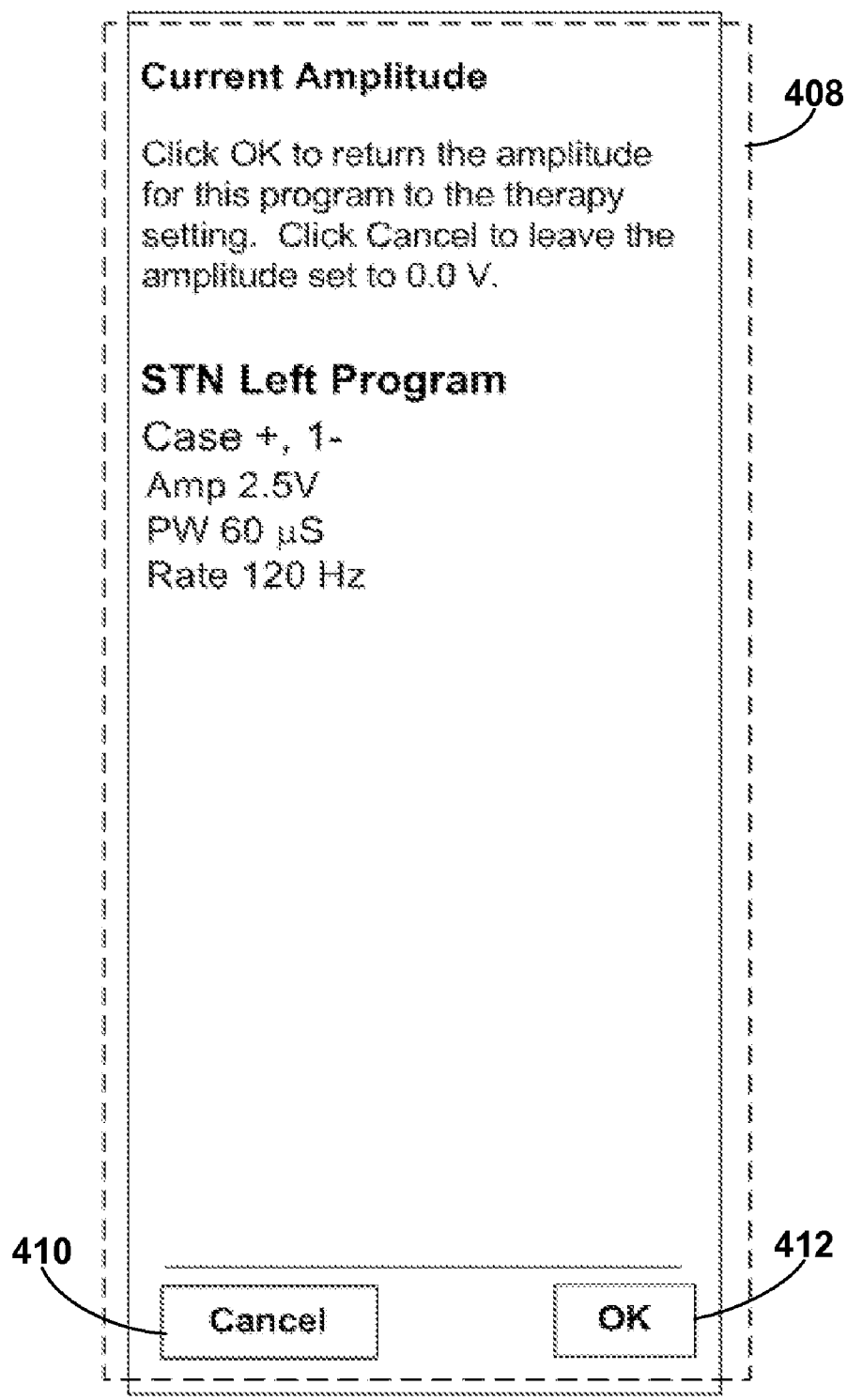
FIG. 38 is an example pop-up window indicating that the therapy setting will revert to the selected program settings.

FIG. 38 is an example pop-up window indicating that the therapy setting will revert to the selected program settings. As shown in FIG. 38, GUI 408 presents information to the clinician regarding the current amplitude of the program. If the clinician selects ok button 412, the amplitude setting for the selected program returns to the therapy setting from the 0.0 V setting. This change in amplitude is automatically transmitted to IMD 20. If the clinician selects cancel button 410, GUI 408 closes and programmer 32 returns to GUI 392 as no changes are made to the selected program.

Figure 39:
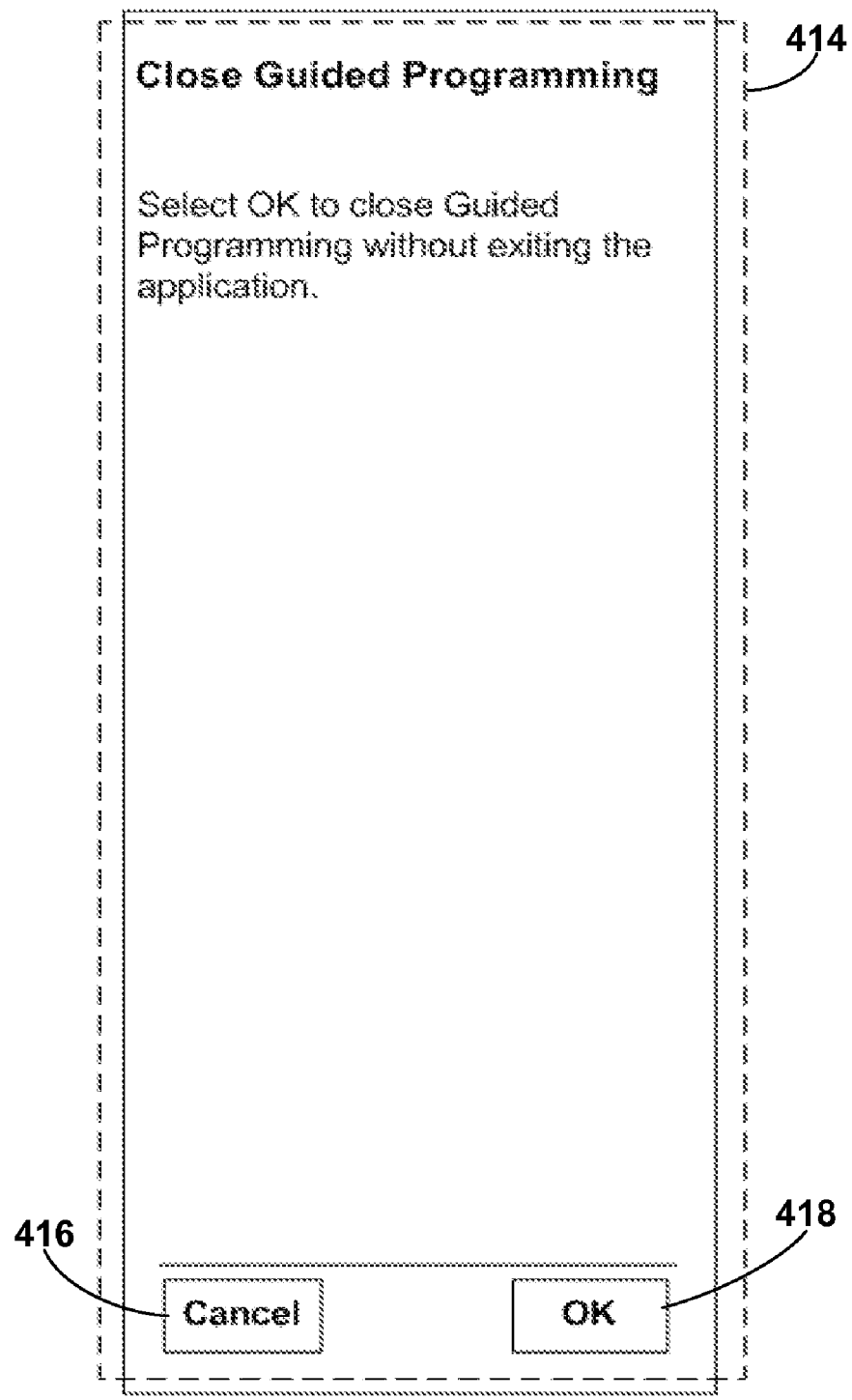
FIG. 39 is an example pop-up window indicating that guided programming will close.

FIG. 39 is an example pop-up window indicating to the clinician that guided programming will close. As shown in FIG. 39, GUI 414 presents a message to the clinician indicating that the clinician has attempted to close guided programming. GUI 414 appears at any time that the clinician selects a close button in any of FIGS. 9-40. However, GUI 414 will not appear when a pop-up screen is closed. If the clinician selects OK button 418, guided programming closes without exiting the programming application. Cancel button 416 does not close guided programming.

Figure 40:
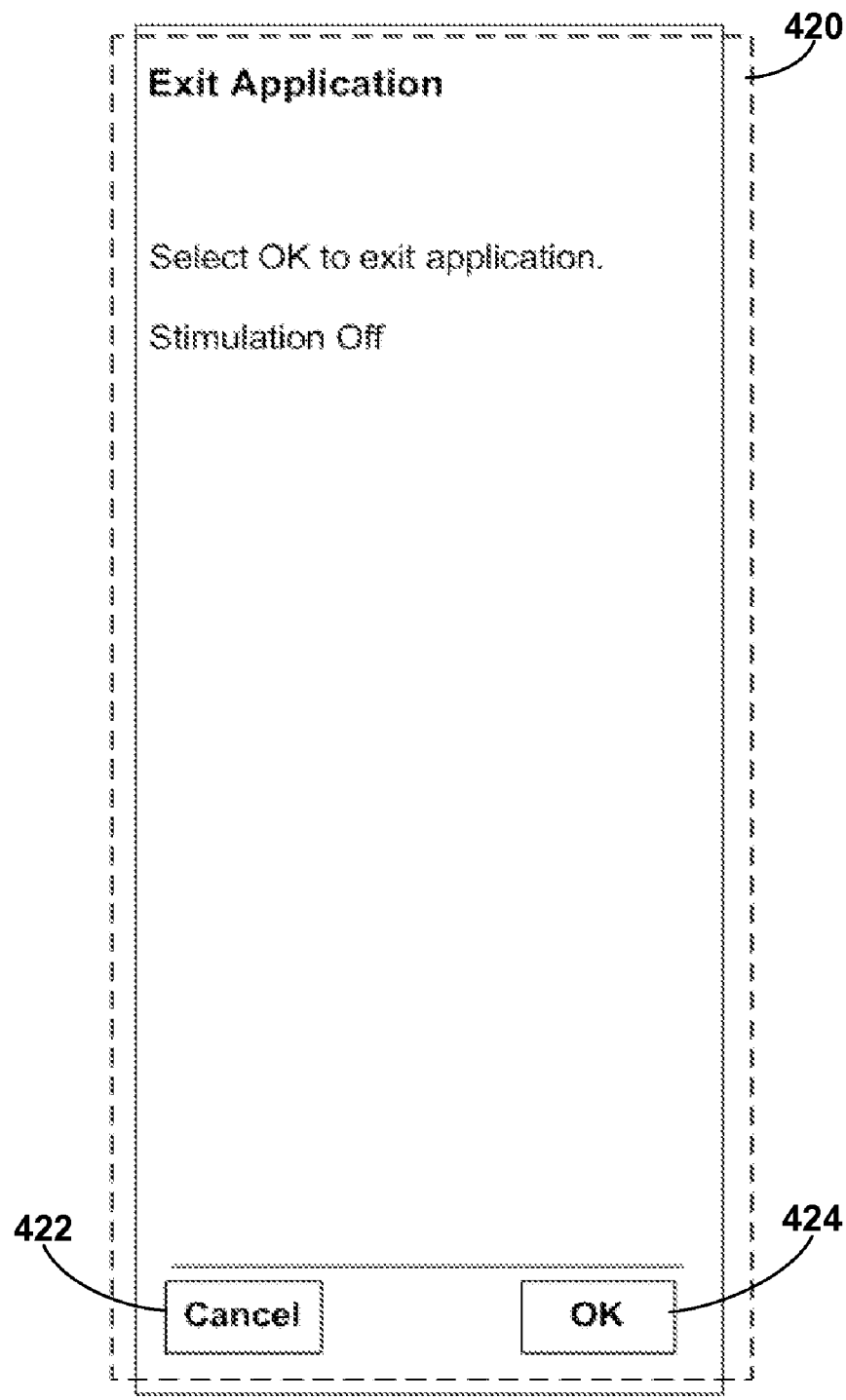
FIG. 40 is an example pop-up window indicating that the clinician is to exit the application.

FIG. 40 is an example pop-up window indicating to the clinician that the clinician is about to exit the programming application, e.g., has selected to exit the application. If the clinician selects cancel button 422, the application is not closed. If the clinician selects ok button 424, the clinician exits the application.

Figure 41A:
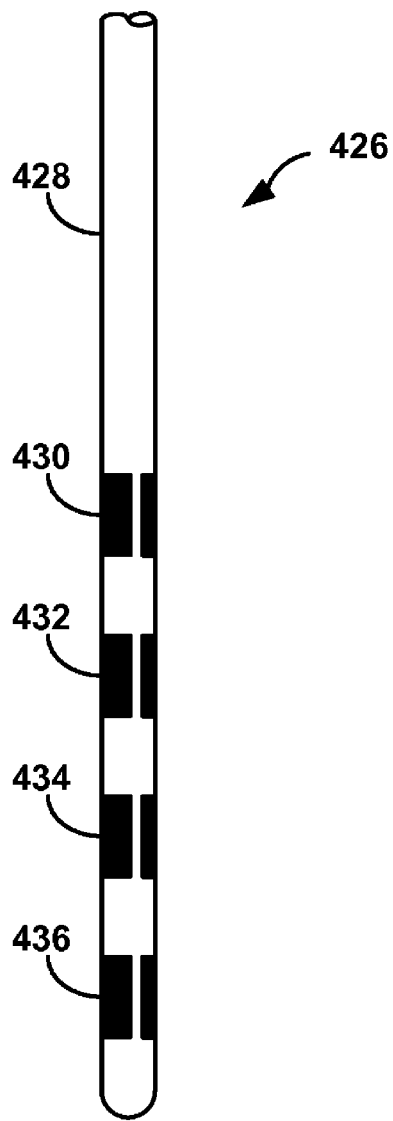
FIGS. 41A and 41B are conceptual diagrams illustrating segmented electrode leads.
Figure 41B:
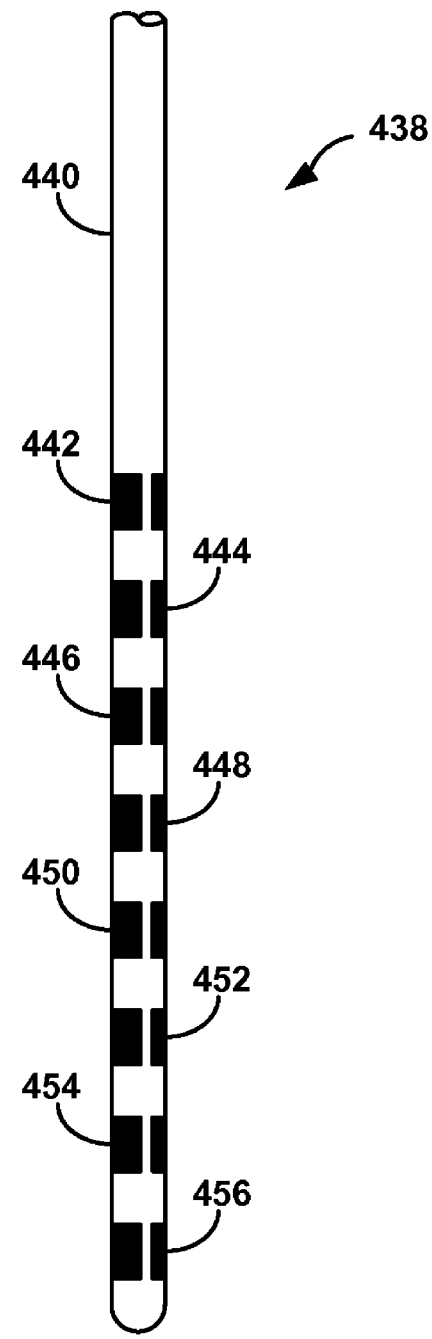

FIGS. 41A and 41B are conceptual diagrams illustrating example segmented electrode leads. Leads 426 and 438 are examples of leads with complex electrode array geometries, which may be used in systems according to the invention, e.g., similar to system 10 of FIG. 1. Leads with complex electrode array geometries, such as segmented leads 426 and 438, may also be programmed using guided programming techniques as described herein.

Leads 426 and 438 may be referred to as having segmented electrodes. In other words, electrodes are located at different axial positions along the longitudinal axis of leads 426 and 438, and two or more electrodes are located at different positions around the circumference of the each respective lead. Lead 426 includes lead housing or body 428, and electrode levels 430, 432, 434 and 436 at respective axial positions. Each electrode level includes at least two semi-circumferential, or arc, electrodes.

Lead 438 includes lead housing 440, and electrode levels 442, 444, 446, 448, 450, 452, 454 and 456. Each electrode level includes at least two semi-circumferential electrodes. In a preferred embodiment, each electrode level includes four individual semi-circumferential electrodes. In other embodiments, leads 426 and 438 may be constructed as a paddle lead with a generally rectangular shape or other type of lead with curved or multiple flat surfaces.

Figure 42:
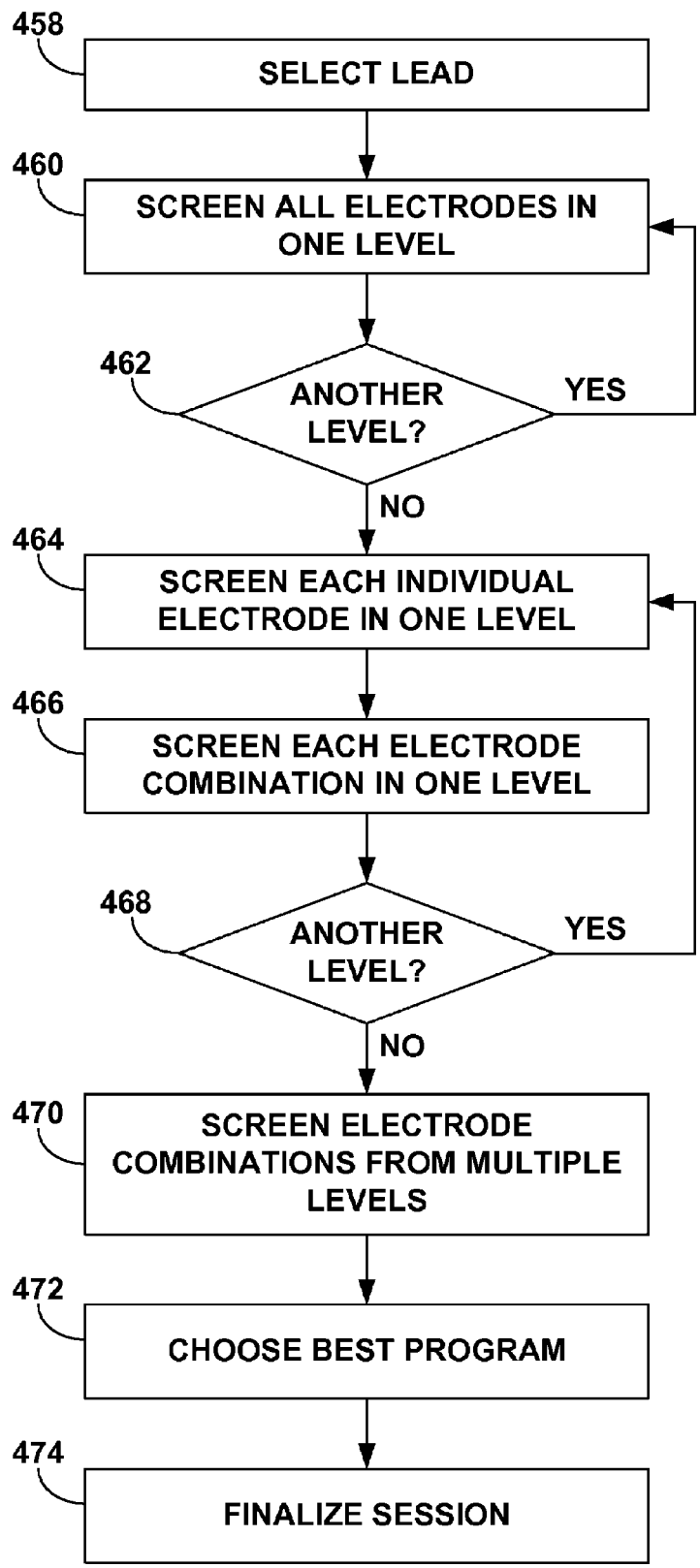
FIG. 42 is a flow diagram illustrating a technique for screening electrodes of a lead having a complex electrode array geometry.

FIG. 42 is a flow diagram illustrating a technique for screening electrodes of a lead having a complex electrode array geometry. FIG. 42 is an embodiment of the guided programming technique described in FIGS. 4-6, with differences between how to guide the clinician to new electrodes for screening, e.g., testing. As described in FIGS. 41A and 41B, a complex electrode array geometry includes multiple electrodes located around multiple surfaces, circumferential positions, radial positions, or the like of the lead, such as leads 426 and 438.

The clinician begins the guided programming process by selecting a particular lead using programmer 32 (458). Programmer 32 then selects one level of the lead and proceeds to test, or screen, the level with all electrodes of that level active together similar to a single ring electrode (460). Screening involves increasing the amplitude of the electrode level until patient 12 identifies good effects, side effects, or both. Programmer 32 will then prompt the clinician to log the effects and continue the process by increasing the amplitude and logging new effects, unless the side effects are too severe for patient 12. Once the screening of the current electrode level is complete, programmer 32 determines if another electrode level should be screened (462), e.g., automatically or based on clinician input.

Programmer 32 continues with guided programming by selecting one electrode level and screening each unipolar electrode of the electrode level (464). Programmer 32 may, for example, select the best one of a plurality of tested levels as indicated by positive and negative effects. The selection may be automatic or as directed by the clinician.

After each unipolar electrode in the electrode has been screened, programmer 32 may guide the clinician to screen each biopolar electrode combination within the same electrode level (466). In some examples, pairs of electrodes in each level may be tested as cathodes with a remote anode, e.g., IMD housing electrode, before moving to bipolar electrode combinations. If there are more electrode levels to screen (468), programmer 32 guides the clinician through screening of another electrode level (464). If all electrode levels have had unipolar and bipolar electrodes screened (468), programmer 32 will guide the clinician through screening other possible bipolar electrode combinations that include electrode pairs from adjacent electrode levels (470). In addition, programmer 32 may suggest electrode combinations that include electrode pairs from electrode levels anywhere on the lead or electrode combinations that include more than two electrodes.

From the screening information obtained by programmer 32, the programmer presents possible stimulation programs to the clinician and allows the clinician to select the best program for efficacious therapy (472). Programmer 32 may facilitate the selection of the best program by organizing the possible programs according to specific criteria. For example, the clinician may desire to sort the list of programs by best effect, least side effects, amplitude (therapeutic) range, or absolute amplitude (either voltage or current amplitude). The clinician may then finalize the session by printing a report of the session, setting up the patient programmer, or simply exiting the guided programming system (474).

Figure 43:
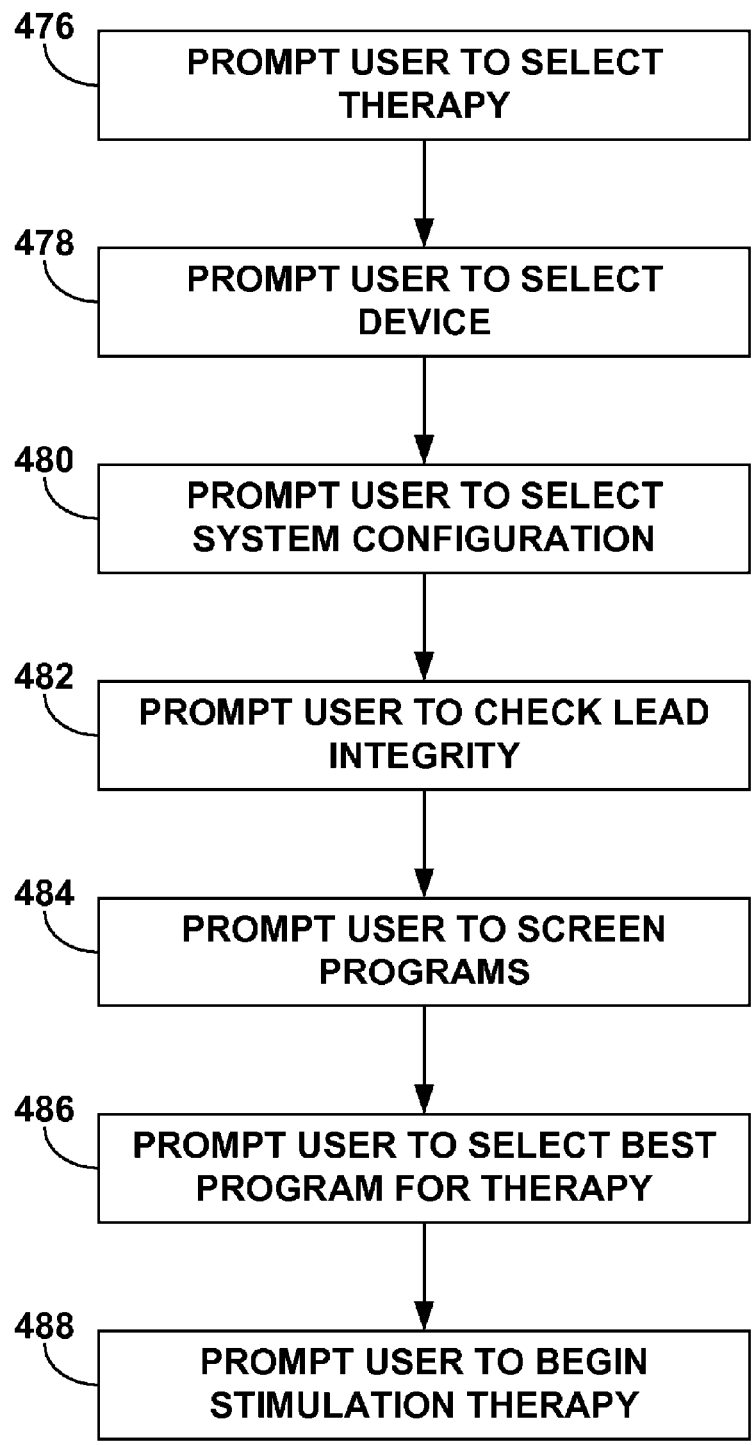
FIG. 43 is a flow diagram illustrating a technique for directing the programming flow of stimulation therapy using a programmer.

FIG. 43 is a flow diagram illustrating a technique for directing the programming flow of stimulation therapy using a programmer. As shown in FIG. 43, programmer 32 directs the clinician through the task of programming stimulation parameters for a stimulation therapy directed to patient 12. Programmer 32 initially prompts the clinician to select the type of therapy that will be delivered to patient 12, such as pain therapy or DBS therapy (476). Programmer 32 then prompts the clinician to select the type of IMD 20 that will be used to deliver the therapy (478).

Next, programmer 32 prompts the clinician to select the specific system configuration (480). For example, the system configuration may include the number and type of leads coupled to IMD 20, patient diagnosis, the baseline disease state of patient 12, and details related to IMD 20 implantation. Programmer 32 next prompts the clinician check the integrity of the leads through impedance measurements (482). Programmer 32 then allows the clinician to screen (or test) possible programs and log effects of the programs in order to determine the best programs for therapy (484). Once the programs have been screened, programmer 32 prompts the clinician to select the best one or more programs for each lead used in the therapy (486). Lastly, programmer 32 prompts the clinician to begin stimulation therapy using the selected stimulation programs (488).

Although discussed herein primarily with reference to a programmer that communicates with an IMD, the techniques of the invention may be employed by an IMD, as discussed above. A memory of the IMD may store the guiding information, and a processor of the IMD may apply the information to generate programs for testing and sorting the tested program as described herein. In such embodiments, the IMD may interact with a clinician via a clinician interface provided by a programmer that communicates with IMD.

Further, although the invention may be especially applicable to DBS, the invention alternatively may be applied more generally to any type of stimulation delivered according to programs via a plurality of configurable electrodes. As examples, spinal cord stimulation, deep brain stimulation, gastric nerve stimulation, sacral or pudendal nerve or other pelvic nerve stimulation, or dorsal root stimulation may benefit from the optimization technique described herein.

Various embodiments of the described invention may include processors that are realized by microprocessors, Application-Specific Integrated Circuits (ASIC), Field-Programmable Gate Arrays (FPGA), or other equivalent integrated logic circuitry. The processor may also utilize several different types of storage methods to hold computer-readable instructions for the device operation and data storage. These memory and storage media types may include a type of hard disk, random access memory (RAM), or flash memory, e.g. CompactFlash or SmartMedia. Each storage option may be chosen depending on the embodiment of the invention. While IMD 20 may contain permanent memory, programmer 32 may contain a more portable removable memory type to enable easy data transfer or offline data analysis.

Many embodiments of the invention have been described. Various modifications may be made without departing from the scope of the claims. These and other embodiments are within the scope of the following claims.

The invention claimed is:

1. A method comprising:
   providing test stimulation to a patient according to a plurality of programs, wherein each of the plurality of programs comprise an electrode combination;
   for at least one of the plurality of programs, receiving a positive input via a user interface that indicates a positive effect resulting from provision of stimulation according to the program;
   for at least one of the plurality of programs, receiving a negative input via the user interface that indicates an adverse effect resulting from provision of stimulation according to the program; and
   automatically sorting the plurality of tested programs based upon the positive input, the negative input, and a therapy window for each of the plurality of tested programs, wherein the therapy window is characterized by a minimum therapeutic threshold that indicates a magnitude of a stimulation parameter at which positive effects on the patient are noted via the positive input, and wherein the therapy window is characterized by a maximum therapeutic threshold that indicates a magnitude of the stimulation parameter at which adverse effects on the patient are noted via the negative input.

2. The method of claim 1, wherein providing test stimulation according to a plurality of programs comprises providing test stimulation via a plurality of unipolar electrode combinations.

3. The method of claim 1, further comprising automatically generating at least one program that comprises a bipolar electrode configuration when none of a plurality of tested unipolar programs reach a threshold positive effect rating.

4. The method of claim 1, further comprising automatically generating at least one program that comprises a bipolar electrode configuration when all of a plurality of tested unipolar programs reach a threshold adverse effect rating.

5. The method of claim 1, further comprising automatically generating another program based upon the positive input and the negative input.

6. The method of claim 5, wherein at least one of the positive input and the negative input indicates an anatomical region of the patient.

7. The method of claim 5, wherein the automatically generated other program does not include at least one electrode associated with the adverse effect.

8. The method of claim 5, wherein the automatically generated other program includes at least one electrode associated with the positive effect.

9. The method of claim 1, wherein:
   receiving the positive input further comprises rating at least one positive effect associated with at least one of the plurality of programs; and
   receiving the negative input further comprises rating at least one adverse effect associated with at least one of the plurality of programs.

10. The method of claim 1, further comprising receiving a selection input selecting at least one of the plurality of tested programs for providing chronic stimulation therapy.

11. The method of claim 1, wherein each of the plurality of programs comprise a pulse rate, a pulse width, and at least one of a voltage amplitude or a current amplitude.

12. The method of claim 1, wherein providing test stimulation comprises providing stimulation from a lead that comprises at least two electrodes located at different positions around a periphery of the lead.

13. The method of claim 12, wherein the lead comprises a plurality of electrode levels, each of the electrode levels comprising a plurality of electrodes located at different positions around a periphery of the lead, and providing test stimulation comprises:
   iteratively providing test stimulation via each of the levels with all of the electrodes at the level activated; and
   after iteratively providing test stimulation via each of the levels, iteratively providing test stimulation via the electrodes of a selected one of the levels.

14. The method of claim 1, wherein at least one of the positive input and the negative input is associated with at least one of tremors, muscle tone, motor speed, balance, or gait of the patient.

15. The method of claim 1, wherein providing test stimulation comprises increasing an amplitude of at least one of the programs until at least one adverse effect is intolerable for the patient to identify the maximum therapeutic threshold.

16. The method of claim 1, further comprising sorting the plurality of tested programs based upon device longevity.

17. The method of claim 1, wherein automatically sorting the plurality of tested programs further comprises:
   weighting each of the positive input and the negative input; and
   automatically sorting the plurality of tested programs based upon the weighted positive input and weighted negative input.

18. The method of claim 1, further comprising automatically sorting the plurality of tested programs based on a difference between the maximum therapeutic threshold and the minimum therapeutic threshold.

19. The method of claim 1, wherein the stimulation parameter includes at least one of an amplitude of the stimulation, a pulse rate of the stimulation, or a pulse width of the stimulation.

20. The method of claim 1, wherein the maximum therapeutic threshold is one of a voltage or current amplitude at which positive effects are noted by the patient via the positive input, and wherein the minimum therapeutic threshold is one of a voltage or current amplitude at which negative effects are noted by the patient via the negative input.

21. A system comprising:
   a stimulation signal generator that provides test stimulation to a patient according to a plurality of programs, wherein each of the plurality of programs comprise an electrode combination;
   a lead coupled to the stimulation signal generator;
   a user interface; and
   a processor that:
      receives a positive input via the user interface that indicates a positive effect resulting from provision of stimulation according to the program for at least one of the plurality of programs;
      receives a negative input via the user interface that indicates an adverse effect resulting from provision of stimulation according to the program for at least one of the plurality of programs; and
      automatically sorts the plurality of tested programs based upon the positive input, the negative input, and a therapy window for each of the plurality of tested programs, wherein the therapy window is characterized by a minimum therapeutic threshold that indicates a magnitude of a stimulation parameter at which positive effects on the patient are noted via the positive input, and wherein the therapy window is characterized by a maximum therapeutic threshold that indicates a magnitude of the stimulation parameter at which adverse effects on the patient are noted via the negative input.

22. The system of claim 21, wherein the stimulation signal generator provides test stimulation via at least one program that comprises a unipolar electrode combination.

23. The system of claim 21, wherein the processor automatically generates at least one program that comprises a bipolar electrode configuration when none of a plurality of tested unipolar programs reach a threshold positive effect.

24. The system of claim 21, wherein the processor automatically generates at least one program that comprises a bipolar electrode configuration when all of a plurality of tested unipolar programs reach a threshold adverse effect.

25. The system of claim 21, wherein the processor automatically generates another program based upon the positive input and the negative input.

26. The system of claim 25, wherein at least one of the positive input and the negative input indicates an anatomical region of the patient.

27. The system of claim 25, wherein the automatically generated other program does not include at least one electrode associated with the adverse effect.

28. The system of claim 25, wherein the automatically generated other program includes at least one electrode associated with the positive effect.

29. The system of claim 21, wherein:
the positive input rates at least one positive effect associated with at least one of the plurality of programs; and
the negative input rates at least one adverse effect associated with at least one of the plurality of programs.

30. The system of claim 21, wherein the processor receives a selection input selecting at least one of the plurality of tested programs for providing chronic stimulation therapy.

31. The system of claim 21, wherein each of the plurality of programs comprise, a pulse rate, a pulse width, and at least one of a voltage amplitude and a current amplitude.

32. The system of claim 21, wherein the lead comprises at least two or more electrodes located at different positions around a periphery of the lead, wherein the test stimulation is delivered to the patient via the lead.

33. The system of claim 21, wherein at least one of the positive input and the negative input is associated with at least one of tremors, muscle tone, motor speed, balance, or gait of the patient.

34. The system of claim 21, wherein the processor instructs the stimulation signal generator to provide test stimulation by increasing an amplitude of at least one of the programs until at least one adverse effect is intolerable for the patient to identify the maximum therapeutic threshold.

35. The system of claim 21, wherein the processor sorts the plurality of tested programs based upon device longevity.

36. The system of claim 21, wherein the processor:
weights each of the positive input and the negative input; and
automatically sorts the plurality of tested programs based upon the weighted positive input and weighted negative input.

37. The system of claim 21, wherein the processor automatically sorts the plurality of tested programs based on a difference between the maximum therapeutic threshold and the minimum therapeutic threshold.

38. The system of claim 21, wherein the stimulation parameter includes at least one of an amplitude of the stimulation, a pulse rate of the stimulation, or a pulse width of the stimulation.

39. The system of claim 21, wherein the maximum therapeutic threshold is one of a voltage or current amplitude at which positive effects are noted by the patient via the positive input, and wherein the minimum therapeutic threshold is one of a voltage or current amplitude at which negative effects are noted by the patient via the negative input.

40. A non-transitory computer-readable medium comprising instructions that cause a processor to:
provide test stimulation to a patient according to a plurality of programs, wherein each of the plurality of programs comprise an electrode combination;
for at least one of the plurality of programs, receive a positive input via a user interface that indicates a positive effect resulting from provision of stimulation according to the program;
for at least one of the plurality of programs, receive a negative input via the user interface that indicates an adverse effect resulting from provision of stimulation according to the program; and
automatically sort the plurality of tested programs based upon the positive input, the negative input, and a therapy window for each of the plurality of tested programs, wherein the therapy window is characterized by a minimum therapeutic threshold that indicates a magnitude of a stimulation parameter at which positive effects on the patient are noted via the positive input, and wherein the therapy window is characterized by a maximum therapeutic threshold that indicates a magnitude of the stimulation parameter at which adverse effects on the patient are noted via the negative input.

41. The computer-readable medium of claim 40, further comprising instructions that cause the processor to automatically generate at least one program that comprises a unipolar electrode configuration.

42. The computer-readable medium of claim 40, further comprising instructions that cause the processor to automatically generate at least one program that comprises a bipolar electrode configuration when none of a plurality of tested unipolar programs reach a threshold positive effect rating.

43. The computer-readable medium of claim 40, further comprising instructions that cause the processor to automatically generate at least one program that comprises a bipolar electrode configuration when all of a plurality of tested unipolar programs reach a threshold adverse effect rating.

44. The computer-readable medium of claim 40, further comprising instructions that cause the processor to automatically generate another program based upon the positive input and the negative input.

45. The computer-readable medium of claim 40, wherein:
the positive input rates at least one positive effect associated with at least one of the plurality of programs; and
the negative input rates at least one adverse effect associated with at least one of the plurality of programs.

46. The computer-readable medium of claim 40, further comprising instructions that cause the processor to receive a selection input selecting at least one of the plurality of tested programs for providing chronic stimulation therapy.

47. The computer-readable medium of claim 40, wherein at least one of the positive input and the negative input is associated with at least one of tremors, muscle tone, motor speed, balance, or gait of the patient.

48. The computer-readable medium of claim 40, wherein the instructions that cause the processor to provide test stimulation comprise instructions that cause the processor to increase an amplitude of at least one of the programs until at least one adverse effect is intolerable for the patient to identify the maximum therapeutic threshold.

49. The computer-readable medium of claim 40, further comprising instructions that cause the processor to sort the plurality of tested programs based upon device longevity.

* * * * *